(12) United States Patent
Karumanchi et al.

(10) Patent No.: US 10,413,591 B2
(45) Date of Patent: *Sep. 17, 2019

(54) METHODS OF DIAGNOSING AND TREATING COMPLICATIONS OF PREGNANCY

(71) Applicant: Beth Israel Deaconess Medical Center, Inc., Boston, MA (US)

(72) Inventors: S. Ananth Karumanchi, Chestnut Hill, MA (US); Vikas P. Sukhatme, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 578 days.

This patent is subject to a terminal disclaimer.

(21) Appl. No.: 14/729,358

(22) Filed: Jun. 3, 2015

(65) Prior Publication Data

US 2017/0072018 A1 Mar. 16, 2017

Related U.S. Application Data

(63) Continuation of application No. 13/095,500, filed on Apr. 27, 2011, now abandoned, which is a continuation of application No. 11/235,577, filed on Sep. 26, 2005, now abandoned.

(60) Provisional application No. 60/613,170, filed on Sep. 24, 2004.

(51) Int. Cl.
| | |
|---|---|
| *A61K 39/395* | (2006.01) |
| *A61K 38/18* | (2006.01) |
| *A61K 31/4439* | (2006.01) |
| *A61K 31/455* | (2006.01) |
| *A61K 31/513* | (2006.01) |
| *A61K 31/522* | (2006.01) |
| *A61K 38/22* | (2006.01) |
| *C07K 16/28* | (2006.01) |
| *G01N 33/68* | (2006.01) |
| *A61K 45/06* | (2006.01) |
| *C07K 14/495* | (2006.01) |
| *G01N 33/74* | (2006.01) |

(52) U.S. Cl.
CPC ...... *A61K 38/1841* (2013.01); *A61K 31/4439* (2013.01); *A61K 31/455* (2013.01); *A61K 31/513* (2013.01); *A61K 31/522* (2013.01); *A61K 38/1866* (2013.01); *A61K 38/1875* (2013.01); *A61K 38/1891* (2013.01); *A61K 38/22* (2013.01); *A61K 39/3955* (2013.01); *A61K 45/06* (2013.01); *C07K 14/495* (2013.01); *C07K 16/2863* (2013.01); *C07K 16/2896* (2013.01); *G01N 33/689* (2013.01); *G01N 33/74* (2013.01); *G01N 2333/71* (2013.01); *G01N 2500/00* (2013.01); *G01N 2800/368* (2013.01); *G01N 2800/60* (2013.01); *Y10T 436/143333* (2015.01)

(58) Field of Classification Search
None
See application file for complete search history.

(56) References Cited

U.S. PATENT DOCUMENTS

| | | |
|---|---|---|
| 5,194,596 A | 3/1993 | Tischer et al. |
| 5,219,739 A | 6/1993 | Tischer et al. |
| 5,238,819 A | 8/1993 | Roberts et al. |
| 5,240,848 A | 8/1993 | Keck et al. |
| 5,332,671 A | 7/1994 | Ferrara et al. |
| 5,543,138 A | 8/1996 | Keith |
| 5,641,636 A | 6/1997 | Strauss, III et al. |
| 5,660,827 A | 8/1997 | Thorpe et al. |
| 5,712,395 A | 1/1998 | App et al. |
| 5,719,120 A | 2/1998 | Letarte et al. |
| 5,750,345 A | 5/1998 | Bowie |
| 5,763,441 A | 6/1998 | App et al. |
| 5,817,528 A | 10/1998 | Bohm et al. |
| 5,830,847 A | 11/1998 | Letarte et al. |
| 5,830,879 A | 11/1998 | Isner |
| 5,895,783 A | 4/1999 | Garfield et al. |
| 5,910,482 A | 6/1999 | Yallampalli et al. |
| 5,928,641 A | 7/1999 | Seon |
| 5,958,715 A | 9/1999 | Muller |
| 5,989,811 A | 11/1999 | Veltri et al. |
| 6,100,071 A | 8/2000 | Davis-Smyth et al. |
| 6,258,787 B1 | 7/2001 | Isner |
| 6,365,157 B2 | 4/2002 | Rockwell et al. |
| 6,376,199 B1 | 4/2002 | Caniggia et al. |
| 6,399,585 B1 | 6/2002 | Larson et al. |
| 6,410,322 B1 | 6/2002 | Robinson |
| 6,447,768 B1 | 9/2002 | van Zonneveld et al. |
| 6,528,676 B1 | 3/2003 | D'Amato et al. |
| 6,562,957 B1 | 5/2003 | Letarte et al. |
| 6,613,757 B1 | 9/2003 | Garfield et al. |
| 6,660,534 B2 | 12/2003 | McVicker et al. |

(Continued)

FOREIGN PATENT DOCUMENTS

| | | |
|---|---|---|
| WO | WO-96/16666 A1 | 6/1996 |
| WO | WO-98/28006 A1 | 7/1998 |

(Continued)

OTHER PUBLICATIONS

Merck Manual of Diagnosis and Therapy, ed. Beers and Berkow, 17th edition, Merck Research Laboratories, 1999, pp. 1629-1648.*

(Continued)

*Primary Examiner* — Michael Szperka
(74) *Attorney, Agent, or Firm* — Clark & Elbing LLP

(57) ABSTRACT

Disclosed herein are methods for diagnosing a pregnancy related hypertensive disorder or a predisposition to a pregnancy related hypertensive disorder by measuring the level or biological activity of soluble endoglin. Also disclosed herein are methods for treating a pregnancy related hypertensive disorder, such as pre-eclampsia and eclampsia, using compounds that alter soluble endoglin levels or biological activity.

**27 Claims, 28 Drawing Sheets
(5 of 28 Drawing Sheet(s) Filed in Color)
Specification includes a Sequence Listing.**

(56) References Cited

U.S. PATENT DOCUMENTS

| | | |
|---|---|---|
| 6,677,300 B1 | 1/2004 | Schreiner et al. |
| 7,030,083 B2 | 4/2006 | Schreiner et al. |
| 7,335,362 B2 | 2/2008 | Karumanchi et al. |
| 7,407,659 B2 | 8/2008 | Karumanchi et al. |
| 7,435,419 B2 | 10/2008 | Karumanchi et al. |
| 7,740,849 B2 * | 6/2010 | Karumanchi ...... A61K 31/4439 424/139.1 |
| 7,754,495 B2 | 7/2010 | Caniggia et al. |
| 7,955,805 B2 | 6/2011 | Karumanchi et al. |
| 2001/0056068 A1 | 12/2001 | Chwalisz et al. |
| 2003/0049823 A1 | 3/2003 | Sessa |
| 2003/0099651 A1 | 5/2003 | Leibovitz |
| 2003/0114407 A1 | 6/2003 | Monia et al. |
| 2003/0114412 A1 | 6/2003 | Ward et al. |
| 2003/0144298 A1 | 7/2003 | Curwen et al. |
| 2003/0220262 A1 | 11/2003 | Schreiner et al. |
| 2004/0038305 A1 | 2/2004 | Poston et al. |
| 2004/0121343 A1 | 6/2004 | Buechler et al. |
| 2004/0126828 A1 | 7/2004 | Karumanchi et al. |
| 2005/0025762 A1 | 2/2005 | Karumanchi et al. |
| 2005/0043227 A1 | 2/2005 | Compernolle et al. |
| 2005/0148040 A1 | 7/2005 | Thadhani et al. |
| 2005/0170444 A1 | 8/2005 | Karumanchi et al. |
| 2005/0181451 A1 | 8/2005 | Bates |
| 2005/0256199 A1 | 11/2005 | Durley et al. |
| 2006/0067937 A1 | 3/2006 | Karumanchi et al. |
| 2006/0183175 A1 | 8/2006 | Buhimschi et al. |
| 2010/0247650 A1 | 9/2010 | Smith et al. |

FOREIGN PATENT DOCUMENTS

| | | |
|---|---|---|
| WO | WO-98/40747 A1 | 9/1998 |
| WO | WO-02/37120 A2 | 5/2002 |
| WO | WO-2004/008946 A2 | 1/2004 |
| WO | WO-2005/077007 A2 | 8/2005 |
| WO | WO-2006/034507 A2 | 3/2006 |
| WO | WO-2006/069373 A2 | 6/2006 |
| WO | WO-2008/030283 A1 | 3/2008 |

OTHER PUBLICATIONS

Rudikoff et al., Proc Natl Acad Sci U S A. Mar. 1982;79(6):1979-83.*

Janeway et al., Immunobiology, 3rd edition, 1997, Garland Publishing Inc., pp. 3:1-3:11.*

Office Action for Canadian Patent Application No. 2581336, dated Oct. 14, 2016 (4 pages).

Ahmed et al., "Regulation of placental vascular endothelial growth factor (VEGF) and placenta growth factor (PlGF) and soluble Flt-1 by oxygen—a review," Placenta. 21 Suppl A:S16-24 (2000).

Al Kadi et al., "A prospective, longitudinal study of the renin-angiotensin system, prostacyclin and thromboxane in the first trimester of normal human pregnancy: association with birthweight," Hum Reprod. 20(11):3157-62 (2005).

Alberts et al., "Endoglin gene polymorphism as a risk factor for sporadic intracerebral hemorrhage," Ann Neurol. 41(5):683-6 (1997).

Barleon et al., "Soluble VEGFR-1 secreted by endothelial cells and monocytes is present in human serum and plasma from healthy donors," Angiogenesis. 4(2):143-54 (2001).

Beers et al., *The Merck Manual of Diagnosis and Therapy, 17th Edition*. Merck Research Laboratories, 2057-9 (1999) (4 pages).

Belgore et al., "Measurement of free and complexed soluble vascular endothelial growth factor receptor, Flt-1, in fluid samples: development and application of two new immunoassays," Clin Sci (Lond). 100(5):567-75 (2001).

Belgore et al., "Plasma levels of vascular endothelial growth factor and its soluble receptor (SFlt-1) in essential hypertension," Am J Cardiol. 87(6):805-7 (2001).

Belgore et al., "sFlt-1, a potential antagonist for exogenous VEGF," Circulation. 102(15):E108-9 (2000).

Belgore et al., "Vascular endothelial growth factor and its receptor, Flt-1, in smokers and non-smokers," Br J Biomed Sci. 57(3):207-13 (2000).

Bellón et al., "Identification and expression of two forms of the human transforming growth factor-beta-binding protein endoglin with distinct cytoplasmic regions," Eur J lmmunol. 23(9):2340-5 (1993).

Bernabeu et al., "Interaction between the CD45 antigen and phytohemagglutinin. Inhibitory effect on the lectin-induced T cell proliferation by anti-CD45 monoclonal antibody," Eur J Immunol. 17(10):1461-6 (1987).

Bouloumié et al., "Vascular endothelial growth factor up-regulates nitric oxide synthase expression in endothelial cells," Cardiovasc Res. 41(3):773-80 (1999).

Brennecke et al., "Reduction of placental nitric oxide synthase activity in pre-eclampsia," Clin Sci (Lond). 93(1):51-5 (1997).

Brockelsby et al., "VEGF via VEGF receptor-1 (Flt-1) mimics preeclamptic plasma in inhibiting uterine blood vessel relaxation in pregnancy: implications in the pathogenesis of preeclampsia," Lab Invest. 79(9):1101-11 (1999).

Buhimschi et al., "Pre-eclampsia-like conditions produced by nitric oxide inhibition: effects of L-arginine, D-arginine and steroid hormones," Hum Reprod. 10(10):2723-30 (1995).

Burrows et al., "Up-regulation of endoglin on vascular endothelial cells in human solid tumors: implications for diagnosis and therapy," Clin Cancer Res. 1(12):1623-34 (1995).

Calabrò et al., "Differential levels of soluble endoglin (CD105) in myeloid malignancies," J Cell Physiol. 194(2):171-5 (2003).

Caniggia et al., "Endoglin Regulates Trophoblast Invasion in Human Placental Villous Tissue Explant," Biol. Reprod. Suppl. 52:164 (1995).

Caniggia et al., "Endoglin regulates trophoblast differentiation along the invasive pathway in human placental villous explants," Endocrinology. 138(11):4977-88 (1997).

Chaiworapongsa et al., "Plasma soluble vascular endothelial growth factor receptor-1 concentration is elevated prior to the clinical diagnosis of pre-eclampsia," J Matern Fetal Neonatal Med. 17(1):3-18 (2005).

Charnock-Jones et al., "Determination of the Circulating Levels of the Soluble Form of the VEGF-R1 (sFlt-1) in Women at High Risk of Developing Pre-Eclampsia," J Soc Gynecol Investig. 10:166A Abstract No. 230 (2003).

Charnock-Jones et al., "Identification and localization of alternately spliced mRNAs for vascular endothelial growth factor in human uterus and estrogen regulation in endometrial carcinoma cell lines," Biol Reprod. 48(5):1120-8 (1993).

Clark et al., "A vascular endothelial growth factor antagonist is produced by the human placenta and released into the maternal circulation," Biol Reprod. 59(6):1540-8 (1998).

Cockell et al., "Human placental syncytiotrophoblast microvillous membranes impair maternal vascular endothelial function," Br J Obstet Gynaecol. 104(2):235-40 (1997).

Eremina et al., "Glomerular-specific alterations of VEGF-A expression lead to distinct congenital and acquired renal diseases," J Clin Invest. 111(5):707-16 (2003).

Ferguson, "Meeting highlights. Highlights of the 48th scientific sessions of the American College of Cardiology," Circulation. 100(6):570-5 (1999).

Ferrara et al., "The role of vascular endothelial growth factor in angiogenesis," Acta Haematol. 106(4):148-56 (2001).

Fonsatti et al., "Emerging role of endoglin (CD105) as a marker of angiogenesis with clinical potential in human malignancies," Curr Cancer Drug Targets. 3(6):427-32 (2003).

Fonsatti et al., "Endoglin (CD105): a powerful therapeutic target on tumor-associated angiogenetic blood vessels," Oncogene. 22(42):6557-63 (2003).

Fonsatti et al., "Endoglin is a suitable target for efficient imaging of solid tumors: in vivo evidence in a canine mammary carcinoma model," Clin Cancer Res. 6(5):2037-43 (2000).

Fulton et al., "Regulation of endothelium-derived nitric oxide production by the protein kinase Akt," Nature. 399(6736):597-601 (1999).

(56) References Cited

OTHER PUBLICATIONS

Geissbuehler et al., "Altered plasma neurokinin B levels in patients with pre-eclampsia," Arch Gynecol Obstet. 276(2):151-7 (2007).
Gille et al., "Analysis of biological effects and signaling properties of Flt-1 (VEGFR-1) and KDR (VEGFR-2). A reassessment using novel receptor-specific vascular endothelial growth factor mutants," J Biol Chem. 276(5):3222-30 (2001).
Guerrero-Esteo et al., "Extracellular and cytoplasmic domains of endoglin interact with the transforming growth factor-beta receptors I and II," J Biol Chem. 277(32):29197-209 (2002).
Gélinas et al., "Immediate and delayed VEGF-mediated NO synthesis in endothelial cells: role of PI3K, Pkc and PLC pathways," Br J Pharmacol. 137(7):1021-30 (2002).
Gómez-Esquer et al., "mRNA expression of the angiogenesis markers VEGF and CD105 (endoglin) in human breast cancer," Anticancer Res. 24(3a):1581-5 (2004).
Hayashi et al., "Changes in urinary excretion of six biochemical parameters in normotensive pregnancy and preeclampsia," Am J Kidney Dis. 39(2):392-400 (2002).
He et al., "Alternative splicing of vascular endothelial growth factor (VEGF)-R1 (FLT-1) pre-mRNA is important for the regulation of VEGF activity," Mol Endocrinol. 13(4):537-45 (1999).
He et al., "Vascular endothelial growth factor signals endothelial cell production of nitric oxide and prostacyclin through flk-1/KDR activation of c-Src," J Biol Chem. 274(35):25130-5 (1999).
Heeschen et al., "Nicotine stimulates angiogenesis and promotes tumor growth and atherosclerosis," Nat Med. 7(7):833-9 (2001).
Helske et al., "Expression of vascular endothelial growth factor receptors 1, 2 and 3 in placentas from normal and complicated pregnancies," Mol Hum Reprod. 7(2):205-10 (2001).
Hornig et al., "Release and complex formation of soluble VEGFR-1 from endothelial cells and biological fluids," Lab Invest. 80(4):443-54 (2000).
Hunter et al., "Serum levels of vascular endothelial growth factor in preeclamptic and normotensive pregnancy," Hypertension. 36(6):965-9 (2000).
Irminger-Finger et al., "Preeclampsia: a danger growing in disguise," Int J Biochem Cell Biol. 40(10):1979-83 (2008).
Jakubowski et al., "Biochemical and pharmacological activity of arene-fused prostacyclin analogues on human platelets," Prostaglandins. 47(3):189-201 (1994).
Kendall et al., "Identification of a natural soluble form of the vascular endothelial growth factor receptor, FLT-1, and its heterodimerization with KDR," Biochem Biophys Res Commun. 226(2):324-8 (1996).
Kendall et al., "Inhibition of vascular endothelial cell growth factor activity by an endogenously encoded soluble receptor," Proc Natl Acad Sci U S A. 90(22):10705-9 (1993).
Kincaid-Smith, "The renal lesion of preeclampsia revisited," Am J Kidney Dis. 17(2):144-8 (1991).
Kingsley et al., "The TGF-beta superfamily: new members, new receptors, and new genetic tests of function in different organisms," Genes Dev. 8(2):133-46 (1994).
Klockenbusch et al., "Platelet PGI2 receptor affinity is reduced in pre-eclampsia," Br J Clin Pharmacol. 41(6):616-8 (1996).
Koga et al., "Elevated serum soluble vascular endothelial growth factor receptor 1 (sVEGFR-1) levels in women with preeclampsia," J Clin Endocrinol Metab. 88(5):2348-51 (2003).
Koos, "Management of Uncorrected, Palliated, and Repaired Cyanotic Congenital Heart Disease in Pregnancy," Progress in Pediatric Cardiology. 19:25-45 (2004).
Lain et al., "Contemporary concepts of the pathogenesis and management of preeclampsia," JAMA. 287(24):3183-6 (2002).
Lenasi et al., "Amlodipine activates the endothelial nitric oxide synthase by altering phosphorylation on Ser1177 and Thr495," Cardiovasc Res. 59(4):844-53 (2003).
Levine et al., "Circulating angiogenic factors and the risk of preeclampsia," N Engl J Med. 350(7):672-83 (2004).
Levine et al., "Trial of Calcium for Preeclampsia Prevention (CPEP): rationale, design, and methods," Control Clin Trials. 17(5):442-69 (1996).
Levine et al., "Two-stage elevation of cell-free fetal DNA in maternal sera before onset of preeclampsia," Am J Obstet Gynecol. 190(3):707-13 (2004).
Levine et al., "Urinary placental growth factor and risk of preeclampsia," JAMA. 293(1):77-85 (2005).
Li et al., "CD105 antagonizes the inhibitory signaling of transforming growth factor beta1 on human vascular endothelial cells," FASEB J. 14(1):55-64 (2000).
Li et al., "Immunodetection and characterisation of soluble CD105-TGFbeta complexes," J Immunol Methods. 218(1-2):85-93 (1998).
Li et al., "Plasma levels of soluble CD105 correlate with metastasis in patients with breast cancer," Int J Cancer. 89(2):122-6 (2000).
Li et al., "Role of transforming growth factor beta3 in lymphatic metastasis in breast cancer," Int J Cancer. 79(5):455-9 (1998).
Li et al., "The significance of CD105, TGFbeta and CD105/TGFbeta complexes in coronary artery disease," Atherosclerosis. 152(1):249-56 (2000).
Lim et al., "Human cytotrophoblast differentiation/invasion is abnormal in pre-eclampsia," Am J Pathol. 151(6):1809-18 (1997).
Livingston et al., "Placenta growth factor is not an early marker for the development of severe preeclampsia," Am J Obstet Gynecol. 184(6):1218-20 (2001).
Livingston et al., "Reductions of vascular endothelial growth factor and placental growth factor concentrations in severe preeclampsia," Am J Obstet Gynecol. 183(6):1554-7 (2000).
Luttun et al., "Soluble VEGF receptor Flt1: the elusive preeclampsia factor discovered?" J Clin Invest. 111(5):600-2 (2003).
Makondo et al., "Hepatocyte growth factor activates endothelial nitric oxide synthase by Ca(2+)-and phosphoinositide 3-kinase/Akt-dependent phosphorylation in aortic endothelial cells," Biochem J. 374(Pt 1):63-9 (2003).
Massagué et al., "The TGF-beta family and its composite receptors," Trends Cell Biol. 4(5):172-8. (1994).
Massagué, "TGF-beta signal transduction," Annu Rev Biochem. 67:753-91 (1998).
Masuda et al., "Vascular endothelial growth factor enhances glomerular capillary repair and accelerates resolution of experimentally induced glomerulonephritis," Am J Pathol. 159(2):599-608 (2001).
Maynard et al., "Excess placental soluble fms-like tyrosine kinase 1 (sFlt1) may contribute to endothelial dysfunction, hypertension, and proteinuria in preeclampsia," J Clin Invest. 111(5):649-58 (2003).
McAllister et al., "Endoglin, a TGF-beta binding protein of endothelial cells, is the gene for hereditary haemorrhagic telangiectasia type 1," Nat Genet. 8(4):345-51 (1994).
Mills et al., "Prostacyclin and thromboxane changes predating clinical onset of preeclampsia: a multicenter prospective study," JAMA. 282(4):356-62 (1999).
Miyazono et al., "Divergence and convergence of TGF-beta/BMP signaling," J Cell Physiol. 187(3):265-76 (2001).
Miyazono, "Positive and negative regulation of TGF-beta signaling," J Cell Sci. 113 (Pt 7):1101-9 (2000).
Miyazono et al., "TGF-β signaling system and its importance," Atsushi Miyajima (ed.), *Wakaru Jikken Igaku Series,* Cytokine from basic to latest topics, Yodosha Co., Ltd., 49-57 (2002).
Morbidelli et al., "Nitric oxide mediates mitogenic effect of VEGF on coronary venular endothelium," Am J Physiol. 270(1 Pt 2):H411-5 (1996).
Mordel et al., "Successful full-term pregnancy in familial Mediterranean fever complicated with amyloidosis: case report and review of the literature," Fetal Diagn Ther. 8(2):129-34 (1993).
Mortensen et al., "Smoking, sex of the offspring, and risk of placental abruption, placenta previa, and preeclampsia: a population-based cohort study," Acta Obstet Gynecol Scand. 80(10):894-8 (2001).
Myatt et al., "Endothelial nitric oxide synthase in placental villous tissue from normal, pre-eclamptic and intrauterine growth restricted pregnancies," Hum Reprod. 12(1):167-72 (1997).
Myers et al., "Hypertensive diseases and eclampsia," Curr Opin Obstet Gynecol. 14(2):119-25 (2002).

(56) References Cited

OTHER PUBLICATIONS

Neufeld et al., "Similarities and differences between the vascular endothelial growth factor (VEGF) splice variants," Cancer Metastasis Rev. 15(2):153-8 (1996).
Newman et al., "Cigarette smoking and pre-eclampsia: their association and effects on clinical outcomes," J Matern Fetal Med. 10(3):166-70 (2001).
Nohe et al., "Signal transduction of bone morphogenetic protein receptors," Cell Signal. 16(3):291-9 (2004).
Ong et al., "First-trimester maternal serum levels of placenta growth factor as predictor of preeclampsia and fetal growth restriction," Obstet Gynecol. 98(4):608-11 (2001).
Ostendorf et al., "VEGF(165) mediates glomerular endothelial repair," J Clin Invest. 104(7):913-23 (1999).
Oswald et al., "Mesenchymal stem cells can be differentiated into endothelial cells in vitro," Stem Cells. 22(3):377-84 (2004).
Ota et al., "Targets of transcriptional regulation by two distinct type I receptors for transforming growth factor-beta in human umbilical vein endothelial cells," J Cell Physiol. 193(3):299-318 (2002).
Page et al., "Excessive placental secretion of neurokinin B during the third trimester causes pre-eclampsia," Nature. 405(6788):797-800 (2000).
Papapetropoulos et al., "Vanadate is a potent activator of endothelial nitric-oxide synthase: evidence for the role of the serine/threonine kinase Akt and the 90-kDa heat shock protein," Mol Pharmacol. 65(2):407-15 (2004).
Paternoster et al., "Markers of tubular damage in pre-eclampsia," Minerva Ginecol. 51(10):373-7 (1999).
Polliotti et al., "Second-trimester maternal serum placental growth factor and vascular endothelial growth factor for predicting severe, early-onset preeclampsia," Obstet Gynecol. 101(6):1266-74 (2003).
Raab et al., "Expression of normal and truncated forms of human endoglin," Biochem J. 339(Pt 3):579-88 (1999).
Regnault et al., "Placental expression of VEGF, PlGF and their receptors in a model of placental insufficiency-intrauterine growth restriction (PI-IUGR)," Placenta. 23(2-3):132-44 (2002).
Roberts et al., "Pathogenesis and genetics of pre-eclampsia," Lancet. 357(9249):53-6 (2001).
Roes et al., "High levels of urinary vascular endothelial growth factor in women with severe preeclampsia," Int J Biol Markers. 19(1):72-5 (2004).
Sato et al., "Increased pulmonary vascular contraction to serotonin after cardiopulmonary bypass: role of cyclooxygenase," J Surg Res. 90(2):138-43 (2000).
Schultze-Mosgau et al., "Improved free vascular graft survival in an irradiated surgical site following topical application of rVEGF," Int J Radiat Oncol Biol Phys. 57(3):803-12 (2003).
Sibai et al., "What we have learned about preeclampsia," Semin Perinatol. 27(3):239-46 (2003).
Sibai, "Diagnosis and management of gestational hypertension and preeclampsia," Obstet Gynecol. 102(1):181-92 (2003).
Sporn et al., "Transforming growth factor-beta: recent progress and new challenges," J Cell Biol. 119(5):1017-21 (1992).
Strevens et al., "Glomerular endotheliosis in normal pregnancy and pre-eclampsia," BJOG. 110(9):831-6 (2003).
Su et al., "Decreased maternal serum placenta growth factor in early second trimester and preeclampsia," Obstet Gynecol. 97(6):898-904 (2001).
Sugimoto et al., "Neutralization of circulating vascular endothelial growth factor (VEGF) by anti-VEGF antibodies and soluble VEGF receptor 1 (sFlt-1) induces proteinuria," J Biol Chem. 278(15):12605-8 (2003).
Sánchez et al., "Quercetin downregulates NADPH oxidase, increases eNOS activity and prevents endothelial dysfunction in spontaneously hypertensive rats," J Hypertens. 24(1):75-84 (2006).
Thadhani et al., "First trimester placental growth factor and soluble fms-like tyrosine kinase 1 and risk for preeclampsia," J Clin Endocrinol Metab. 89(2):770-5 (2004).

Tai et al., "Endothelial nitric oxide synthase: a new paradigm for gene regulation in the injured blood vessel," Arterioscler Thromb Vasc Biol. 24(3):405-12 (2004).
Takahashi et al., "Antiangiogenic therapy of established tumors in human skin/severe combined immunodeficiency mouse chimeras by anti-endoglin (CD105) monoclonal antibodies, and synergy between anti-endoglin antibody and cyclophosphamide," Cancer Res. 61(21):7846-54 (2001).
Taylor et al., "Longitudinal serum concentrations of placental growth factor: evidence for abnormal placental angiogenesis in pathologic pregnancies," Am J Obstet Gynecol. 188(1):177-82 (2003).
Tidwell et al., "Low maternal serum levels of placenta growth factor as an antecedent of clinical preeclampsia," Am J Obstet Gynecol. 184(6):1267-72 (2001).
Tjoa et al., "Plasma placenta growth factor levels in midtrimester pregnancies," Obstet Gynecol. 98(4):600-7 (2001).
Torry et al., "Expression and function of placenta growth factor: implications for abnormal placentation," J Soc Gynecol Investig. 10(4):178-88 (2003).
Torry et al., "Preeclampsia is associated with reduced serum levels of placenta growth factor," Am J Obstet Gynecol. 179(6 Pt 1):1539-44 (1998).
Tucci et al., "rhVEGF and experimental rat skin flaps: systemic or local administration and morphological characteristics," Int J Artif Organs. 24(10):743-51 (2001).
UniProt Database Accession No. P17813. Retrieved from <http://www.uniprot.org/uniprot/P17813> on Jul. 7, 2011 (5 pages).
Velasco-Loyden et al., "The shedding of betaglycan is regulated by pervanadate and mediated by membrane type matrix metalloprotease-1," J Biol Chem. 279(9):7721-33 (2004).
Vuorela et al., "Amniotic fluid—soluble vascular endothelial growth factor receptor-1 in preeclampsia," Obstet Gynecol. 95(3):353-7 (2000).
Walker, "Pre-eclampsia," Lancet. 356(9237):1260-5 (2000).
Whittaker et al., "Matrix Metalloproteinases and Their Inhibitors-Current Status and Future Challenges," Cell Transmissions 17:3-12 (2001).
Yamashita et al., "Endoglin forms a heteromeric complex with the signaling receptors for transforming growth factor-beta," J Biol Chem. 269(3):1995-2001 (1994).
Zhou et al., "Preeclampsia is associated with failure of human cytotrophoblasts to mimic a vascular adhesion phenotype. One cause of defective endovascular invasion in this syndrome?" J Clin Invest. 99(9):2152-64 (1997).
Zhou et al., "Vascular endothelial growth factor ligands and receptors that regulate human cytotrophoblast survival are dysregulated in severe preeclampsia and hemolysis, elevated liver enzymes, and low platelets syndrome," Am J Pathol. 160(4):1405-23 (2002).
Canadian Office Action for Canadian Patent Application No. 2,581,336, dated Dec. 19, 2013 (4 pages).
Canadian Office Action for Canadian Patent Application No. 2,654,283, dated Dec. 16, 2013 (5 pages).
English translation of Chinese Office Action for Application No. 200580040164.6, dated Apr. 1, 2012 (8 pages).
English Translation of First Office Action for Chinese Patent Application No. 200580040164.6, dated Jan. 19, 2011 (11 pages).
Examination Report for Australian Patent Application No. 2005286626, dated Jan. 24, 2011 (3 pages).
Examination Report for European Patent Application No. 05815390.9, dated Mar. 20, 2009 (3 pages).
Extended European Search Report for European Patent Application No. 05815390.9, dated Jun. 11, 2008 (11 pages).
Extended European Search Report for European Patent Application No. 10186892.5, dated Jun. 29, 2011 (8 pages).
International Search Report for International Patent Application No. PCT/SG2005/000265, dated Sep. 26, 2005 (3 pages).
International Search Report for International Patent Application No. PCT/US03/22892, dated Nov. 16, 2005 (5 pages).
International Search Report for International Patent Application No. PCT/US05/03884, dated Feb. 3, 2006 (3 pages).
International Search Report for International Patent Application No. PCT/US07/12787, dated Jan. 31, 2008 (1 page).

(56) References Cited

OTHER PUBLICATIONS

Office Action for Canadian Patent Application No. 2581336, dated Jan. 12, 2012 (4 pages).
Office Action for Ecuadorian Patent Application No. SP-07-7391, dated May 9, 2011 (6 pages).
Office Action for Indonesian Patent Application No. W-00200700960, dated Dec. 31, 2010 (5 pages).
Office Action for Japanese Patent Application No. 2007-533722, dated Oct. 3, 2011 (10 pages).
Office Action for Japanese Patent Application No. 2009-513263, dated Jul. 10, 2012 (12 pages).
Office Action for U.S. Appl. No. 11/443,920, dated Jan. 21, 2009 (9 pages).
Office Action for U.S. Appl. No. 11/443,920, dated Sep. 10, 2009 (11 pages).
Search Report and Written Opinion for Singaporean Patent Application No. 200905831-4, dated Aug. 8, 2012 (12 pages).
Singapore Written Opinion and Search Report for Application No. 200905831-4, dated Aug. 29, 2012 (13 pages).
Supplementary European Search Report for European Patent Application No. 05815390.9, dated Oct. 8, 2008 (6 pages).
Written Opinion for Singaporean Patent Application No. 200702085-2, dated Oct. 29, 2008 (17 pages).
Fonsatti et al., "Endoglin: an accessory component of the TGF-beta-binding receptor-complex with diagnostic, prognostic, and bioimmunotherapeutic potential in human malignancies," J Cell Physiol. 188(1):1-7 (2001).
Non-Final Office Action for U.S. Appl. No. 15/279,102, dated Sep. 14, 2018 (29 pages).
Office Action for Canadian Application No. 2,581,336, dated Sep. 6, 2018 (5 pages).
"Endoglin (H-300) Antibody | Santa Cruz Biotechnology sc-20632 product information" Labome, <https://www.labome.com/product/santa-cruz-biotechnology/sc-20632.html>, retrieved on Apr. 8, 2019 (2 pages).
"Endoglin (P4A4): sc-20072" Santa Cruz Biotechnology, <https://datasheets.scbt.com/sc-20072.pdf>, retrieved on Apr. 8, 2019 (1 page).
"Quantikine Elisa Human Endoglin/CD105 Immunoassay, Catalog No. DNDG00" R&D Systems, Inc., <https://resources.rndsystems.com/pdfs/datasheets/dndg00.pdf>, retrieved on Apr. 8, 2019 (16 pages).
Edwards et al., "The remarkable flexibility of the human antibody repertoire; isolation of over one thousand different antibodies to a single protein, BLyS," J Mol Biol. 334(1):103-18 (2003).
Goel et al., "Plasticity within the antigen-combining site may manifest as molecular mimicry in the humoral immune response," J Immunol. 173(12):7358-67 (2004).
Lloyd et al., "Modelling the human immune response: performance of a 1011 human antibody repertoire against a broad panel of therapeutically relevant antigens," Protein Eng Des Sel. 22(3):159-68 (2009).
Luque et al., "The use of recombinant vaccinia virus to generate monoclonal antibodies against the cell-surface glycoprotein endoglin," FEBS Lett. 413(2):265-8 (1997).

\* cited by examiner

FIGURE 2A. Predicted cDNA sequence of soluble endoglin (437 amino acids):

```
   1 atggaccgcg gcacgctccc tctggctgtt gccctgctgc tggccagctg cagcctcagc
  61 cccacaagtc ttgcagaaac agtccattgt gaccttcagc ctgtgggccc cgagagggac
 121 gaggtgacat ataccactag ccaggtctcg aagggctgcg tggctcaggc ccccaatgcc
 181 atccttgaag tccatgtcct cttcctggag ttcccaacgg ccccgtcaca gctggagctg
 241 actctccagg catccaagca aaatggcacc tggccccgag aggtgcttct ggtcctcagt
 301 gtaaacagca gtgtcttcct gcatctccag gccctgggaa tcccactgca cttggcctac
 361 aattccagcc tggtcacctt ccaagagccc ccggggtca acaccacaga gctgccatcc
 421 ttccccaaga cccagatcct tgagtgggca gctgagaggg gccccatcac ctctgctgct
 481 gagctgaatg acccccagag catcctcctc cgactgggcc aagcccaggg gtcactgtcc
 541 ttctgcatgc tggaagccag ccaggacatg ggccgcacgc tcgagtggcg gccgcgtact
 601 ccagccttgg tccggggctg ccacttggaa ggcgtggccg gccacaagga ggcgcacatc
 661 ctgagggtcc tgccgggcca ctcggccggg ccccggacgg tgacggtgaa ggtggaactg
 721 agctgcgcac ccggggatct cgatgccgtc ctcatcctgc agggtcccc ctacgtgtcc
 781 tggctcatcg acgccaacca caacatgcag atctggacca ctggagaata ctccttcaag
 841 atctttccag agaaaaacat tcgtggcttc aagctcccag acacacctca aggcctcctg
 901 ggggaggccc ggatgctcaa tgccagcatt gtggcatcct tcgtggagct acccgctggcc
 961 agcattgtct cacttcatgc ctccagctgc ggtggtaggc tgcagacctc acccgcaccg
1021 atccagacca ctcctcccaa ggacacttgt agcccggagc tgctcatgtc cttgatccag
1081 acaaagtgtg ccgacgacgc catgaccctg gtactaaaga aagagcttgt tgcgcatttg
1141 aagtgcacca tcacgggcct gaccttctgg gacccagct gtgaggcaga ggacaggggt
1201 gacaagtttg tcttgcgcag tgcttactcc agctgtggca tgcaggtgtc agcaagtatg
1261 atcagcaatg aggcggtggt caatatcctg tcgagctcat caccacagcg g
```

FIGURE 2B. Predicted protein sequence:

Met D R G T L P L A V A L L L A S C S L S P T S L A E T V H C D L Q P V G P E R G E V
T Y T T S Q V S K G C V A Q A P N A I L E V H V L F L E F P T G P S Q L E L T L Q A S
K Q N G T W P R E V L L V L S V N S S V F L H L Q A L G I P L H L A Y N S S L V T F Q
E P P G V N T T E L P S F P K T Q I L E W A A E R G P I T S A A E L N D P Q S I L L R L
G Q A Q G S L S F C Met L E A S Q D Met G R T L E W R P R T P A L V R G C H L E G V
A G H K E A H I L R V L P G H S A G P R T V T V K V E L S C A P G D L D A V L I L Q G
P P Y V S W L I D A N H N Met Q I W T T G E Y S F K I F P E K N I R G F K L P D T P Q G
L L G E A R Met L N A S I V A S F V E L P L A S I V S L H A S S C G G R L Q T S P A P I
Q T T P P K D T C S P E L L Met S L I Q T K C A D D A Met T L V L K K E L V A H L K C
T I T G L T F W D P S C E A E D R G D K F V L R S A Y S S C G Met Q V S A S Met I S N
E A V V N I L S S S S P Q R

Double Immunofluorescence Staining of Endoglin and Smooth Muscle Actin (SMA)
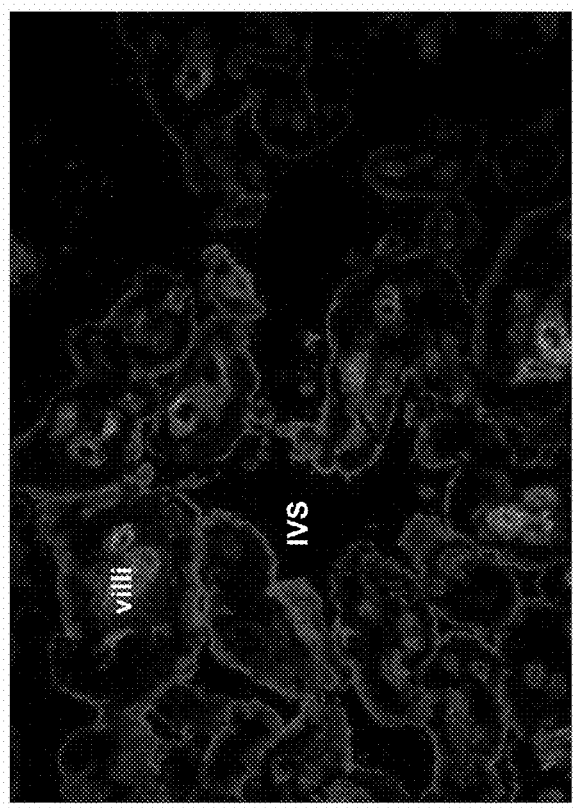
Preeclampsia, 25.2wks GA, x200
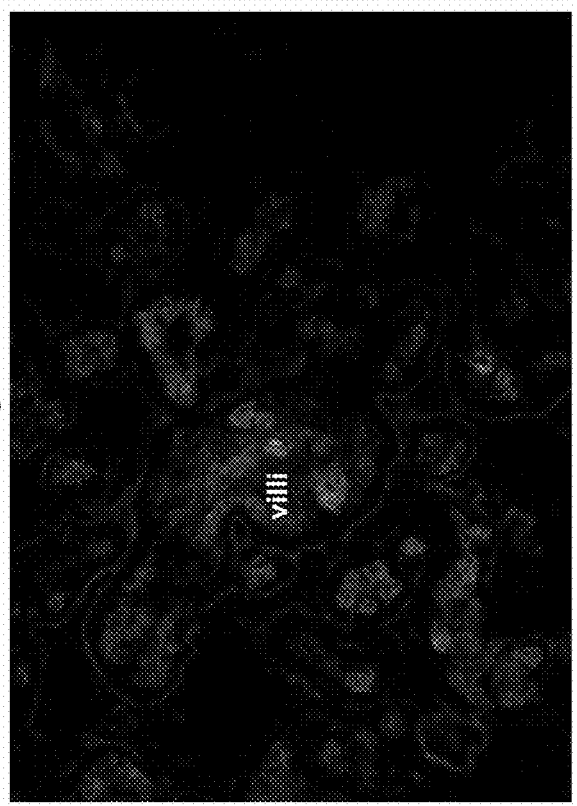
Preterm Labor/Delivery, 25.6wks GA, x200
Green: SMA, Red: Endoglin
Figure 19

SEQUENCE LISTING

```
<160> NUMBER OF SEQ ID NOS: 4

<210> SEQ ID NO 1
<211> LENGTH: 1311
<212> TYPE: DNA
<213> ORGANISM: Homo sapiens

<400> SEQUENCE: 1
atggaccgcg gcacgctccc tctggctgtt gccctgctgc tggccagctg cagcctcagc      60
cccacaagtc ttgcagaaac agtccattgt gaccttcagc ctgtgggccc cgagagggac     120
gaggtgacat ataccactag ccaggtctcg aagggctgcg tggctcaggc ccccaatgcc     180
atccttgaag tccatgtcct cttcctggag ttcccaacgg gcccgtcaca gctggagctg     240
actctccagg catccaagca aaatggcacc tggccccgag aggtgcttct ggtcctcagt     300
gtaaacagca gtgtcttcct gcatctccag gccctgggaa tcccactgca cttggcctac     360
aattccagcc tggtcacctt ccaagagccc cggggtca acaccacaga gctgccatcc     420
ttccccaaga cccagatcct tgagtgggca gctgagaggg gccccatcac ctctgctgct     480
gagctgaatg acccccagag catcctcctc cgactgggcg aagcccaggg gtcactgtcc     540
ttctgcatgc tggaagccag ccaggacatg ggccgcacgc tcgagtggcg gccgcgtact     600
ccagccttgg tccggggctg ccacttggaa ggcgtggccg ccacaagga ggcgcacatc     660 ctgagggtcc tgccgggcca ctcggccggg ccccggacgg tgacggtgaa ggtggaactg     720
agctgcgcac ccggggatct cgatgccgtc ctcatcctgc agggtccccc ctacgtgtcc     780
tggctcatcg acgccaacca caacatgcag atctggacca ctggagaata ctccttcaag     840 atcttttccag agaaaaacat tcgtggcttc aagctcccag acacacctca aggcctcctg     900
ggggaggccc ggatgctcaa tgccagcatt gtggcatcct tcgtggagct accgctggcc     960
agcattgtct cacttcatgc ctccagctgc ggtggtaggc tgcagacctc acccgcaccg    1020
atccagacca ctcctcccaa ggacacttgt agcccggagc tgctcatgtc cttgatccag    1080
acaaagtgtg ccgacgacgc catgaccctg gtactaaaga aagagcttgt tgcgcatttg    1140
aagtgcacca tcacgggcct gaccttctgg gaccccagct gtgaggcaga ggacagggggt    1200 gacaagtttg tcttgcgcag tgcttactcc agctgtggca tgcaggtgtc agcaagtatg    1260
atcagcaatg aggcggtggt caatatcctg tcgagctcat caccacagcg g            1311

<210> SEQ ID NO 2
<211> LENGTH: 437
<212> TYPE: PRT
<213> ORGANISM: Homo sapiens

<400> SEQUENCE: 2

Met Asp Arg Gly Thr Leu Pro Leu Ala Val Ala Leu Leu Leu Ala Ser
1               5                   10                  15

Cys Ser Leu Ser Pro Thr Ser Leu Ala Glu Thr Val His Cys Asp Leu
            20                  25                  30
```

```
Gln Pro Val Gly Pro Glu Arg Gly Glu Val Thr Tyr Thr Ser Gln
         35                  40                  45

Val Ser Lys Gly Cys Val Ala Gln Ala Pro Asn Ala Ile Leu Glu Val
 50                  55                  60

His Val Leu Phe Leu Glu Phe Pro Thr Gly Pro Ser Gln Leu Glu Leu
 65                  70                  75                  80

Thr Leu Gln Ala Ser Lys Gln Asn Gly Thr Trp Pro Arg Glu Val Leu
                 85                  90                  95

Leu Val Leu Ser Val Asn Ser Ser Val Phe Leu His Leu Gln Ala Leu
                100                 105                 110

Gly Ile Pro Leu His Leu Ala Tyr Asn Ser Ser Leu Val Thr Phe Gln
            115                 120                 125

Glu Pro Pro Gly Val Asn Thr Thr Glu Leu Pro Ser Phe Pro Lys Thr
        130                 135                 140

Gln Ile Leu Glu Trp Ala Ala Glu Arg Gly Pro Ile Thr Ser Ala Ala
145                 150                 155                 160

Glu Leu Asn Asp Pro Gln Ser Ile Leu Leu Arg Leu Gly Gln Ala Gln
                165                 170                 175

Gly Ser Leu Ser Phe Cys Met Leu Glu Ala Ser Gln Asp Met Gly Arg
            180                 185                 190

Thr Leu Glu Trp Arg Pro Arg Thr Pro Ala Leu Val Arg Gly Cys His
        195                 200                 205

Leu Glu Gly Val Ala Gly His Lys Glu Ala His Ile Leu Arg Val Leu
210                 215                 220

Pro Gly His Ser Ala Gly Pro Arg Thr Val Thr Val Lys Val Glu Leu
225                 230                 235                 240

Ser Cys Ala Pro Gly Asp Leu Asp Ala Val Leu Ile Leu Gln Gly Pro
                245                 250                 255

Pro Tyr Val Ser Trp Leu Ile Asp Ala Asn His Asn Met Gln Ile Trp
            260                 265                 270

Thr Thr Gly Glu Tyr Ser Phe Lys Ile Phe Pro Glu Lys Asn Ile Arg
        275                 280                 285

Gly Phe Lys Leu Pro Asp Thr Pro Gln Gly Leu Leu Gly Glu Ala Arg
    290                 295                 300

Met Leu Asn Ala Ser Ile Val Ala Ser Phe Val Glu Leu Pro Leu Ala
305                 310                 315                 320

Ser Ile Val Ser Leu His Ala Ser Ser Cys Gly Gly Arg Leu Gln Thr
                325                 330                 335

Ser Pro Ala Pro Ile Gln Thr Thr Pro Pro Lys Asp Thr Cys Ser Pro
            340                 345                 350

Glu Leu Leu Met Ser Leu Ile Gln Thr Lys Cys Ala Asp Asp Ala Met
        355                 360                 365

Thr Leu Val Leu Lys Lys Glu Leu Val Ala His Leu Lys Cys Thr Ile
    370                 375                 380

Thr Gly Leu Thr Phe Trp Asp Pro Ser Cys Glu Ala Glu Asp Arg Gly
385                 390                 395                 400

Asp Lys Phe Val Leu Arg Ser Ala Tyr Ser Ser Cys Gly Met Gln Val
                405                 410                 415

Ser Ala Ser Met Ile Ser Asn Glu Ala Val Val Asn Ile Leu Ser Ser
            420                 425                 430

Ser Ser Pro Gln Arg
            435
```

```
<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
acgaagcttg aaacagtcca ttgtgacctt                                        30

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
ttagatatct ggcctttgct tgtgcaacc                                         29
```

METHODS OF DIAGNOSING AND TREATING COMPLICATIONS OF PREGNANCY

CROSS-REFERENCE TO RELATED APPLICATIONS

This application is a continuation of U.S. patent application Ser. No. 11/235,577, filed Sep. 26, 2005, which claims the benefit of the filing date of U.S. provisional application No. 60/613,170, filed Sep. 24, 2004, both of which are herein incorporated by reference.

STATEMENT AS TO FEDERALLY SPONSORED RESEARCH

This invention was made in part with support from the Government through NIH Grant Nos. DK 064255 and HL 079594. The Government has certain rights in the invention.

REFERENCE TO A SEQUENCE LISTING

This application contains a Sequence Listing in computer readable form. The computer readable form is incorporated herein by reference.

FIELD OF THE INVENTION

In general, this invention relates to the detection and treatment of subjects having a pregnancy related hypertensive disorder.

BACKGROUND OF THE INVENTION

Pre-eclampsia is a syndrome of hypertension, edema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the 20$^{th}$ week of pregnancy and are usually detected by routine measuring of the woman's blood pressure and urine. However, these monitoring methods are ineffective for diagnosis of the syndrome at an early stage, which could reduce the risk to the subject or developing fetus, if an effective treatment were available.

Currently there are no known cures for pre-eclampsia. Pre-eclampsia can vary in severity from mild to life threatening. A mild form of pre-eclampsia can be treated with bed rest and frequent monitoring. For moderate to severe cases, hospitalization is recommended and blood pressure medication or anticonvulsant medications to prevent seizures are prescribed. If the condition becomes life threatening to the mother or the baby the pregnancy is terminated and the baby is delivered pre-term.

The proper development of the fetus and the placenta is mediated by several growth factors or angiogenic factors. One of these angiogenic factors is endoglin, also known as CD105. Endoglin is a homodimeric cell membrane glycoprotein that is predominantly expressed on endothelial cells such as syncytiotrophoblasts, human unbiblical vein endothelial cells (HUVEC), and on vascular endothelial cells. Endoglin shares sequence identity with betaglycan, a transforming growth factor (TGF)-β receptor type III. Endoglin has been shown to be a regulatory component of the TGF-β receptor complex, which modulates angiogenesis, proliferation, differentiation, and apoptosis. Endoglin also binds several other members of the TGF-β superfamily including activin-A, bone morphogenic protein (BMP)-2 and BMP-7. In particular, endoglin binds TGF-β1 and TGF-β3 with high affinity and forms heterotrimeric associations with the TGF-β signaling receptors types I and II. Mutations in the coding region of the endoglin gene are responsible for haemorrhagic telangiectasia type 1 (HHT1), a dominantly inherited vascular disorder characterized by multisystemic vascular dysplasia and recurrent hemorrhage. A soluble form of endoglin has also been identified and found to be present at increased levels in patients with metastatic breast and colorectal cancer; however, the exact functional role of the soluble endoglin in the pathogenesis of cancer is unclear. Soluble endoglin production has not been reported to be associated with pre-eclampsia or normal pregnancy.

Several factors have been reported to have an association with fetal and placental development and, more specifically, with pre-eclampsia. They include vascular endothelial growth factor (VEGF), soluble Flt-1 receptor (sFlt-1), and placental growth factor (PlGF). VEGF is an endothelial cell-specific mitogen, an angiogenic inducer, and a mediator of vascular permeability. VEGF has also been shown to be important for glomerular capillary repair. VEGF binds as a homodimer to one of two homologous membrane-spanning tyrosine kinase receptors, the fms-like tyrosine kinase (Flt-1) and the kinase domain receptor (KDR), which are differentially expressed in endothelial cells obtained from many different tissues. Flt-1, but not KDR, is highly expressed by trophoblast cells which contribute to placental formation. PlGF is a VEGF family member that is also involved in placental development. PlGF is expressed by cytotrophoblasts and syncytiotrophoblasts and is capable of inducing proliferation, migration, and activation of endothelial cells. PlGF binds as a homodimer to the Flt-1 receptor, but not the KDR receptor. Both PlGF and VEGF contribute to the mitogenic activity and angiogenesis that are critical for the developing placenta.

sFlt-1, which lacks the transmembrane and cytoplasmic domains of the receptor, was recently identified in a cultured medium of human umbilical vein endothelial cells and in vivo expression was subsequently demonstrated in placental tissue. sFlt-1 binds to VEGF with a high affinity but does not stimulate mitogenesis of endothelial cells.

Careful regulation of angiogenic and mitogenic signaling pathways is critical for maintaining appropriate proliferation, migration, and angiogenesis by trophoblast cells in the developing placenta.

There is a need for methods of accurately diagnosing subjects at risk for or having pre-eclampsia or eclampsia, particularly before the onset of the most severe symptoms. A treatment is also needed.

SUMMARY OF THE INVENTION

We have discovered methods for diagnosing and treating pregnancy related hypertensive disorders, including pre-eclampsia and eclampsia.

Using gene expression analysis, we have discovered that levels of soluble endoglin (sE) are markedly elevated in placental tissue samples from pregnant women suffering from pregnancy complications associated with hypertension, including pre-eclampsia. Endoglin is a part of the TGF-β receptor complex that acts to regulate angiogenesis. Endoglin can bind with high affinity to TGF-β family members that are ligands for TGF-β receptors. In affected individuals, excess soluble endoglin may be depleting the placenta of necessary amounts of essential angiogenic and mitogenic factors. In the present invention, compounds that bind to or neutralize soluble endoglin are used to reduce the elevated levels of soluble endoglin. In addition, antibodies directed to soluble endoglin as well as RNA interference and antisense nucleobase oligomers directed to lowering the levels of biologically active soluble endoglin are also provided. Finally, the present invention provides for the measuring of soluble endoglin levels as a detection tool for early diagnosis and management of pregnancy related hypertensive disorders, including pre-eclampsia and eclampsia, or a predisposition thereto.

Accordingly, in one aspect, the invention provides a method of treating or preventing a pregnancy related hypertensive disorder, such as pre-eclampsia or eclampsia, in a subject by administering to the subject a compound capable of binding to soluble endoglin, where the administering is for a time and in an amount sufficient to treat or prevent at least one symptom of the pregnancy related hypertensive disorder in the subject. Non-limiting examples of pregnancy related hypertensive disorders include pre-eclampsia, eclampsia, gestational hypertension, chronic hypertension, HELLP syndrome, and pregnancy with a small for gestational age infant (SGA). In a preferred embodiment, the compound is a purified soluble endoglin antibody or antigen-binding fragment thereof that specifically binds to soluble endoglin. In another preferred embodiment, the compound is a growth factor, such as a TGF-β family member (e.g., TGF-β1, TGF-β3, activin-A, BMP-2, and BMP-7) or a fragment thereof capable of specifically binding soluble endoglin.

In another preferred embodiment, the method also includes administering a compound, such as a purified sFlt-1 antibody, a sFlt-1 antigen-binding fragment, nicotine, theophylline, adenosine, nifedipine, minoxidil, magnesium sulfate, vascular endothelial growth factor (VEGF), including all isoforms such as VEGF189, VEGF121, VEGF165, or fragments thereof or placental growth factor (PlGF), including all isoforms and fragments thereof, where the administering is for a time and in an amount sufficient to treat or prevent the pregnancy related hypertensive disorder in a subject.

In another aspect, the invention features a method of treating or preventing a pregnancy related hypertensive disorder, such as pre-eclampsia or eclampsia, in a subject by administering to the subject a compound (e.g., chemical compound, polypeptide, peptide, antibody, or a fragment thereof) that increases the level of a growth factor capable of binding to soluble endoglin. The compound is administered for a time and in an amount sufficient to treat or prevent the pregnancy related hypertensive disorder. In preferred embodiments, the compound increases the level of a TGF-β family member (e.g., TGF-β1, TGF-β3, activin-A, BMP-2, and BMP-7) and fragments thereof. Non-limiting examples of such compounds include cyclosporine, alpha tocopherol, methysergide, bromocriptine, and aldomet.

In another related aspect, the invention features a method of treating or preventing a pregnancy related hypertensive disorder in a subject by administering to the subject a compound (e.g., chemical compound, polypeptide, peptide, antibody, or a fragment thereof) that inhibits growth factor binding to a soluble endoglin polypeptide. The compound is administered for a time and in an amount sufficient to treat or prevent pregnancy related hypertensive disorder. In preferred embodiments, the compound binds to soluble endoglin and prevents growth factor binding. Non-limiting examples of such compounds include antibodies and small-molecule compounds obtained through screening.

In another aspect, the invention provides a method of treating or preventing a pregnancy related hypertensive disorder, such as pre-eclampsia or eclampsia, in a subject by administering to the subject a compound capable of reducing soluble endoglin expression or biological activity, where the administering is sufficient to treat or prevent the pregnancy related hypertensive disorder in the subject. In preferred embodiments, the compound is a purified antibody or antigen binding fragment thereof or a compound that inhibits the enzymatic activity of a proteolytic enzyme selected from the group consisting of: a matrix metalloproteinase (MMP), a cathepsin, or an elastase. MMPs include any one of MMP 1-26, preferably MMP9 or membrane-type MMP1.

Desirably, the compound capable of inhibiting the biological activity of soluble endoglin is identified by its ability to inhibit the angiogenic activity of endoglin as measured by an angiogenesis assay. In one example of such an assay, serum from a pre-eclamptic patient is used in a matrigel tube formation assay to induce an anti-angiogenic state. The compound is then added and a reduction in the anti-angiogenic state by 10%, 20%, 30%, 40%, 50%, 60%, 70%, 80%, 90% or more is indicative of a therapeutically effective compound.

The compound capable of inhibiting the biological activity of soluble endoglin can be an antisense nucleobase oligomer having at least one strand that is at least 80%, preferably 85%, 90%, 95%, 99%, or 100% complementary to at least a portion of the sequence of soluble endoglin. In one embodiment, the antisense nucleobase oligomer is complementary to at least 8, 10, preferably 20, 30, 40, 50, 60, 70, 80, 90, 100, or more consecutive nucleotides of soluble endoglin and can reduce or inhibit the expression or biological activity of soluble endoglin. Desirably, the antisense nucleobase oligomer is 8 to 30 nucleotides in length.

The compound capable of inhibiting the biological activity of soluble endoglin can also be a double stranded RNA (dsRNA) molecule having at least one strand that is at least 80%, preferably 85%, 90%, 95%, 99%, or 100% complementary to at least a portion of the sequence of a soluble endoglin nucleic acid molecule. In one embodiment, the double stranded RNA is a small interfering RNA (siRNA) that is 19 to 25 nucleotides in length and can reduce or inhibit the expression or biological activity of soluble endoglin. In additional preferred embodiments, the dsRNA has 100% nucleic acid identity to at least 18, preferably 19, 20, 21, 22, 23, 24, 25, 35, 45, 50 or more consecutive nucleotides of the nucleic acid sequence of a soluble endoglin molecule. Desirably, the dsRNA is an siRNA.

In various embodiments of any of the above aspects, the method further involves the step of administering to a subject an anti-hypertensive compound (e.g., adenosine, nifedipine, minoxidil, and magnesium sulfate). In other embodiments of the above aspects, the subject is a pregnant human, a post-partum human, a non-pregnant human, or a non-human (e.g., a cow, a horse, a sheep, a pig, a goat, a dog, or a cat). The therapeutic methods of the invention can be used to treat or prevent a pregnancy related hypertensive disorder that includes pre-eclampsia, eclampsia, gestational hypertension, chronic hypertension, HELLP syndrome, and pregnancy with an SGA infant. Preferred disorders are pre-eclampsia and eclampsia. In various embodiments of the above aspects, the method can be combined with the diagnostic methods of the invention, described below, to monitor the subject during therapy or to determine effective therapeutic dosages.

Any of the therapeutic aspects of the invention can also include administering one ore more additional compounds, such as a purified sFlt-1 antibody, a sFlt-1 antigen-binding fragment, nicotine, theophylline, adenosine, nifedipine, minoxidil, magnesium sulfate, vascular endothelial growth factor (VEGF), including all isoforms such as VEGF189, VEGF121, or VEGF165, or fragments thereof; placental growth factor (PlGF), including all isoforms and fragments thereof, where the administering is for a time and in an amount sufficient to treat or prevent pre-eclampsia or eclampsia in a subject. Preferred examples of such compounds are described in U.S. Patent Application Publication Numbers 20040126828 and 20050025762 and PCT Publication Number WO 2004/008946. Desirably, the compound will be a compound capable of binding to sFlt-1 or decreasing sFlt-1 expression.

Any of the therapeutic aspects of the invention can be used alone or in combination with one or more additional methods of the invention. In one example, an MMP inhibitor and an antibody can be used in combination to neutralize the soluble endoglin that is present and to block the further production of soluble endoglin by cleavage of the membrane bound form.

In another aspect, the invention features a purified antibody or antigen-binding fragment thereof that specifically binds soluble endoglin. In one preferred embodiment, the antibody prevents binding of a growth factor (e.g., TGF-β1, TGF-β3, activin-A, BMP-2, and BMP-7) to soluble endoglin. In another embodiment, the antibody is a monoclonal antibody. In other preferred embodiments, the antibody or antigen-binding fragment thereof is a human or humanized antibody. In other embodiments, the antibody lacks an Fc portion. In still other embodiments, the antibody is an $F(ab')_2$, an Fab, or an Fv structure. In other embodiments, the antibody or antigen-binding fragment thereof is present in a pharmaceutically acceptable carrier.

In another aspect, the invention provides a method of diagnosing a subject as having, or having a predisposition to, a pregnancy related hypertensive disorder, such as pre-eclampsia or eclampsia, involving measuring the level of soluble endoglin polypeptide in a sample from the subject. In preferred embodiments the level of soluble endoglin is the level of free, bound, or total soluble endoglin. In some embodiments, the level of soluble endoglin is the level of a soluble endoglin polypeptide resulting from degradation or enzymatic cleavage. The diagnosis of a pregnancy related hypertensive disorder or a predisposition to a pregnancy related hypertensive disorder can result from an alteration (e.g., an increase) in the relative level of soluble endoglin as compared to a normal reference sample or from the detection of an absolute level of soluble endoglin that is above a normal reference value. For example, normally, circulating serum or plasma concentrations of soluble endoglin range from 2-7 ng/ml during the non-pregnant state and from 10-20 ng/ml during normal pregnancy. For embodiments that include the measurement of the absolute levels of soluble endoglin, a level greater than 15 ng/ml, 20 ng/ml, or preferably greater than 25 ng/ml, is considered a diagnostic indicator of a pregnancy related hypertensive disorder, such as pre-eclampsia or eclampsia. In additional preferred embodiments, the method further includes measuring the level of at least one of sFlt-1, VEGF, or PlGF polypeptide in a sample from a subject as described in U.S. Patent Application Publication Numbers 20040126828, 20050025762, and 2005017044 and PCT Publication Numbers WO 2004/008946 and WO 2005/077007. The method can also include measuring the level of at least two of sFlt-1, VEGF, or PlGF polypeptide in a sample from a subject and calculating the relationship between the levels of sFlt-1, VEGF, or PlGF using a metric, where an alteration in the subject sample relative to a reference sample diagnoses a pregnancy related hypertensive disorder or a predisposition to a pregnancy related hypertensive disorder. In preferred embodiments, the method also includes determining the body mass index (BMI), the gestational age (GA) of the fetus, or both and including the BMI or GA or both in the metric. In one embodiment, the metric is a pre-eclampsia anti-angiogenic index (PAAI): [sFlt-1/VEGF+PlGF], where the PAAI is used as an indicator of anti-angiogenic activity. In one embodiment, a PAAI greater than 10, more preferably greater than 20, is indicative of pre-eclampsia or eclampsia. In another embodiment the metric is the following soluble endoglin anti-angiogenic index: (sFlt-1+0.25 (soluble endoglin polypeptide))/PlGF. An increase in the value of the soluble endoglin anti-angiogenic index is a diagnostic indicator of a pregnancy related hypertensive disorder, such as pre-eclampsia or eclampsia. For example a value above 75 during weeks 21-32 weeks or a value above 100 after weeks >32 weeks diagnoses a pregnancy related hypertensive disorder, such as pre-eclampsia or eclampsia. Another metric useful in the diagnostic methods of the invention is: (soluble endoglin+sFlt-1)/PlGF. Any of the methods can also include determining the body mass index (BMI), the gestational age (GA) of the fetus, or both and including the BMI or GA or both in the metric.

In various embodiments of the above aspects, the sample is a bodily fluid, such as urine, amniotic fluid, blood, serum, plasma, and cerebrospinal fluid. Desirably, the level of soluble endoglin, sFlt-1, VEGF, or PlGF polypeptide is determined by an immunological assay, such as an ELISA. In another example, a level of soluble endoglin greater than 20, preferably greater than 25 ng/ml, alone or in combination with increased sFlt-1 and decreased free PlGF or VEGF is used for the diagnosis of a pregnancy related hypertensive disorder, such as pre-eclampsia or eclampsia In one embodiment, an increase in the level of soluble endoglin is indicative of pre-eclampsia or eclampsia or the propensity to develop pre-eclampsia or eclampsia. In preferred embodiments of the above aspects, the level of sFlt-1 polypeptide measured is the level of free, bound, or total sFlt-1 polypeptide. In additional embodiments, the sFlt-1 polypeptide can also include sFlt-1 fragments, degradation products, or enzymatic cleavage products. In other preferred embodiments of the above aspects, the level of VEGF or PlGF is the level of free VEGF or PlGF.

In another aspect, the invention provides a method of diagnosing a subject as having, or having a predisposition to, pregnancy related hypertensive disorder, such as pre-eclampsia or eclampsia that includes measuring the level of an endoglin nucleic acid molecule (e.g., mRNA), preferably a soluble endoglin nucleic acid, in a sample from the subject and comparing it to a reference sample, where an alteration (e.g., an increase) in the levels relative to a reference sample (e.g., a normal reference) diagnoses a pregnancy related hypertensive disorder, such as pre-eclampsia or eclampsia, in the subject, or diagnoses a predisposition to pregnancy related hypertensive disorder, such as pre-eclampsia or eclampsia. In additional embodiments, the method can further include measuring the level of a sFlt-1, VEGF, or PlGF nucleic acid molecule (e.g., mRNA) in a sample from the subject and comparing it to a reference sample, where an alteration (e.g., a decrease in the level of VEGF or PlGF or an increase in the level of sFlt-1) in the levels relative to a normal reference sample diagnoses a pregnancy related hypertensive disorder, such as pre-eclampsia or eclampsia in the subject, or diagnoses a predisposition to a pregnancy related hypertensive disorder, such as pre-eclampsia or eclampsia.

In preferred embodiments of the above diagnostic aspects, the levels are measured on two or more occasions and a change in the levels between measurements is a diagnostic indicator of pregnancy related hypertensive disorder, such as pre-eclampsia or eclampsia. In one preferred embodiment, an increase (e.g., 10%, 20%, 30%, 40%, 50%, 60%, 70%, 80%, 90%, 95%, 96%, 97%, 98%, 99% or greater) in the level of soluble endoglin from the first measurement to the next measurement is used to diagnose pregnancy related hypertensive disorder, such as pre-eclampsia or eclampsia. In another embodiment of the above diagnostic aspects, the levels of soluble endoglin are compared to a normal reference sample and an increase (e.g., 10%, 20%, 30%, 40%, 50%, 60%, 70%, 80%, 90%, 95%, 96%, 97%, 98%, 99% or greater) in the level of soluble endoglin as compared to a normal reference sample is indicative of pre-eclampsia or eclampsia.

In another aspect, the invention provides a method of diagnosing a subject as having, or having a predisposition to, a pregnancy related hypertensive disorder, such as pre-eclampsia or eclampsia, that includes determining the nucleic acid sequence of an endoglin gene in a subject and comparing it to a reference sequence, where an alteration in the subject's nucleic acid sequence that changes the level or the biological activity of the gene product in the subject diagnoses the subject with a pregnancy related hypertensive disorder, or a predisposition to a pregnancy related hypertensive disorder. In one embodiment, the alteration is a polymorphism in the nucleic acid sequence. In another embodiment, the nucleic acid sequence of sFlt-1, VEGF, or PlGF, or any combination thereof, gene is also determined and compared to a reference sequence. An alteration in any one or more of these sequences that changes the level or the biological activity of the gene product in the subject diagnoses the subject with a pregnancy related hypertensive disorder.

In various embodiments of the above aspects, the sample is a bodily fluid (e.g., urine, amniotic fluid, blood, serum, plasma, or cerebrospinal fluid) of the subject in which the soluble endoglin and the sFlt-1, VEGF, or PlGF is normally detectable. In additional embodiments, the sample is a tissue or a cell (e.g., placental tissue or placental cells, endothelial cells, leukocytes, and monocytes). In other embodiments of the above aspects, the subject is a non-pregnant human, a pregnant human, or a post-partum human. In other embodiments of the above aspects, the subject is a non-human (e.g., a cow, a horse, a sheep, a pig, a goat, a dog, or a cat). In one embodiment, the subject is a non-pregnant or pregnant human and the method is used to diagnose a predisposition to pre-eclampsia or eclampsia. In additional embodiments, the BMI or GA or both is also measured. In various embodiments of the above aspects, an increase in the level of soluble endoglin nucleic acid or polypeptide relative to a reference is a diagnostic indicator of pre-eclampsia or eclampsia.

In another aspect, the invention provides a method of diagnosing a subject as having, or having a predisposition to, pregnancy related hypertensive disorder, such as pre-eclampsia or eclampsia that includes measuring the level of a soluble endoglin ligand, such as TGF-$\beta$1, TGF-$\beta$3, activin-A, BMP-2, and BMP-7 in a sample from a subject.

In various embodiments of any of the above diagnostic aspects, the pregnancy related hypertensive disorder is pre-eclampsia, eclampsia, gestational hypertension, chronic hypertension, HELLP syndrome, or pregnancy with an SGA infant. In any of the diagnostic aspects, the measuring of levels is done on two or more occasions and an increase in the levels between measurements us a diagnostic indicator of the pregnancy related hypertensive disorder. The diagnostic methods are desirable used to diagnose a pregnancy related hypertensive disorder prior to the onset of symptoms (e.g., at least 4, 5, 6, 7, 8, 9, or 10 weeks prior).

In another aspect, the invention provides a kit for the diagnosis of a pregnancy related hypertensive disorder, such as pre-eclampsia or eclampsia, in a subject comprising a nucleic acid sequence useful for detecting an endoglin nucleic acid, or fragment thereof, or a sequence complementary thereto. In a preferred embodiment, the nucleic acid sequence hybridizes, preferably at high stringency, to a nucleic acid encoding soluble endoglin, or a fragment thereof. In a preferred embodiment, the kit further comprises a nucleic acid sequence for detecting sFlt-1, VEGF, or PlGF.

In a related aspect, the invention provides a kit for the diagnosis of a pregnancy related hypertensive disorder, such as pre-eclampsia or eclampsia, in a subject that includes a soluble endoglin binding molecule (e.g., an antibody or antigen binding fragment thereof that specifically binds soluble endoglin). In one embodiment, the component is an immunological assay, an enzymatic assay, or a colorimetric assay. In other embodiments of the above aspects, the kit diagnoses a predisposition to pre-eclampsia or eclampsia in a pregnant or a non-pregnant subject. In preferred embodiments of the above aspects, the kit also includes a component for detecting sFlt-1, VEGF, or PlGF polypeptide. In additional preferred embodiments, the kit is used to detect soluble endoglin and to further detect VEGF, sFlt-1 and PlGF and determine a diagnostic ratio for the sample (e.g., PAAI or soluble endoglin anti-angiogenic index).

In preferred embodiments, the diagnostic kits include a label or instructions for the intended use of the kit components. In one embodiment, the diagnostic kit is labeled or includes instructions for use in the diagnosis of a pregnancy related hypertensive disorder, such as pre-eclampsia or eclampsia, or a predisposition to a pregnancy related hypertensive disorder, such as pre-eclampsia or eclampsia in a subject. In a preferred embodiment, the diagnostic kit includes a label or instructions for the use of the kit to determine the levels of soluble endoglin of the subject sample and to compare the soluble endoglin levels to a reference value. It will be understood that the reference values will depend on the intended use of the kit. For example, the sample can be compared to a normal soluble endoglin reference value, wherein an increase in the soluble endoglin levels is indicative of a pregnancy related hypertensive disorder, such as pre-eclampsia or eclampsia. The sample can also be compared to a reference that is a value or a sample from a subject known to have pre-eclampsia, wherein a decrease in the soluble endoglin levels is indicative of a pregnancy related hypertensive disorder, such as pre-eclampsia or eclampsia.

In a related aspect, the invention features a device for diagnosing a subject as having or having a predisposition to a pregnancy related hypertensive disorder, such as pre-eclampsia or eclampsia. by providing components for measuring and/or comparing the levels of soluble endoglin polypeptide or nucleic acid to a reference sample, wherein an alteration in the levels of soluble endoglin compared to a normal reference value diagnoses a pregnancy related hypertensive disorder, such as pre-eclampsia or eclampsia in the subject. In preferred embodiments, the device includes a membrane in a lateral flow or dipstick format used to measure and compare polypeptide levels in urine sample.

The device can also include components for comparing the levels of soluble endoglin and at least one of sFlt-1, VEGF, and PlGF nucleic acid molecules or polypeptides in a sample from a subject relative to a reference sample, wherein an alteration in the levels of soluble endoglin, and at least one of sFlt-1, VEGF, and PlGF nucleic acid molecules or polypeptides diagnoses pre-eclampsia or eclampsia or a predisposition to pre-eclampsia or eclampsia in the subject. In a preferred embodiment the device includes components for a metric to compare the levels of soluble endoglin, and at least one of sFlt-1, VEGF, and PlGF polypeptides.

Any of the diagnostic methods and kits described herein can also be used to monitor a subject already diagnosed as having or being at risk for having pre-eclampsia or eclampsia in order to monitor the subject during therapy or to determine effective therapeutic dosages. In one example, a kit used for therapeutic monitoring can have a reference soluble endoglin value that is indicative of pre-eclampsia or eclampsia, wherein a decrease in the soluble endoglin value of the subject sample relative to the reference sample can be used to indicate therapeutic efficacy or effective dosages of therapeutic compounds. In preferred embodiments, the kit is labeled or includes instructions for use in therapeutic monitoring or therapeutic dosage determination and the therapeutic compound can be included in the kit. The level of soluble endoglin protein or nucleic acid is measured alone or in combination with the levels of sFlt-1, VEGF, or PlGF protein or nucleic acids, or any combination thereof. In additional preferred embodiments, the level of soluble endoglin is compared to a reference sample that is indicative of a pregnancy related hypertensive disorder, such as pre-eclampsia or eclampsia, and an alteration (e.g., a decrease) in the levels of soluble endoglin relative to the reference sample is indicative of therapeutic efficacy or an effective dosage of a therapeutic compound. In one example, a decrease (e.g., 10%, 20%, 30%, 40%, 50%, 60%, 70%, 80%, 90% or more) in the level of soluble endoglin polypeptide or nucleic acid measured during or after administering therapy relative to the value before therapy is administered indicates an improvement in the pregnancy related hypertensive disorder. In another example, the absolute levels of soluble endoglin in the serum or plasma are measured and used for monitoring the therapeutic efficacy of that compound. For example, a therapeutic compound is preferably administered in a dose such that the level of soluble endoglin is less than 25 ng/ml, preferably less than 20 ng/ml.

In embodiments of the above therapeutic monitoring aspects that include the measurement of sFlt-1, a decrease in the level of sFlt-1 polypeptide or nucleic acid indicates an improvement in the pre-eclampsia or eclampsia. In another embodiment, a therapeutic compound is administered in a dose such that the level of sFlt-1 polypeptide is less than 2 ng/ml. In embodiments that include the measurement of VEGF or PlGF, an increase in the level of VEGF or PlGF polypeptide or nucleic acid measured during or after administering therapy relative to the value before therapy indicates an improvement in the pre-eclampsia or eclampsia. In embodiments that include the measurement of sFlt-1, VEGF, or PlGF in addition to the measurement of soluble endoglin, the method can include calculating the relationship between the levels of sFlt-1, VEGF, or PlGF using a metric, wherein an alteration in the relationship between said levels in the subject sample relative to a reference sample, is a diagnostic indicator of pre-eclampsia or eclampsia. On example of such a metric is the PAAI. In this example, a decrease in the PAAI value of a subject (e.g., less than 20, preferably less than 10) indicates an improvement in the pre-eclampsia or eclampsia. A decrease in the PAAI (e.g., less than 20, preferably less than 10) can also indicate an effective dosage of a therapeutic compound. Another example is the following soluble endoglin anti-angiogenic index, wherein an increase in the value is a diagnostic indicator of a pregnancy related hypertensive disorder, such as pre-eclampsia or eclampsia.

In preferred embodiments of the aspects relating to diagnosis or monitoring of therapeutic treatments, polypeptides are measured using an immunological assay such as ELISA or western blot. The level of soluble endoglin can be the level of free, bound (i.e., bound to a ligand), or total (i.e., free+bound) soluble endoglin, as well as the level of soluble endoglin resulting from degradation or enzymatic cleavage. For any of the monitoring methods, the measuring of levels can be done on two or more occasions and a change in the levels between measurements is a diagnostic indicator or pre-eclampsia or eclampsia.

In another aspect, the invention provides a method of identifying a compound that ameliorates a pregnancy related hypertensive disorder, such as pre-eclampsia or eclampsia, that involves contacting a cell that expresses an endoglin nucleic acid molecule with a candidate compound, and comparing the level of expression of the nucleic acid molecule in the cell contacted by the candidate compound with the level of expression in a control cell not contacted by the candidate compound, where an alteration in expression of the endoglin nucleic acid molecule identifies the candidate compound as a compound that may be useful to ameliorate a pregnancy related hypertensive disorder, such as pre-eclampsia or eclampsia.

In another aspect, the invention provides a method of identifying a compound that ameliorates a pregnancy related hypertensive disorder, such as pre-eclampsia or eclampsia, that involves contacting a cell that expresses a soluble endoglin polypeptide with a candidate compound, and comparing the level of expression of the polypeptide in the cell contacted by the candidate compound with the level of polypeptide expression in a control cell not contacted by the candidate compound, where an alteration in the expression of the soluble endoglin polypeptide identifies the candidate compound as a compound that may be useful to ameliorate the pregnancy related hypertensive disorder. In one embodiment, the alteration in expression is assayed using an immunological assay, an enzymatic assay, or an immunoassay. In one embodiment, the alteration in expression is a decrease in the level of soluble endoglin. The alteration in expression can result from an alteration in transcription or an alteration in translation.

In another aspect, the invention provides a method of identifying a compound that ameliorates a pregnancy related hypertensive disorder, such as pre-eclampsia or eclampsia, that involves contacting a cell that expresses a soluble endoglin polypeptide with a candidate compound, and comparing the biological activity of the soluble endoglin polypeptide in the cell contacted by the candidate compound with the level of biological activity in a control cell not contacted by the candidate compound, where an alteration in the biological activity of the soluble endoglin polypeptide identifies the candidate compound as a compound that ameliorates the pregnancy related hypertensive disorder. In one embodiment, the alteration is a decrease in the biological activity of soluble endoglin as assayed using an angiogenesis assay, a growth factor binding assay, or any of the assays described herein.

In another aspect, the invention provides a method of identifying a compound that ameliorates a pregnancy related hypertensive disorder, such as pre-eclampsia or eclampsia, comprising detecting binding of a soluble endoglin polypeptide and a candidate compound, where a compound that binds the soluble endoglin polypeptide may be useful to ameliorate a pregnancy related hypertensive disorder.

In another aspect, the invention provides a method of identifying a compound that ameliorates a pregnancy related hypertensive disorder, such as pre-eclampsia or eclampsia, that involves detecting binding between a soluble endoglin polypeptide and a growth factor in the presence of a candidate compound, where a decrease in the binding, relative to binding between the soluble endoglin polypeptide and the growth factor in the absence of the candidate compound identifies the candidate compound as a compound that may be useful to ameliorate the pregnancy related hypertensive disorder. In one embodiment, the growth factor is a TGF-β family member.

In another aspect, the invention provides a method of identifying a polypeptide that prevents binding between a soluble endoglin polypeptide and a growth factor. The method involves detecting binding between a soluble endoglin polypeptide and a growth factor in the presence of the candidate polypeptide, where a decrease in the binding, relative to binding between the soluble endoglin polypeptide and the growth factor in the absence of the candidate polypeptide identifies the candidate polypeptide as a polypeptide that prevents binding between a soluble endoglin polypeptide and a growth factor. In one embodiment, the growth factor is a TGF-β family member.

In a related aspect, the invention provides a compound identified according to the previous aspect, where the compound is a polypeptide that specifically binds a soluble endoglin polypeptide and prevents the soluble endoglin polypeptide from binding a TGF-β family member. In one preferred embodiment, the polypeptide is an antibody that binds soluble endoglin, preferably an antibody that specifically binds soluble endoglin.

While the methods described herein refer to pre-eclampsia and eclampsia specifically, it should be understood that the diagnostic and monitoring methods of the invention also apply to general complications of pregnancy associated with hypertension including but not limited to gestational hypertension, HELLP syndrome, and pregnancy with a small for gestational age (SGA) infant.

For the purpose of the present invention, the following abbreviations and terms are defined below.

By "alteration" is meant a change (increase or decrease) in the expression levels of a gene or polypeptide as detected by standard art known methods such as those described below. As used herein, an alteration includes a 10% change in expression levels, preferably a 25% change, more preferably a 40%, 50%, 60%, 70%, 80%, 90% or greater change in expression levels. "Alteration" can also indicate a change (increase or decrease) in the biological activity of any of the polypeptides of the invention (e.g., soluble endoglin, sFlt-1, VEGF, or PlGF). As used herein, an alteration includes a 10% change in biological activity, preferably a 25% change, more preferably a 40%, 50%, 60%, 70%, 80%, 90% or greater change in biological activity. Examples of biological activity for soluble endoglin are angiogenesis and binding assays using known ligands such as activin-A, BMP 2, BMP-7, TGF-β1 and TGF-β3. The biological activity of soluble endoglin can be measured by ligand binding assays, immunoassays, and angiogenesis assays that are standard in the art or are described herein. An example of such an assay is the in vitro matrigel endothelial tube formation assay in which antagonism of endoglin signaling led to massive loss of capillary formation (Li et al., *Faseb Journal* 14:55-64 (2000)). Other examples of biological activity for PlGF or VEGF include binding to receptors as measured by immunoassays, ligand binding assays or Scatchard plot analysis, and induction of cell proliferation or migration as measured by BrdU labeling, cell counting experiments, or quantitative assays for DNA synthesis such as $^3$H-thymidine incorporation. Examples of biological activity for sFlt-1 include binding to PlGF and VEGF as measured by immunoassays, ligand binding assays, or Scatchard plot analysis. Additional examples of assays for biological activity for each of the polypeptides are described herein.

By "antisense nucleobase oligomer" is meant a nucleobase oligomer, regardless of length, that is complementary to the coding strand or mRNA of an endoglin gene. By a "nucleobase oligomer" is meant a compound that includes a chain of at least eight nucleobases, preferably at least twelve, and most preferably at least sixteen bases, joined together by linkage groups. Included in this definition are natural and non-natural oligonucleotides, both modified and unmodified, as well as oligonucleotide mimetics such as Protein Nucleic Acids, locked nucleic acids, and arabino-nucleic acids. Numerous nucleobases and linkage groups may be employed in the nucleobase oligomers of the invention, including those described in U.S. Patent Publication Nos. 20030114412 (see for example paragraphs 27-45 of the publication) and 20030114407 (see for example paragraphs 35-52 of the publication), incorporated herein by reference. The nucleobase oligomer can also be targeted to the translational start and stop sites. Preferably the antisense nucleobase oligomer comprises from about 8 to 30 nucleotides. The antisense nucleobase oligomer can also contain at least 40, 60, 85, 120, or more consecutive nucleotides that are complementary to endoglin mRNA or DNA, and may be as long as the full-length mRNA or gene.

By "body mass index" is meant a number, derived by using height and weight measurements, that gives a general indication of whether or not weight falls within a healthy range. The formula generally used to determine the body mass index is a person's weight in kilograms divided by a person's height in meters squared or weight (kg)/(height (m))$^2$.

By "compound" is meant any small molecule chemical compound, antibody, nucleic acid molecule, or polypeptide, or fragments thereof. Compounds particularly useful for the therapeutic methods of the invention can alter, preferably decrease, the levels or biological activity of soluble endoglin by at least 10%, 20%, 30%, 40%, 50%, 60%, 70%, 80%, 90% or more.

By "chimeric antibody" is meant a polypeptide comprising at least the antigen-binding portion of an antibody molecule linked to at least part of another protein (typically an immunoglobulin constant domain).

By "double-stranded RNA (dsRNA)" is meant a ribonucleic acid molecule comprised of both a sense and an anti-sense strand. dsRNAs are typically used to mediate RNA interference.

By "endoglin," also known as CD105, is meant a mammalian growth factor that has endoglin biological activity (see Fonsatti et al., *Oncogene* 22:6557-6563, 2003; Fonsatti et al., *Curr. Cancer Drug Targets* 3:427-432, 2003) and is homologous to the protein defined by any of the following GenBank accession numbers: AAH29080 and NP_031958 (mouse); AAS67893 (rat); NP_000109, P17813, VSP_004233, and CAA80673 (human); and A49722 (pig), or described in U.S. Pat. No. 6,562,957. Endoglin is a homodimeric cell membrane glycoprotein which is expressed at high levels in proliferating vascular cells and syncytiotrophoblasts from placentas. There are two distinct isoforms of endoglin, L and S, which differ in their cytoplasmic tails by 47 amino acids. Both isoforms are included in the term endoglin as used herein. Endoglin binds to TGF-β family members and, in the presence of TGF-β, endoglin can associate with the TGF-β signaling receptors RI and RII, and potentiate the response to the growth factors. Endoglin biological activities include binding to TGF-β family members such as activin-A, BMP 2, BMP-7, TGF-β1 and TGF-β3; induction of angiogenesis, regulation of cell proliferation, attachment, migration, invasion; and activation of endothelial cells. Assays for endoglin biological activities are known in the art and include ligand binding assays or Scatchard plot analysis; BrdU labeling, cell counting experiments, or quantitative assays for DNA synthesis such as $^3$H-thymidine incorporation used to measure cell proliferation; and angiogenesis assays such as those described herein or in McCarty et al., *Intl. J. Oncol.* 21:5-10, 2002; Akhtar et al. *Clin. Chem.* 49:32-40, 2003; and Yamashita et al, *J. Biol. Chem.* 269:1995-2001, 1994). By "soluble endoglin" is meant any circulating, non-membrane bound form of endoglin which includes at least a part of the extracellular portion of the protein (see FIG. 1). Soluble endoglin can result from the cleavage of the membrane bound form of endoglin by a proteolytic enzyme. One potential cleavage site is at amino acid 437 producing a soluble endoglin polypeptide that includes amino acids 1-437 of the endoglin polypeptide (see FIGS. 2A and 2B). Although not wishing to be bound by theory, it is likely that the extracellular ligand binding domain retained by soluble endoglin would allow it to bind ligands such as TGF-β1 and TGF-β3, thereby creating a resulting deficiency in TGF-β. Furthermore, since endoglin is an endothelial-specific molecule, it is likely that the TGF-β deficiencies would be maximal in endothelial cells. Soluble endoglin can also include circulating degradation products or fragments that result from enzymatic cleavage of endoglin and that maintain endoglin biological activity. The biological function of soluble endoglin is unknown at the present time, but is predicted to create a deficiency of TGF-β and other known ligands. Soluble endoglin biological activity can be assayed by measuring the levels of free Activin A or free TGF-β3☐ or by using an angiogenesis assay known in the art or described herein.

By "endoglin nucleic acid" is meant a nucleic acid that encodes any of the endoglin proteins described above. For example, the gene for human endoglin consists of 14 exons, where exon 1 encodes the signal peptide sequence, exons 2-12 encode the extracellular domain, exon 13 encodes the transmembrane domain, and exon 14 encodes C-terminal cytoplasmic domain (see FIGS. 1, 2A, and 2B). Desirable, the endoglin nucleic acid encodes soluble endoglin (see FIG. 2A).

By "expression" is meant the detection of a gene or polypeptide by standard art known methods. For example, polypeptide expression is often detected by western blotting, DNA expression is often detected by Southern blotting or polymerase chain reaction (PCR), and RNA expression is often detected by northern blotting, PCR, or RNAse protection assays.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. Fragments may contain 10, 20, 30, 40, 50, 60, 70, 80, 90, or 100, 200, 300, 400, 500, 600, 700, 800, 900, or 1000 nucleotides or amino acids. Preferably, fragments of soluble endoglin include from 4 to 437 amino acids and from 10 to 1311 nucleotides.

By "gestational age" is meant a reference to the age of the fetus, counting from the first day of the mother's last menstrual period usually referred to in weeks.

By "gestational hypertension" is meant the development of high blood pressure without proteinuria after 20 weeks of pregnancy.

By a "history of pre-eclampsia or eclampsia" is meant a previous diagnosis of pre-eclampsia or eclampsia or pregnancy induced hypertension in the subject themselves or in a related family member.

By "homologous" is meant any gene or protein sequence that bears at least 30% homology, more preferably 40%, 50%, 60%, 70%, 80%, and most preferably 90% or more homology to a known gene or protein sequence over the length of the comparison sequence. A "homologous" protein can also have at least one biological activity of the comparison protein. In general, for proteins, the length of comparison sequences will be at least 10 amino acids, preferably 20, 30, 40, 50, 60, 70, 80, 90, 100, 110, 120, 130, 140, 150, 200, 250, 300, 350, 400, or at least 437 amino acids or more. For nucleic acids, the length of comparison sequences will generally be at least 25, 50, 100, 125, 150, 200, 250, 300, 350, 400, 450, 500, 550, 600, 650, 700, 800, 900, 1000, 1100, 1200, or at least 1311 nucleotides or more. "Homology" can also refer to a substantial similarity between an epitope used to generate antibodies and the protein or fragment thereof to which the antibodies are directed. In this case, homology refers to a similarity sufficient to elicit the production of antibodies that can specifically recognize the protein at issue.

By "humanized antibody" is meant an immunoglobulin amino acid sequence variant or fragment thereof that is capable of binding to a predetermined antigen. Ordinarily, the antibody will contain both the light chain as well as at least the variable domain of a heavy chain. The antibody also may include the CH1, hinge, CH2, CH3, or CH4 regions of the heavy chain. The humanized antibody comprises a framework region (FR) having substantially the amino acid sequence of a human immunoglobulin and a complementarity determining region (CDR) having substantially the amino acid sequence of a non-human immunoglobulin (the "import" sequences).

Generally, a humanized antibody has one or more amino acid residues introduced into it from a source that is non-human. In general, the humanized antibody will comprise substantially all of at least one, and typically two, variable domains (Fab, Fab', F(ab')$_2$, Fabc, Fv) in which all or substantially all of the CDR regions correspond to those of a non-human immunoglobulin and all or substantially all of the FR regions are those of a human immunoglobulin consensus sequence. The humanized antibody optimally will comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region (FR)" is meant the sequences of amino acids located on either side of the three hypervariable sequences (CDR) of the immunoglobulin light and heavy chains.

The FR and CDR regions of the humanized antibody need not correspond precisely to the parental sequences, e.g., the import CDR or the consensus FR may be mutagenized by substitution, insertion or deletion of at least one residue so that the CDR or FR residue at that site does not correspond to either the consensus or the import antibody. Such mutations, however, will not be extensive. Usually, at least 75%, preferably 90%, and most preferably at least 95% of the humanized antibody residues will correspond to those of the parental FR and CDR sequences.

By "hybridize" is meant pair to form a double-stranded molecule between complementary polynucleotide sequences, or portions thereof, under various conditions of stringency. (See, e.g., Wahl and Berger *Methods Enzymol.* 152:399, 1987; Kimmel, *Methods Enzymol.* 152:507, 1987.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (*Science* 196: 180, 1977); Grunstein and Hogness (*Proc. Natl. Acad. Sci., USA* 72:3961, 1975); Ausubel et al. (*Current Protocols in Molecular Biology*, Wiley Interscience, New York, 2001); Berger and Kimmel (*Guide to Molecular Cloning Techniques,* 1987, Academic Press, New York); and Sambrook et al., *Molecular Cloning: A Laboratory Manual*, Cold Spring Harbor Laboratory Press, New York.

By "intrauterine growth retardation (IUGR)" is meant a syndrome resulting in a birth weight which is less that 10 percent of the predicted fetal weight for the gestational age of the fetus. The current World Health Organization criterion for low birth weight is a weight less than 2,500 gm (5 lbs. 8 oz.) or below the $10^{th}$ percentile for gestational age according to U.S. tables of birth weight for gestational age by race, parity, and infant sex (Zhang and Bowes, *Obstet. Gynecol.* 86:200-208, 1995). These low birth weight babies are also referred to as "small for gestational age (SGA)". Pre-eclampsia is a condition known to be associated with IUGR or SGA.

By "metric" is meant a measure. A metric may be used, for example, to compare the levels of a polypeptide or nucleic acid molecule of interest. Exemplary metrics include, but are not limited to, mathematical formulas or algorithms, such as ratios. The metric to be used is that which best discriminates between levels of soluble endoglin, sFlt-1, VEGF, PlGF, or any combination thereof, in a subject having pregnancy related hypertensive disorder, such as pre-eclampsia or eclampsia, and a normal control subject. Depending on the metric that is used the diagnostic indicator of pregnancy related hypertensive disorder may be significantly above or below a reference value (e.g., from a control subject not having a pregnancy related hypertensive disorder). Soluble endoglin level is determined by measuring the amount of free, bound (i.e., bound to growth factor), or total (free+bound) soluble endoglin. sFlt-1 level is measured by measuring the amount of free, bound (i.e., bound to growth factor), or total sFlt-1 (bound+free). VEGF or PlGF levels are determined by measuring the amount of free PlGF or free VEGF (i.e., not bound to sFlt-1). One exemplary metric is [sFlt-1/(VEGF+PlGF)], also referred to as the pre-eclampsia anti-angiogenic index (PAAI). Another example is the following soluble endoglin anti-angiogenic index: (sFlt-1+0.25 (soluble endoglin polypeptide))/PlGF. An increase in the value of the soluble endoglin anti-angiogenic index is a diagnostic indicator of pre-eclampsia or eclampsia. Yet another exemplary metric is the following: (soluble enodglin+sFlt-1)/PlGF. Any of the metrics of the invention can further include the BMI of the mother or GA of the infant.

By "pre-eclampsia anti-angiogenesis index (PAAI)" is meant the ratio of sFlt-1/VEGF+PlGF used as an indicator of anti-angiogenic activity. A PAAI greater than 10, more preferably greater than 20, is indicative of a pregnancy related hypertensive disorder, such as pre-eclampsia or risk of pre-eclampsia.

By "soluble endoglin anti-angiogenic index" is meant the ratio of (sFlt-1+0.25 soluble endoglin)/PlGF. For example, a value of 75, or higher, preferably 100 or higher, or more preferably 200 or higher is indicative of a pregnancy complication associated with hypertension, such as pre-eclampsia or eclampsia.

By "operably linked" is meant that a gene and a regulatory sequence(s) are connected in such a way as to permit gene expression when the appropriate molecules (e.g., transcriptional activator proteins) are bound to the regulatory sequence(s).

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, (20th edition), ed. A. Gennaro, 2000, Lippincott, Williams & Wilkins, Philadelphia, Pa.

By "placental growth factor (PlGF)" is meant a mammalian growth factor that is homologous to the protein defined by GenBank accession number P49763 and that has PlGF biological activity. PlGF is a glycosylated homodimer belonging to the VEGF family and can be found in two distinct isoforms through alternative splicing mechanisms. PlGF is expressed by cyto- and syncytiotrophoblasts in the placenta and PlGF biological activities include induction of proliferation, migration, and activation of endothelial cells, particularly trophoblast cells.

By "polymorphism" is meant a genetic variation, mutation, deletion or addition in a soluble endoglin, sFlt-1, PlGF, or VEGF nucleic acid molecule that is indicative of a predisposition to develop pre-eclampsia or eclampsia. Such polymorphisms are known to the skilled artisan and are described, for example, by Raab et al. (*Biochem. J.* 339: 579-588, 1999) and Parry et al. (*Eur. J Immunogenet.* 26:321-323, 1999). A polymorphism may be present in the promoter sequence, an open reading frame, intronic sequence, or untranslated 3' region of a gene. Known examples of such polymorphisms in the endoglin gene include a 6 base insertion of GGGGGA in intron 7 at 26 bases beyond the 3' end of exon 7 (*Ann. Neurol.* 41:683-6, 1997).

By "pregnancy related hypertensive disorder" is meant any condition or disease or pregnancy that is associated with or characterized by an increase in blood pressure. Included among these conditions are pre-eclampsia (including premature pre-eclampsia, severe pre-eclampsia), eclampsia, gestational hypertension, HELLP syndrome, (hemolysis, elevated liver enzymes, low platelets), abruption placenta, chronic hypertension, pregnancy with intra uterine growth restriction, and pregnancy with a small for gestational age (SGA) infant. It should be noted that although pregnancy with a SGA infant is not often associated with hypertension, it is included in this definition.

By "pre-eclampsia" is meant the multi-system disorder that is characterized by hypertension with proteinuria or edema, or both, glomerular dysfunction, brain edema, liver edema, or coagulation abnormalities due to pregnancy or the influence of a recent pregnancy. All forms of pre-eclampsia, such as premature, mild, moderate, and severe pre-eclampsia are included in this definition. Pre-eclampsia generally occurs after the 20th week of gestation. Pre-eclampsia is generally defined as some combination of the following symptoms: (1) a systolic blood pressure (BP)>140 mmHg and a diastolic BP>90 mmHg after 20 weeks gestation (generally measured on two occasions, 4-168 hours apart), (2) new onset proteinuria (1+ by dipstik on urinanaysis, >300 mg of protein in a 24-hour urine collection, or a single random urine sample having a protein/creatinine ratio >0.3), and (3) resolution of hypertension and proteinuria by 12 weeks postpartum. Severe pre-eclampsia is generally defined as (1) a diastolic BP>110 mmHg (generally measured on two occasions, 4-168 hours apart) or (2) proteinuria characterized by a measurement of 3.5 g or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time.

HELLP syndrome is characterized by evidence of thrombocytopenia (<100000 cells/µl), increased LDH (>600 IU/L) and increased AST (>70 IU/L). Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

By "premature pre-eclampsia" is meant pre-eclampsia with onset of symptoms <37 weeks or <34 weeks.

By "protein" or "polypeptide" or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "reference sample" is meant any sample, standard, or level that is used for comparison purposes. A "normal reference sample" can be a prior sample taken from the same subject, a sample from a pregnant subject not having any pregnancy related hypertensive disorder, such as pre-eclampsia or eclampsia, a sample from a pregnant subject not having a pregnancy related hypertensive disorder, such as pre-eclampsia or eclampsia, a subject that is pregnant but the sample was taken early in pregnancy (e.g., in the first or second trimester or before the detection of a pregnancy related hypertensive disorder, such as pre-eclampsia or eclampsia), a subject that is pregnant and has no history of a pregnancy related hypertensive disorder, such as pre-eclampsia or eclampsia, a subject that is not pregnant, a sample of a purified reference polypeptide at a known normal concentration (i.e., not indicative of a pregnancy related hypertensive disorder, such as pre-eclampsia or eclampsia). By "reference standard or level" is meant a value or number derived from a reference sample. A normal reference standard or level can be a value or number derived from a normal subject that is matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of pre-eclampsia or eclampsia, and a family history of pre-eclampsia or eclampsia. A "positive reference" sample, standard or value is a sample or value or number derived from a subject that is known to have a pregnancy related hypertensive disorder, such as pre-eclampsia or eclampsia, that is matched to the sample subject by at least one of the following criteria: gestational age of the fetus, maternal age, maternal blood pressure prior to pregnancy, maternal blood pressure during pregnancy, BMI of the mother, weight of the fetus, prior diagnosis of a pregnancy related hypertensive disorder, and a family history of a pregnancy related hypertensive disorder By "reduce or inhibit" is meant the ability to cause an overall decrease preferably of 20% or greater, more preferably of 40%, 50%, 60%, 70%, 80%, 90% or greater change in the level of protein or nucleic acid, detected by the aforementioned assays (see "expression"), as compared to an untreated sample By "sample" is meant a tissue biopsy, cell, bodily fluid (e.g., blood, serum, plasma, urine, saliva, amniotic fluid, or cerebrospinal fluid) or other specimen obtained from a subject. Desirably, the biological sample includes soluble endoglin nucleic acid molecules or polypeptides or both.

By "small interfering RNAs (siRNAs)" is meant an isolated dsRNA molecule, preferably greater than 10 nucleotides (nt) in length, more preferably greater than 15 nucleotides in length, and most preferably greater than 19 nucleotides in length that is used to identify the target gene or mRNA to be degraded. A range of 19-25 nucleotides is the most preferred size for siRNAs. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the 19, 20, 21, 22, 23, 24, or 25 nt RNA or internally (at one or more nucleotides of the RNA). In a preferred embodiment, the RNA molecules contain a 3' hydroxyl group. Nucleotides in the RNA molecules of the present invention can also comprise non-standard nucleotides, including non-naturally occurring nucleotides or deoxyribonucleotides. Collectively, all such altered RNAs are referred to as analogs of RNA. siRNAs of the present invention need only be sufficiently similar to natural RNA that it has the ability to mediate RNA interference (RNAi). As used herein, RNAi refers to the ATP-dependent targeted cleavage and degradation of a specific mRNA molecule through the introduction of small interfering RNAs or dsRNAs into a cell or an organism. As used herein "mediate RNAi" refers to the ability to distinguish or identify which RNAs are to be degraded.

By "soluble endoglin binding molecule" is meant a protein or small molecule compound that specifically binds a soluble endoglin polypeptide. A soluble endoglin binding molecule may be, for example, an antibody, antibody-related peptide, one or more CDR regions of a soluble endoglin binding antibody, or soluble endoglin interacting protein.

By "soluble Flt-1 (sFlt-1)" (also known as sVEGF-R1) is meant the soluble form of the Flt-1 receptor, that is homologous to the protein defined by GenBank accession number U01134, and that has sFlt-1 biological activity. The biological activity of an sFlt-1 polypeptide may be assayed using any standard method, for example, by assaying sFlt-1 binding to VEGF. sFlt-1 lacks the transmembrane domain and the cytoplasmic tyrosine kinase domain of the Flt-1 receptor. sFlt-1 can bind to VEGF and PlGF with high affinity, but it cannot induce proliferation or angiogenesis and is therefore functionally different from the Flt-1 and KDR receptors. sFlt-1 was initially purified from human umbilical endothelial cells and later shown to be produced by trophoblast cells in vivo. As used herein, sFlt-1 includes any sFlt-1 family member or isoform. sFlt-1 can also mean degradation products or fragments that result from enzymatic cleavage of the Flt-1 receptor and that maintain sFlt-1 biological activity. In one example, specific metalloproteinases released from the placenta may cleave the extracellular domain of Flt-1 receptor to release the N-terminal portion of Flt-1 into circulation.

By "specifically binds" is meant a compound or antibody which recognizes and binds a polypeptide of the invention but that does not substantially recognize and bind other molecules in a sample, for example, a biological sample, which naturally includes a polypeptide of the invention. In one example, an antibody that specifically binds soluble endoglin does not bind membrane bound endoglin. In another example, an antibody that specifically binds to soluble endoglin recognizes a region within amino acids 1 to 437 of endoglin that is unique to soluble endoglin but not the full-length endoglin.

By "subject" is meant a mammal, including, but not limited to, a human or non-human mammal, such as a cow, a horse, a sheep, a pig, a goat, a dog, or a cat. Included in this definition are pregnant, post-partum, and non-pregnant mammals.

By "substantially identical" is meant a nucleic acid or amino acid sequence that, when optimally aligned, for example using the methods described below, share at least 60%, 65%, 70%, 75%, 80%, 85%, 90%, 95%, 96%, 97%, 98%, 99%, or 100% sequence identity with a second nucleic acid or amino acid sequence, e.g., an endoglin or soluble endoglin sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 10 amino acids, preferably 20, 30, 40, 50, 60, 70, 80, 90, 100, 110, 120, 130, 140, 150, 200, 250, 300, 350, 400, or at least 437 amino acids or more. For nucleic acids, the length of comparison sequences will generally be at least 25, 50, 100, 125, 150, 200, 250, 300, 350, 400, 450, 500, 550, 600, 650, 700, 800, 900, 1000, 1100, 1200, or at least 1311 nucleotides or more. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "symptoms of pre-eclampsia" is meant any of the following: (1) a systolic blood pressure (BP)>140 mmHg and a diastolic BP>90 mmHg after 20 weeks gestation, (2) new onset proteinuria (1+ by dipstik on urinanaysis, >300 mg of protein in a 24 hour urine collection, or random urine protein/creatinine ratio >0.3), and (3) resolution of hypertension and proteinuria by 12 weeks postpartum. The symptoms of pre-eclampsia can also include renal dysfunction and glomerular endotheliosis or hypertrophy. By "symptoms of eclampsia" is meant the development of any of the following symptoms due to pregnancy or the influence of a recent pregnancy: seizures, coma, thrombocytopenia, liver edema, pulmonary edema, and cerebral edema.

By "transforming growth factor $\beta$ (TGF-$\beta$)" is meant a mammalian growth factor that has TGF-$\beta$ biological activity and is a member of a family of structurally related paracrine polypeptides found ubiquitously in vertebrates, and prototypic of a large family of metazoan growth, differentiation, and morphogenesis factors (see, for review, Massaque et al. *Ann Rev Cell Biol* 6:597-641 (1990); Massaque et al. *Trends Cell Biol* 4:172-178 (1994); Kingsley Gene Dev. 8:133-146 (1994); and Sporn et al. J Cell Biol 119:1017-1021 (1992). As described in Kingsley, supra, the TGF-β superfamily has at least 25 members, and can be grouped into distinct sub-families with highly related sequences. The most obvious sub-families include the following: the TGF-β subfamily, which comprises at least four genes that are much more similar to TGF-β1 than to other members of the TGF-β superfamily; the activin sub-family, comprising homo- or hetero-dimers or two sub-units, inhibinβ-A and inhibinβ-B. The decapentaplegic sub-family, which includes the mammalian factors BMP2 and BMP4, which can induce the formation of ectopic bone and cartilage when implanted under the skin or into muscles. The 60A sub-family, which includes a number of mammalian homologs, with osteoinductive activity, including BMP5-8. Other members of the TGF-β superfamily include the gross differentiation factor 1 (GDF-1), GDF-3/VGR-2, dorsalin, nodal, mullerian-inhibiting substance (MIS), and glial-derived neurotrophic growth factor (GDNF). It is noted that the DPP and 60A sub-families are related more closely to one another than to other members of the TGF-β superfamily, and have often been grouped together as part of a larger collection of molecules called DVR (dpp and vg1 related). Unless evidenced from the context in which it is used, the term TGF-β as used throughout this specification will be understood to generally refer to members of the TGF-β superfamily as appropriate. (Massague et al, *Annu. Rev. Biochem.* 67:753-91, 1998; Josso et al, *Curr. Op. Gen. Dev.*, 7:371-377, 1997). TGF-β functions to regulate growth, differentiation, motility, tissue remodeling, neurogenesis, would repair, apoptosis, and angiogenesis in many cell types. TGF-β also inhibits cell proliferation in many cell types and can stimulate the synthesis of matrix proteins.

By "therapeutic amount" is meant an amount that when administered to a patient suffering from pre-eclampsia or eclampsia is sufficient to cause a qualitative or quantitative reduction in the symptoms of pre-eclampsia or eclampsia as described herein. A "therapeutic amount" can also mean an amount that when administered to a patient suffering from pre-eclampsia or eclampsia is sufficient to cause a reduction in the expression levels of endoglin or sFlt-1 or an increase in the expression levels of VEGF or PlGF as measured by the assays described herein.

By "treating" is meant administering a compound or a pharmaceutical composition for therapeutic purposes. To "treat disease" or use for "therapeutic treatment" refers to administering treatment to a subject already suffering from a disease to improve the subject's condition. Preferably, the subject is diagnosed as suffering from a pregnancy complication associated with hypertension, such as pre-eclampsia or eclampsia, based on identification of any of the characteristic symptoms described below or the use of the diagnostic methods described herein. To "prevent disease" refers to prophylactic treatment of a subject who is not yet ill, but who is susceptible to, or otherwise at risk of, developing a particular disease. Preferably a subject is determined to be at risk of developing pre-eclampsia or eclampsia using the diagnostic methods described herein. Thus, in the claims and embodiments, treating is the administration to a mammal either for therapeutic or prophylactic purposes.

By "trophoblast" is meant the mesectodermal cell layer covering the blastocyst that erodes the uterine mucosa and through which the embryo receives nourishment from the mother; the cells contribute to the formation of the placenta.

By "vascular endothelial growth factor (VEGF)" is meant a mammalian growth factor that is homologous to the growth factor defined in U.S. Pat. Nos. 5,332,671; 5,240, 848; 5,194,596; and Charnock-Jones et al. (*Biol. Reproduction,* 48: 1120-1128, 1993), and has VEGF biological activity. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. As used herein, VEGF includes any VEGF family member or isoform (e.g., VEGF-A, VEGF-B, VEGF-C, VEGF-D, VEGF-E, VEGF189, VEGF165, or VEGF 121). Preferably, VEGF is the VEGF121 or VEGF165 isoform (Tischer et al., *J. Biol. Chem.* 266, 11947-11954, 1991; Neufed et al. *Cancer Metastasis* 15:153-158, 1996), which is described in U.S. Pat. Nos. 6,447,768; 5,219,739; and 5,194,596, hereby incorporated by reference. Also included are mutant forms of VEGF such as the KDR-selective VEGF and Flt-selective VEGF described in Gille et al. (*J. Biol. Chem.* 276:3222-3230, 2001). As used herein VEGF also includes any modified forms of VEGF such as those described in LeCouter et al. (*Science* 299:890-893, 2003). Although human VEGF is preferred, the invention is not limited to human forms and can include other animal forms of VEGF (e.g. mouse, rat, dog, or chicken).

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

Other features and advantages of the invention will be apparent from the following description of the preferred embodiments thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows the predicted cDNA sequence (SEQ ID NO: 1) of soluble endoglin.

FIG. 2B shows the predicted amino acid sequence (SEQ ID NO: 2) of soluble endoglin.

FIG. 19 shows photomicrographs of double immunofluorescence staining of endoglin (red) and smooth muscle actin (green) for pre-eclamptic placentas taken at 25.2 weeks. The antibody used to detect endoglin stains both full-length endoglin and the soluble endoglin. Control placentas for the appropriate gestational windows were derived from patients with pre-term labor.

FIG. 21A is a photograph of the autoradiogram from immunoprecipitation and western blots experiments for endoglin using both pre-eclamptic placentas and serum. FIG. 21B is a photograph of the autoradiogram from immunoprecipitation and western blots experiments for endoglin using pre-eclamptic placentas. The three different N and P samples represent individual patients. For both figures commercially available monoclonal antibodies were used for immunoprecipitations and polyclonal antibodies were used for the western blots. Both these antibodies were raised against the N-terminal region of the endoglin protein and detect both the full length and the truncated soluble endoglin protein.

FIG. 27A shows the renal histology for the control group with no evidence of glomerular endotheliosis. FIG. 27B shows the renal histology for the soluble endoglin injected group with no evidence of glomerular endotheliosis. FIG. 27C shows the renal histology for sFlt1 injected rats showing moderate endotheliosis (shown by arrow head). FIG. 27D shows the renal histology for the soluble endoglin and sFlt1 injected rats showing extremely swollen glomeruli and severe glomerular endotheliosis with protein resorption droplets in the podocytes. All light micrographs were taken at 60× (original magnification).

DETAILED DESCRIPTION

Figure 1:
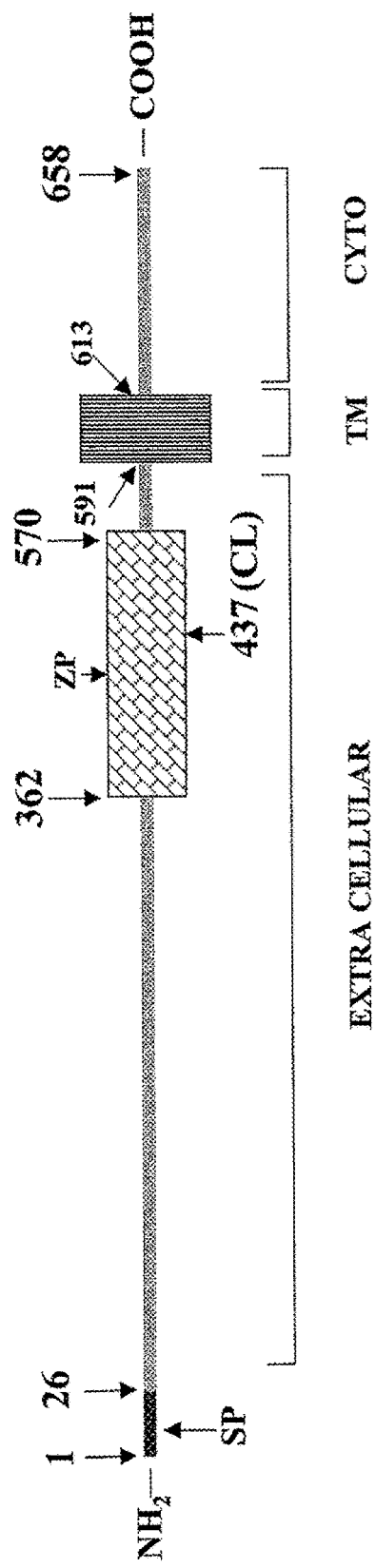
FIG. 1 is a schematic showing the endoglin protein. SP: signal peptide, ZP: zona pellucida domain, CL: potential cleavage site (amino acid 437) for the release of soluble endoglin, TM: transmembrane domain, Cyto: cytoplasmic domain.

We have discovered that soluble endoglin levels are elevated in blood serum samples taken from women with a pregnancy related hypertensive disorder, such as pre-eclampsia or eclampsia. Soluble endoglin may be formed by cleavage of the extracellular portion of the membrane bounds form by proteolytic enzymes. Excess soluble endoglin may be depleting the placenta of necessary amounts of these essential angiogenic and mitogenic factors. Thus, soluble endoglin is an excellent diagnostic marker pregnancy related hypertensive disorders, including pre-eclampsia and eclampsia. Furthermore, we have discovered therapeutic agents that interfere with soluble endoglin binding to growth factors, agents that reduce soluble endoglin expression or biological activity, or agents that increase levels of growth factors, can be used to treat or prevent pregnancy related hypertensive disorders, such as pre-eclampsia or eclampsia in a subject. Such agents include, but are not limited to, antibodies to soluble endoglin, oligonucleotides for antisense or RNAi that reduce levels of soluble endoglin, compounds that increase the levels of growth factors, compounds that prevent the proteolytic cleavage of the membrane bound form of endoglin thereby preventing the release of soluble endoglin, and small molecules that bind soluble endoglin and block the growth factor binding site. The invention also features methods for measuring levels of soluble endoglin as a detection tool for early diagnosis and management of a pregnancy related hypertensive disorder, including pre-eclampsia and eclampsia.

While the detailed description presented herein refers specifically to soluble endoglin, sFlt-1, VEGF, or PlGF, it will be clear to one skilled in the art that the detailed description can also apply to family members, isoforms, and/or variants of soluble endoglin, sFlt-1, VEGF, or PlGF.

Diagnostics

The present invention features assays based on the detection of soluble endoglin to pregnancy related hypertensive disorders, such as pre-eclampsia, eclampsia, or the propensity to develop such conditions. While the methods described herein refer to pre-eclampsia and eclampsia specifically, it should be understood that the diagnostic and monitoring methods of the invention apply to any pregnancy related hypertensive disorder including, but not limited to, gestational hypertension, pregnancy with a small for gestational age (SGA) infant, HELLP, chronic hypertension, pre-eclampsia (mild, moderate, and severe), and eclampsia.

Levels of endoglin, either free, bound, or total levels, are measured in a subject sample and used as an indicator of pre-eclampsia, eclampsia, or the propensity to develop such conditions.

A subject having pre-eclampsia, eclampsia, or a predisposition to such conditions will show an increase in the expression of a soluble endoglin polypeptide. The soluble endoglin polypeptide can include full-length soluble endoglin, degradation products, alternatively spliced isoforms of soluble endoglin, enzymatic cleavage products of soluble endoglin, and the like. An antibody that specifically binds a soluble endoglin polypeptide may be used for the diagnosis of pre-eclampsia or eclampsia or to identify a subject at risk of developing such conditions. One example of an antibody useful in the methods of the invention is a monoclonal antibody against the N-terminal region of endoglin that is commercially available from Santa Cruz Biotechnology, Inc. (cat # sc-20072). A variety of protocols for measuring an alteration in the expression of such polypeptides are known, including immunological methods (such as ELISAs and RIAs), and provide a basis for diagnosing pre-eclampsia or eclampsia or a risk of developing such conditions. Again, an increase in the level of the soluble endoglin polypeptide is diagnostic of a subject having pre-eclampsia, eclampsia, or a predisposition to such conditions.

Elevated levels of soluble endoglin are a positive indicator of pre-eclampsia or eclampsia. For example, if the level of soluble endoglin is increased relative to a reference (e.g., 10%, 20%, 30%, 40%, 50%, 60%, 70%, 80%, 90% or more), this is considered a positive indicator of pre-eclampsia or eclampsia. Additionally, any detectable alteration in levels of soluble endoglin, sFlt-1, VEGF, or PlGF relative to normal levels is indicative of eclampsia, pre-eclampsia, or the propensity to develop such conditions. Normally, circulating serum concentrations of soluble endoglin range from 2-7 ng/ml during the non-pregnant state and from 10-20 ng/ml during normal pregnancy. Elevated serum levels, greater than 15 ng/ml, preferably greater than 20 ng/ml, and most preferably greater than 25 ng/ml or more, of soluble endoglin is considered a positive indicator of pre-eclampsia.

In one embodiment, the level of soluble endoglin is measured in combination with the level of sFlt-1, VEGF, or PlGF polypeptide or nucleic acid, or any combination thereof. Methods for the measurement of sFlt-1, VEGF, and PlGF are described in PCT Publication Number WO 2004/008946 and U.S. Publication No. 20040126828, hereby incorporated by reference in their entirety. In additional preferred embodiments, the body mass index (BMI) and gestational age of the fetus is also measured and included the diagnostic metric.

In one embodiment, a metric incorporating soluble endoglin, sFlt-1, VEGF, or PlGF, or any combination therein, is used to determine whether a relationship between levels of at least two of the proteins is indicative of pre-eclampsia or eclampsia. In one example, the metric is a PAAI (sFlt-1/VEGF+PlGF), which is used, in combination with soluble endoglin measurement, as an anti-angiogenic index that is diagnostic of pre-eclampsia, eclampsia, or the propensity to develop such conditions. If the level of soluble endoglin is increased relative to a reference sample (e.g., 1.5-fold, 2-fold, 3-fold, 4-fold, or even by as much as 10-fold or more), and the PAAI is greater than 10, more preferably greater than 20, then the subject is considered to have pre-eclampsia, eclampsia, or to be in imminent risk of developing the same. The PAAI (sFlt-1/VEGF+PlGF) ratio is merely one example of a useful metric that may be used as a diagnostic indicator. It is not intended to limit the invention. Virtually any metric that detects an alteration in the levels of soluble endoglin, sFlt-1, PlGF, or VEGF, or any combination thereof, in a subject relative to a normal control may be used as a diagnostic indicator. Another example is the following soluble endoglin anti-angiogenic index: (sFlt-1+0.25 (soluble endoglin polypeptide))/PlGF. An increase in the value of the soluble endoglin metric is a diagnostic indicator of pre-eclampsia or eclampsia. A soluble endoglin index above 100, preferably above 200 is a diagnostic indicator of pre-eclampsia or eclampsia. Another example is the following index: (soluble endoglin+sFlt-1)/PlGF. The indexes can further include the BMI of the mother or the GA of the infant.

Standard methods may be used to measure levels of soluble endoglin, VEGF, PlGF, or sFlt-1 polypeptide in any bodily fluid, including, but not limited to, urine, serum, plasma, saliva, amniotic fluid, or cerebrospinal fluid. Such methods include immunoassay, ELISA, western blotting using antibodies directed to soluble endoglin, VEGF, PlGF or sFlt-1, and quantitative enzyme immunoassay techniques such as those described in Ong et al. (*Obstet. Gynecol.* 98:608-611, 2001) and Su et al. (*Obstet. Gynecol.*, 97:898-904, 2001). ELISA assays are the preferred method for measuring levels of soluble endoglin, VEGF, PlGF, or sFlt-1. Preferably, soluble endoglin is measured.

Oligonucleotides or longer fragments derived from an endoglin, sFlt-1, PlGF, or VEGF nucleic acid sequence may be used as a probe not only to monitor expression, but also to identify subjects having a genetic variation, mutation, or polymorphism in an endoglin, sFlt-1, PlGF, or VEGF nucleic acid molecule that are indicative of a predisposition to develop the pre-eclampsia or eclampsia. These polymorphisms may affect nucleic acid or polypeptide expression levels or biological activity. Such polymorphisms are known to the skilled artisan and are described, for example, by Raab et al., supra, and Parry et al. (*Eur. J Immunogenet.* 26:321-3, 1999). For example, polymorphisms in the endoglin gene have been described and many of these are associated with the dominant vascular disorder known as hereditary haemorrhagic telengiectasia type I (HHT1). Many of these mutations lead to the production of a soluble form of endoglin that is unstable, resulting in the decreased expression of endoglin found in endothelial cells and monocytes of HHT patients (Raab et al., supra). In another example, a survey of the GenBank database (www.ncbi.nlm.nih.gov) reveals at least 330 known polymorphisms in the gene and the promoter region of Flt-1/sFlt-1. Detection of genetic variation, mutation, or polymorphism relative to a normal, reference sample can be used as a diagnostic indicator of pre-eclampsia, eclampsia, or the propensity to develop pre-eclampsia or eclampsia.

Such genetic alterations may be present in the promoter sequence, an open reading frame, intronic sequence, or untranslated 3' region of a gene. Information related to genetic alterations can be used to diagnose a subject as having pre-eclampsia, eclampsia, or a predisposition to such conditions. As noted throughout, specific alterations in the levels or biological activity of soluble endoglin, sFlt-1, VEGF, or PlGF, or any combination thereof, can be correlated with the likelihood of pre-eclampsia or eclampsia, or the predisposition to the same. As a result, one skilled in the art, having detected a given mutation, can then assay one or more of the biological activities of the protein to determine if the mutation causes or increases the likelihood of pre-eclampsia or eclampsia.

In one embodiment, a subject having pre-eclampsia, eclampsia, or a predisposition to such conditions will show an increase in the expression of a nucleic acid encoding endoglin, preferably soluble endoglin, or sFlt-1, or an alteration in PlGF or VEGF levels. Methods for detecting such alterations are standard in the art and are described in Ausubel et al., supra. In one example northern blotting or real-time PCR is used to detect endoglin, preferably soluble endoglin, sFlt-1, PlGF, or VEGF mRNA levels.

Hybridization with PCR probes that are capable of detecting an endoglin or soluble endoglin nucleic acid molecule, including genomic sequences, or closely related molecules, may be used to hybridize to a nucleic acid sequence derived from a subject having pre-eclampsia or eclampsia or at risk of developing such conditions. The specificity of the probe, whether it is made from a highly specific region, e.g., the 5' regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences. Hybridization techniques may be used to identify mutations indicative of a pre-eclampsia or eclampsia in a soluble endoglin nucleic acid molecule, or may be used to monitor expression levels of a gene encoding a soluble endoglin polypeptide (for example, by Northern analysis, Ausubel et al., supra).

In yet another embodiment, subjects may be diagnosed for a predisposition to pre-eclampsia or eclampsia by direct analysis of the sequence of an endoglin or soluble endoglin nucleic acid molecule.

The measurement of any of the nucleic acids or polypeptides described herein can occur on at least two different occasions and an alteration in the levels as compared to normal reference levels over time is used as an indicator of pre-eclampsia, eclampsia, or the propensity to develop such conditions.

The level of any of the soluble endoglin polypeptide or nucleic acid present in the bodily fluids of a subject having pre-eclampsia, eclampsia, or the propensity to develop such conditions may be increased by as little as 10%, 20%, 30%, or 40%, or by as much as 50%, 60%, 70%, 80%, 90%, 95%, 96%, 97%, 98%, 99% or more relative to levels in a normal control subject or relative to a previous sampling obtained from the same bodily fluids of the same subject. The level of a soluble endoglin polypeptide or nucleic acid in the bodily fluids of a subject having pre-eclampsia, eclampsia, or the propensity to develop such conditions may be altered by as little as 10%, 20%, 30%, or 40%, or by as much as 50%, 60%, 70%, 80%, 90%, 95%, 96%, 97%, 98%, 99% over time from one measurement to the next.

The level of sFlt-1, VEGF, or PlGF measured in combination with the level of soluble endoglin in the bodily fluids of a subject having pre-eclampsia, eclampsia, or the propensity to develop such conditions may be altered by as little as 10%, 20%, 30%, or 40%, or by as much as 50%, 60%, 70%, 80%, 90%, 95%, 96%, 97%, 98%, 99% or more relative to the level of sFlt-1, VEGF, or PlGF in a normal control. The level of sFlt-1, VEGF, or PlGF measured in combination with the level of soluble endoglin in the bodily fluids of a subject having pre-eclampsia, eclampsia, or the propensity to develop such conditions may be altered by as little as 10%, 20%, 30%, or 40%, or by as much as 50%, 60%, 70%, 80%, 90%, 95%, 96%, 97%, 98%, 99% over time from one measurement to the next.

In one embodiment, a subject sample of a bodily fluid (e.g., urine, plasma, serum, amniotic fluid, or cerebrospinal fluid) is collected early in pregnancy prior to the onset of pre-eclampsia symptoms. In another example, the sample can be a tissue or cell collected early in pregnancy prior to the onset of pre-eclampsia symptoms. Non-limiting examples of tissues and cells include placental tissue, placental cells, endothelial cells, and leukocytes such as monocytes. In humans, for example, maternal blood serum samples are collected from the antecubital vein of pregnant women during the first, second, or third trimesters of the pregnancy. Preferably, the assay is carried out during the first trimester, for example, at 4, 6, 8, 10, or 12 weeks, or any interval therein, or during the second trimester, for example at 14, 16, 18, 20, 22, or 24 weeks, or any interval therein. Such assays may also be conducted at the end of the second trimester or the third trimester, for example at 26, 28, 30, 32, 34, 36, or 38 weeks, or any interval therein. It is preferable that levels of soluble endoglin be measured twice during this period of time. For the diagnosis of post-partum pre-eclampsia or eclampsia, assays for soluble endoglin may be carried out postpartum. For the diagnosis of a predisposition to pre-eclampsia or eclampsia, the assay is carried out prior to the onset of pregnancy. In one example, for the monitoring and management of therapy, the assay is carried out during the pregnancy after the diagnosis of pre-eclampsia.

In one particular example, serial blood samples can be collected during pregnancy and the levels of soluble endoglin polypeptide determined by ELISA. In another example, a sample is collected during the second trimester and early in the third trimester and in increase in the level of soluble endoglin from the first sampling to the next is indicative of pre-eclampsia or eclampsia, or the propensity to develop either.

The invention also include the measurement of any ligands of soluble endoglin (e.g., TGF-β1, TGF-β3, activin-A, BMP-2, and BMP-7) ligand in a bodily fluid from a subject, preferably urine, and an alteration (e.g., increase or decrease) in the level of the soluble endoglin ligand is indicative of pre-eclampsia or eclampsia.

In veterinary practice, assays may be carried out at any time during the pregnancy, but are, preferably, carried out early in pregnancy, prior to the onset of pre-eclampsia symptoms. Given that the term of pregnancies varies widely between species, the timing of the assay will be determined by a veterinarian, but will generally correspond to the timing of assays during a human pregnancy.

The diagnostic methods described herein can be used individually or in combination with any other diagnostic method described herein for a more accurate diagnosis of the presence of, severity of, or estimated time of onset of pre-eclampsia or eclampsia. In addition, the diagnostic methods described herein can be used in combination with any other diagnostic methods determined to be useful for the accurate diagnosis of the presence of, severity of, or estimated time of onset of pre-eclampsia or eclampsia.

The diagnostic methods described herein can also be used to monitor and manage pre-eclampsia or eclampsia in a subject. In one example, a therapy is administered until the blood, plasma, or serum soluble endoglin level is less than 25 ng/ml. In another example, if a subject is determined to have an increased level of soluble endoglin relative to a normal control then the therapy can be administered until the serum PlGF level rises to approximately 400 pg/mL. In this embodiment, the levels of soluble endoglin, sFlt-1, PlGF, and VEGF, or any and all of these, are measured repeatedly as a method of not only diagnosing disease but monitoring the treatment and management of the pre-eclampsia and eclampsia.

Diagnostic Kits

The invention also provides for a diagnostic test kit. For example, a diagnostic test kit can include antibodies to soluble endoglin and means for detecting, and more preferably evaluating, binding between the antibodies and the soluble endoglin polypeptide. For detection, either the antibody or the soluble endoglin polypeptide is labeled, and either the antibody or the soluble endoglin polypeptide is substrate-bound, such that soluble endoglin polypeptide-antibody interaction can be established by determining the amount of label attached to the substrate following binding between the antibody and the soluble endoglin polypeptide. A conventional ELISA is a common, art-known method for detecting antibody-substrate interaction and can be provided with the kit of the invention. Soluble endoglin polypeptides can be detected in virtually any bodily fluid including, but not limited to urine, serum, plasma, saliva, amniotic fluid, or cerebrospinal fluid. The invention also provides for a diagnostic test kit that includes a soluble endoglin nucleic acid that can be used to detect and determine levels of soluble endoglin nucleic acids. A kit that determines an alteration in the level of soluble endoglin polypeptide relative to a reference, such as the level present in a normal control, is useful as a diagnostic kit in the methods of the invention.

The diagnostic kits of the invention can include antibodies or nucleic acids for the detection of sFlt-1, VEGF, or PlGF polypeptides or nucleic acids as described in U.S. Patent Application Publication Numbers 20040126828, 20050025762, and 2005017044 and PCT Publication Numbers WO 2004/008946 and WO 2005/077007.

Desirably, the kit includes any of the components needed to perform any of the diagnostic methods described above. For example, the kit desirably includes a membrane, where the soluble endoglin binding agent or the agent that binds the soluble endoglin binding agent is immobilized on the membrane. The membrane can be supported on a dipstick structure where the sample is deposited on the membrane by placing the dipstick structure into the sample or the membrane can be supported in a lateral flow cassette where the sample is deposited on the membrane through an opening in the cassette.

The diagnostic kits also generally include a label or instructions for the intended use of the kit components and a reference sample or purified proteins to be used to establish a standard curve. In one example, the kit contains instructions for the use of the kit for the diagnosis of pre-eclampsia, eclampsia, or the propensity to develop pre-eclampsia or eclampsia. In yet another example, the kit contains instructions for the use of the kit to monitor therapeutic treatment or dosage regimens for the treatment of pre-eclampsia or eclampsia. The diagnostic kit may also include a label or instructions for the use of the kit to determine the PAAI or soluble endoglin anti-angiogenesis index of the subject sample and to compare the PAAI or soluble endoglin anti-angiogenesis index to a reference sample value. It will be understood that the reference sample values will depend on the intended use of the kit. For example, the sample can be compared to a normal reference value, wherein an increase in the PAAI or soluble endoglin anti-angiogenesis index or in the soluble endoglin value is indicative of pre-eclampsia or eclampsia, or a predisposition to pre-eclampsia or eclampsia. In another example, a kit used for therapeutic monitoring can have a reference PAAI or soluble endoglin anti-angiogenesis index value or soluble endoglin value that is indicative of pre-eclampsia or eclampsia, wherein a decrease in the PAAI or soluble endoglin anti-angiogenesis index value or a decrease in the soluble endoglin value of the subject sample relative to the reference sample can be used to indicate therapeutic efficacy or effective dosages of therapeutic compounds.

Screening Assays

As discussed above, the level of a soluble endoglin nucleic acid or polypeptide is increased in a subject having pre-eclampsia, eclampsia, or a predisposition to such conditions. Based on these discoveries, compositions of the invention are useful for the high-throughput low-cost screening of candidate compounds to identify those that modulate the expression of a soluble endoglin polypeptide or nucleic acid molecule whose expression is altered in a subject having a pre-eclampsia or eclampsia.

Any number of methods are available for carrying out screening assays to identify new candidate compounds that alter the expression of a soluble endoglin nucleic acid molecule. In one working example, candidate compounds are added at varying concentrations to the culture medium of cultured cells expressing a soluble endoglin nucleic acid sequence. Exemplary cell cultures include trophoblasts (e.g., BEWO, JAR, and JEG cells) and HUVECs. Cells that express high levels of the membrane bound form of endoglin can be treated with a proteinase (e.g., a matrix metalloproteinase) that cleaves the extracellular domain of endoglin to form soluble endoglin. These cells can then be used to screen for new candidate compounds. Gene expression is then measured, for example, by microarray analysis, Northern blot analysis (Ausubel et al., supra), or RT-PCR, using any appropriate fragment prepared from the nucleic acid molecule as a hybridization probe. The level of gene expression in the presence of the candidate compound is compared to the level measured in a control culture medium lacking the candidate compound. A compound that promotes a decrease in the expression of a soluble endoglin gene, nucleic acid molecule, or polypeptide, or a functional equivalent thereof, is considered useful in the invention; such a molecule may be used, for example, as a therapeutic to treat pre-eclampsia or eclampsia in a subject.

In another working example, the effect of candidate compounds may be measured at the level of polypeptide production using the same general approach and standard immunological techniques, such as western blotting or immunoprecipitation with an antibody specific for a soluble endoglin polypeptide. For example, immunoassays may be used to detect or monitor the expression of at least one of the polypeptides of the invention in an organism. Polyclonal or monoclonal antibodies (produced as described above) that are capable of binding to such a polypeptide may be used in any standard immunoassay format (e.g., ELISA, western blot, or RIA assay) to measure the level of the polypeptide. In some embodiments, a compound that promotes a decrease in the expression or biological activity of a soluble endoglin polypeptide is considered particularly useful. Again, such a molecule may be used, for example, as a therapeutic to delay, ameliorate, or treat a pre-eclampsia or eclampsia, or the symptoms of a pre-eclampsia or eclampsia, in a subject.

In yet another working example, candidate compounds may be screened for those that specifically bind to a soluble endoglin polypeptide. The efficacy of such a candidate compound is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate compound may be tested in vitro for its ability to specifically bind a polypeptide of the invention. In another embodiment, a candidate compound is tested for its ability to decrease the biological activity of a soluble endoglin polypeptide by decreasing binding of a soluble endoglin polypeptide and a growth factor, such as TGF-β1, TGF-β3, activin-A, BMP-2 and BMP-7.

In another working example, a soluble endoglin nucleic acid is expressed as a transcriptional or translational fusion with a detectable reporter, and expressed in an isolated cell (e.g., mammalian or insect cell) under the control of a heterologous promoter, such as an inducible promoter. The cell expressing the fusion protein is then contacted with a candidate compound, and the expression of the detectable reporter in that cell is compared to the expression of the detectable reporter in an untreated control cell. A candidate compound that decreases the expression of a soluble endoglin detectable reporter is a compound that is useful for the treatment of pre-eclampsia or eclampsia. In preferred embodiments, the candidate compound alters the expression of a reporter gene fused to a nucleic acid or nucleic acid.

In one particular working example, a candidate compound that binds to a soluble endoglin polypeptide may be identified using a chromatography-based technique. For example, a recombinant polypeptide of the invention may be purified by standard techniques from cells engineered to express the polypeptide (e.g., those described above) and may be immobilized on a column. A solution of candidate compounds is then passed through the column, and a compound specific for the soluble endoglin polypeptide is identified on the basis of its ability to bind to the polypeptide and be immobilized on the column. To isolate the compound, the column is washed to remove non-specifically bound molecules, and the compound of interest is then released from the column and collected. Similar methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to decrease the activity of a soluble endoglin polypeptide. Compounds isolated by this approach may also be used, for example, as therapeutics to treat pre-eclampsia or eclampsia in a human subject. Compounds that are identified as binding to a polypeptide of the invention with an affinity constant less than or equal to 10 mM are considered particularly useful in the invention. Alternatively, any in vivo protein interaction detection system, for example, any two-hybrid assay may be utilized to identify compounds or proteins that bind to a polypeptide of the invention.

Potential antagonists include organic molecules, peptides, peptide mimetics, polypeptides, nucleic acids, and antibodies that bind to a soluble endoglin nucleic acid sequence or a soluble endoglin polypeptide.

Soluble endoglin DNA sequences may also be used in the discovery and development of a therapeutic compound for the treatment of pre-eclampsia or eclampsia. The encoded protein, upon expression, can be used as a target for the screening of drugs. Additionally, the DNA sequences encoding the amino terminal regions of the encoded protein or Shine-Delgarno or other translation facilitating sequences may be isolated by standard techniques (Ausubel et al., supra).

Optionally, compounds identified in any of the above-described assays may be confirmed as useful in an assay for compounds that decrease the biological activity of soluble endoglin.

Small molecules of the invention preferably have a molecular weight below 2,000 daltons, more preferably between 300 and 1,000 daltons, and most preferably between 400 and 700 daltons. It is preferred that these small molecules are organic molecules.

Test Compounds and Extracts

In general, compounds capable of decreasing the activity of a soluble endoglin polypeptide are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their molt-disrupting activity should be employed whenever possible.

When a crude extract is found to decrease the activity of a soluble endoglin polypeptide, or to bind to a soluble endoglin polypeptide, further fractionation of the positive lead extract is necessary to isolate chemical constituents responsible for the observed effect. Thus, the goal of the extraction, fractionation, and purification process is the careful characterization and identification of a chemical entity within the crude extract that decreases the activity of a soluble endoglin polypeptide. Methods of fractionation and purification of such heterogeneous extracts are known in the art. If desired, compounds shown to be useful as therapeutics for the treatment of a human pre-eclampsia or eclampsia are chemically modified according to methods known in the art.

Therapeutics

The present invention features methods and compositions for treating or preventing pre-eclampsia or eclampsia in a subject. Given that levels of soluble endoglin are increased in subjects having pre-eclampsia, eclampsia, or having a predisposition to such conditions, any agent that decreases the expression levels and/or biological activity of a soluble endoglin polypeptide or nucleic acid molecule is useful in the methods of the invention. Such agents include compounds such as TGF-$\beta$1, TGF-$\beta$3, activin-A, BMP2, or BMP7, that can disrupt soluble endoglin binding to ligands; a purified antibody or antigen-binding fragment that specifically binds soluble endoglin; antisense nucleobase oligomers; and dsRNAs used to mediate RNA interference. Additional useful compounds include any compounds that can alter the biological activity of soluble endoglin, for example, as measured by an angiogenesis assay. Exemplary treatment methods are described in detail below. These methods can also be combined with methods to decrease sFlt-1 levels or to increase VEGF or PlGF levels or decrease sFlt-1 levels as described in PCT Publication Number WO 2004/008946 and U.S. Patent Publication No. 20040126828.

Therapeutics Targeting the TGF-$\beta$ Signaling Pathway

TGF-$\beta$ is the prototype of a family of at least 25 growth factors which regulate growth, differentiation, motility, tissue remodeling, neurogenesis, wound repair, apoptosis, and angiogenesis in many cell types. TGF-$\beta$ also inhibits cell proliferation in many cell types and can stimulate the synthesis of matrix proteins. Unless evidenced from the context in which it is used, the term TGF-$\beta$ as used throughout this specification will be understood to generally refer to any and all members of the TGF-$\beta$ superfamily as appropriate. Soluble endoglin binds several specific members of the TGF-$\beta$ family including TGF-$\beta$1, TGF-$\beta$3, activin, BMP-2 and BMP-7, and may serve to deplete the developing fetus or placenta of these necessary mitogenic and angiogenic factor. The present invention features methods of increasing the levels of these ligands to bind to soluble endoglin and to neutralize the effects of soluble endoglin.

Purified Proteins

In a preferred embodiment of the present invention, purified forms of any soluble endoglin ligand such as TGF-$\beta$ family proteins, including but not limited to TGF-$\beta$1, TGF-$\beta$3, activin-A, BMP2, and BMP7, are administered to the subject in order to treat or prevent pre-eclampsia or eclampsia.

Purified TGF-$\beta$ family proteins include any protein with an amino acid sequence that is homologous, more desirably, substantially identical to the amino acid sequence of TGF-$\beta$1 or TGF-$\beta$3, or any known TGF-$\beta$ family member, that can induce angiogenesis. Non-limiting examples include human TGF-$\beta$1 (Cat #240-B-002) and human TGF-$\beta$3 (Cat #243-B3-002) from R & D Systems, MN.

Therapeutic Compounds that Inhibit Proteolytic Cleavage of Endgolin

We have identified a potential cleavage site in the extracellular domain of endoglin where a proteolytic enzyme could cleave the membrane bound form of endoglin, releasing the extracellular domain as a soluble form. Our sequence alignments of the cleavage site suggest that a matrix metalloproteinase (MMP) may be responsible for the cleavage and release of soluble endoglin. Alternatively, a cathepsin or an elastase may also be involved in the cleavage event. MMPs are also known as collagenases, gelatinases, and stromelysins and there are currently 26 family members known (for a review see Whittaker and Ayscough, *Cell Transmissions* 17:1 (2001)). A preferred MMP is MMP9, which is known to be up-regulated in placentas from pre-eclamptic patients (Lim et al., *Am. J. Pathol.* 151:1809-1818, 1997). The activity of MMPs is controlled through activation of pro-enzymes and inhibition by endogenous inhibitors such as the tissue inhibitors of metalloproteinases (TIMPS). Inhibitors of MMPs are zinc binding proteins. There are 4 known endogenous inhibitors (TIMP 1-4), which are reviewed in Whittaker et al., supra. One preferred MMP inhibitor is the inhibitor of membrane type-MMP1 that has been shown to cleave betaglycan, a molecule that shares similarity to endoglin (Velasco-Loyden et al., *J. Biol. Chem.* 279:7721-7733 (2004)). In addition, a variety of naturally-occurring and synthetic MMP inhibitors have been identified and are also reviewed in Whittaker et al., supra. Examples include antibodies directed to MMPs, and various compounds including marimastat, batimastat, CT1746, BAY 12-9566, Prinomastat, CGS-27023A, D9120, BMS275291 (Bristol Myers Squibb), and trocade, some of which are currently in clinical trials. Given the potential role of MMPs, cathepsins, or elastases in the release and up-regulation of soluble endoglin levels, the present invention also provides for the use of any compound, such as those described above, known to inhibit the activity of any MMP, cathepsin, or elastase involved in the cleavage and release of soluble endoglin, for the treatment or prevention of pre-eclampsia or eclampsia in a subject.

Therapeutic Compounds that Increase Soluble Endoglin Binding Proteins

The present invention provides for the use of any compound known to stimulate or increase blood serum levels of soluble endoglin binding proteins, including but not limited to TGF-β1, TGF-β3, activin-A, BMP2, and BMP7, for the treatment or prevention of pre-eclampsia in a subject. These compounds can be used alone or in combination with the purified proteins described above or any of the other methods used to increase TGF-β family proteins protein levels described herein. In one example, cyclosporine is used to stimulate TGF-β1 production at a dosage of 100-200 mg twice a day.

In addition to the use of compounds that can increase serum levels of soluble endoglin binding proteins, the invention provides for the use of any chronic hypertension medications used in combination with any of the therapeutic methods described herein. Medications used for the treatment of hypertension during pregnancy include methyldopa, hydralazine hydrochloride, or labetalol. For each of these medications, modes of administration and dosages are determined by the physician and by the manufacturer's instructions.

Therapeutic Compounds that Alter the Anti-angiogenic Activity of Soluble Endoglin Additional therapeutic compounds can be identified using angiogenesis assays. For example, pre-eclamptic serum having elevated levels of soluble endoglin are added to a matrigel tube formation assay will induce an anti-angiogenic state. Test compounds can then be added to the assay and a reversion in the anti-angiogenic state by 10%, 20%, 30%, 40%, 50%, 60%, 70%, 80%, 90% or more indicates that the compound can reduce the biological activity of soluble endoglin and is useful as a therapeutic compound.

Therapeutic Nucleic Acids

Recent work has shown that the delivery of nucleic acid (DNA or RNA) capable of expressing an endothelial cell mitogen such as VEGF to the site of a blood vessel injury will induce proliferation and reendothelialization of the injured vessel. While the present invention does not relate to blood vessel injury, these general techniques for the delivery of nucleic acid to endothelial cells can be used in the present invention for the delivery of nucleic acids encoding soluble endoglin binding proteins, such as TGF-β1, TGF-β3, activin-A, BMP2 and BMP7. The techniques can also be used for the delivery of nucleic acids encoding proteins, such as those described above, known to inhibit the activity of any MMP, cathepsin, or elastase involved in the cleavage and release of soluble endoglin, for the treatment or prevention of pre-eclampsia or eclampsia in a subject. These general techniques are described in U.S. Pat. Nos. 5,830,879 and 6,258,787 and are incorporated herein by reference.

In the present invention the nucleic acid may be any nucleic acid (DNA or RNA) including genomic DNA, cDNA, and mRNA, encoding a soluble endoglin binding proteins such as TGF-β1, TGF-β3, activin-A, BMP2 and BMP7. The nucleic acids encoding the desired protein may be obtained using routine procedures in the art, e.g. recombinant DNA, PCR amplification.

Modes for Delivering Nucleic Acids

For any of the nucleic acid applications described herein, standard methods for administering nucleic acids can be used. For example, to simplify the manipulation and handling of the nucleic acid encoding the soluble endoglin binding protein, the nucleic acid is preferably inserted into a cassette where it is operably linked to a promoter. The promoter must be capable of driving expression of the soluble endoglin binding protein in the desired target host cell. The selection of appropriate promoters can readily be accomplished. Preferably, one would use a high expression promoter. An example of a suitable promoter is the 763-base-pair cytomegalovirus (CMV) promoter. The Rous sarcoma virus (RSV) (Davis, et al., *Hum. Gene Ther.* 4:151-159, 1993) and mouse mammary tumor virus (MMTV) promoters may also be used. Certain proteins can be expressed using their native promoter. Other elements that can enhance expression can also be included (e.g., enhancers or a system that results in high levels of expression such as a tat gene and tar element). The recombinant vector can be a plasmid vector such as pUC118, pBR322, or other known plasmid vectors, that includes, for example, an *E. coli* origin of replication (see, Sambrook, et al., Molecular Cloning: A Laboratory Manual, Cold Spring Harbor Laboratory press, 1989). The plasmid vector may also include a selectable marker such as the β lactamase gene for ampicillin resistance, provided that the marker polypeptide does not adversely affect the metabolism of the organism being treated. The cassette can also be bound to a nucleic acid binding moiety in a synthetic delivery system, such as the system disclosed in PCT Publication No. WO95/22618.

The nucleic acid can be introduced into the cells by any means appropriate for the vector employed. Many such methods are well known in the art (Sambrook et al., supra, and Watson et al., "Recombinant DNA", Chapter 12, 2d edition, Scientific American Books, 1992). Recombinant vectors can be transferred by methods such as calcium phosphate precipitation, electroporation, liposome-mediated transfection, gene gun, microinjection, viral capsid-mediated transfer, polybrene-mediated transfer, or protoplast fusion. For a review of the procedures for liposome preparation, targeting and delivery of contents, see Mannino and Gould-Fogerite, (*Bio Techniques,* 6:682-690, 1988), Felgner and Holm, (*Bethesda Res. Lab. Focus,* 11:21, 1989) and Maurer (*Bethesda Res. Lab. Focus,* 11:25, 1989).

Transfer of the recombinant vector (either plasmid vector or viral vectors) can be accomplished through direct injection into the amniotic fluid or intravenous delivery.

Gene delivery using adenoviral vectors or adeno-associated vectors (AAV) can also be used. Adenoviruses are present in a large number of animal species, are not very pathogenic, and can replicate equally well in dividing and quiescent cells. As a general rule, adenoviruses used for gene delivery are lacking one or more genes required for viral replication. Replication-defective recombinant adenoviral vectors used for the delivery of a soluble endoglin binding protein, can be produced in accordance with art-known techniques (see Quantin et al., *Proc. Natl. Acad. Sci. USA,* 89:2581-2584, 1992; Stratford-Perricadet et al., *J. Clin. Invest.,* 90:626-630, 1992; and Rosenfeld et al., *Cell,* 68:143-155, 1992). For an example of the use of gene therapy in utero see U.S. Pat. No. 6,399,585.

Once transferred, the nucleic acid is expressed by the cells at the site of injury for a period of time sufficient to increase blood serum levels of a soluble endoglin binding protein. Because the vectors containing the nucleic acid are not normally incorporated into the genome of the cells, expression of the protein of interest takes place for only a limited time. Typically, the protein is expressed at therapeutic levels for about two days to several weeks, preferably for about one to two weeks. Re-application of the DNA can be utilized to provide additional periods of expression of the therapeutic protein.

Therapeutic Nucleic Acids that Inhibit Soluble Endoglin Expression

The present invention also features the use of antisense nucleobase oligomers to downregulate expression of soluble endoglin mRNA directly. By binding to the complementary nucleic acid sequence (the sense or coding strand), antisense nucleobase oligomers are able to inhibit protein expression presumably through the enzymatic cleavage of the RNA strand by RNAse H. Preferably the antisense nucleobase oligomer is capable of reducing soluble endoglin protein expression in a cell that expresses increased levels of soluble endoglin. Preferably the decrease in soluble endoglin protein expression is at least 10% relative to cells treated with a control oligonucleotide, preferably 20% or greater, more preferably 40%, 50%, 60%, 70%, 80%, 90% or greater. Methods for selecting and preparing antisense nucleobase oligomers are well known in the art. For an example of the use of antisense nucleobase oligomers to downregulate VEGF expression see U.S. Pat. No. 6,410,322, incorporated herein by reference. Methods for assaying levels of protein expression are also well known in the art and include western blotting, immunoprecipitation, and ELISA.

The present invention also features the use of RNA interference (RNAi) to inhibit expression of soluble endoglin. RNA interference (RNAi) is a recently discovered mechanism of post-transcriptional gene silencing (PTGS) in which double-stranded RNA (dsRNA) corresponding to a gene or mRNA of interest is introduced into an organism resulting in the degradation of the corresponding mRNA. In the RNAi reaction, both the sense and anti-sense strands of a dsRNA molecule are processed into small RNA fragments or segments ranging in length from 21 to 23 nucleotides (nt) and having 2-nucleotide 3' tails. Alternatively, synthetic dsRNAs, which are 21 to 23 nt in length and have 2-nucleotide 3' tails, can be synthesized, purified and used in the reaction. These 21 to 23 nt dsRNAs are known as "guide RNAs" or "short interfering RNAs" (siRNAs).

The siRNA duplexes then bind to a nuclease complex composed of proteins that target and destroy endogenous mRNAs having homology to the siRNA within the complex. Although the identity of the proteins within the complex remains unclear, the function of the complex is to target the homologous mRNA molecule through base pairing interactions between one of the siRNA strands and the endogenous mRNA. The mRNA is then cleaved approximately 12 nt from the 3' terminus of the siRNA and degraded. In this manner, specific genes can be targeted and degraded, thereby resulting in a loss of protein expression from the targeted gene. siRNAs can also be chemically synthesized or obtained from a company that chemically synthesizes siRNAs (e.g., Dharmacon Research Inc., Pharmacia, or ABI).

The specific requirements and modifications of dsRNA are described in PCT Publication No. WO01/75164 (incorporated herein by reference). While dsRNA molecules can vary in length, it is most preferable to use siRNA molecules which are 21- to 23-nucleotide dsRNAs with characteristic 2- to 3-nucleotide 3' overhanging ends typically either (2'-deoxy)thymidine or uracil. The siRNAs typically comprise a 3' hydroxyl group. Single stranded siRNA as well as blunt ended forms of dsRNA can also be used. In order to further enhance the stability of the RNA, the 3' overhangs can be stabilized against degradation. In one such embodiment, the RNA is stabilized by including purine nucleotides, such as adenosine or guanosine. Alternatively, substitution of pyrimidine nucleotides by modified analogs, e.g., substitution of uridine 2-nucleotide overhangs by (2'-deoxy)thymide is tolerated and does not affect the efficiency of RNAi. The absence of a 2' hydroxyl group significantly enhances the nuclease resistance of the overhang in tissue culture medium.

Alternatively siRNA can be prepared using any of the methods set forth in PCT Publication No. WO01/75164 (incorporated herein by reference) or using standard procedures for in vitro transcription of RNA and dsRNA annealing procedures as described in Elbashir et al. (*Genes & Dev.*, 15:188-200, 2001). siRNAs are also obtained as described in Elbashir et al., supra, by incubation of dsRNA that corresponds to a sequence of the target gene in a cell-free *Drosophila* lysate from syncytial blastoderm *Drosophila* embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs and the RNAs can then be eluted from the gel slices. In addition, chromatography (e.g., size exclusion chromatography), glycerol gradient centrifugation, and affinity purification with antibody can be used to isolate the 21 to 23 nt RNAs.

A variety of methods are available for transfection, or introduction, of dsRNA or oligonucleotides into mammalian cells. For example, there are several commercially available transfection reagents including but not limited to: TransIT-TKO™ (Mirus, Cat. # MIR 2150), Transmessenger™ (Qiagen, Cat. #301525), and Oligofectamine™ (Invitrogen, Cat. # MIR 12252-011). Protocols for each transfection reagent are available from the manufacturer.

In the present invention, the dsRNA, or siRNA, is complementary to the mRNA sequence of soluble endoglin mRNA and can reduce or inhibit expression of soluble endoglin. Preferably, the decrease in soluble endoglin protein expression is at least 10% relative to cells treated with a control dsRNA or siRNA, more preferably 25%, and most preferably at least 40%, 50%, 60%, 70%, 80%, 90%, or more. Methods for assaying levels of protein expression are also well known in the art and include western blotting, immunoprecipitation, and ELISA.

In the present invention, the nucleic acids used include any modification that enhances the stability or function of the nucleic acid in any way. Examples include modifications to the phosphate backbone, the internucleotide linkage, or to the sugar moiety.

Soluble Endoglin Based Therapeutic Compounds Useful in Early Pregnancy

Inhibition of full-length endoglin signaling has been shown to enhance trophoblast invasivness in villous explant cultures (Caniggia I et al, *Endocrinology*, 1997, 138:4977-88). Soluble endoglin is therefore likely to enhance trophoblast invasiveness during early pregnancy. Accordingly, compositions that increase soluble endoglin levels early in pregnancy in a woman who does not have a pregnancy related hypertensive disorder or a predisposition to a pregnancy related hypertensive disorder may be beneficial for enhancing placentation. Examples of compositions that increase soluble endoglin levels include purified soluble endoglin polypeptides, soluble endoglin encoding nucleic acid molecules, and compounds or growth factors that increase the levels or biological activity of soluble endoglin.

Assays for Gene and Protein Expression

The following methods can be used to evaluate protein or gene expression and determine efficacy for any of the above-mentioned methods for increasing soluble endoglin binding protein levels, or for decreasing soluble endoglin protein levels.

Blood serum from the subject is measured for levels of soluble endoglin, using methods such as ELISA, western blotting, or immunoassays using specific antibodies. Blood serum from the subject can also be measured for levels of TGF-β1, TGF-β3, activin-A, BMP2, BMP7, or any protein ligand known to bind to soluble endoglin. Methods used to measure serum levels of proteins include ELISA, western blotting, or immunoassays using specific antibodies. In addition, in vitro angiogenesis assays can be performed to determine if the subject's blood has converted from an anti-angiogenic state to a pro-angiogenic state. Such assays are described above in Example 4. A positive result is considered an increase of at least 10%, 20%, preferably 30%, more preferably at least 40% or 50%, and most preferably at least 60%, 70%, 80%, 90% or more in the levels of soluble endoglin, TGF-β1, TGF-β3, activin-A, BMP2, BMP7, or any protein ligand known to bind to soluble endoglin. A positive result can also be considered conversion by at least 10%, preferably 20%, 30%, 40%, 50%, and most preferably at least 60%, 70%, 80%, 90% or more from an anti-angiogenic state to a pro-angiogenic state using the in vitro angiogenesis assay.

Blood serum or urine samples from the subject can also be measured for levels of nucleic acids or polypeptides encoding TGF-β1, TGF-β3, activin-A, BMP2, BMP7, or soluble endoglin. There are several art-known methods to assay for gene expression. Some examples include the preparation of RNA from the blood samples of the subject and the use of the RNA for northern blotting, PCR based amplification, or RNAse protection assays. A positive result is considered an increase of at least 10%, 20%, preferably 30%, more preferably at least 40% or 50%, and most preferably at least 60%, 70%, 80%, 90% or more in the levels of soluble endoglin, TGF-β1, TGF-β3, activin-A, BMP2, BMP7 nucleic acids.

Use of Antibodies for Therapeutic Treatment

The elevated levels of soluble endoglin found in the serum samples taken from pregnant women suffering from pre-eclampsia suggests that soluble endoglin is acting as a "physiologic sink" to bind to and deplete the trophoblast cells and maternal endothelial cells of functional growth factors required for the proper development and angiogenesis of the fetus or the placenta. The use of compounds, such as antibodies, to bind to soluble endoglin and neutralize the activity of soluble endoglin (e.g., binding to TGF-β1, TGF-β3, activin-A, BMP2, BMP7), may help prevent or treat pre-eclampsia or eclampsia, by producing an increase in free TGF-β1, TGF-β3, activin-A, BMP2, and BMP7. Such an increase would allow for an increase in trophoblast proliferation, migration and angiogenesis required for placental development and fetal nourishment, and for systemic maternal endothelial cell health.

The present invention provides antibodies that bind specifically to the ligand-binding domain of soluble endoglin. The antibodies are used to neutralize the activity of soluble endoglin and the most effective mechanism is believed to be through direct blocking of the binding sites for TGF-β1, TGF-β3, activin-A, BMP2, or BMP7, however, other mechanisms cannot be ruled out. Methods for the preparation and use of antibodies for therapeutic purposes are described in several patents including U.S. Pat. Nos. 6,054, 297; 5,821,337; 6,365,157; and 6,165,464 and are incorporated herein by reference. Antibodies can be polyclonal or monoclonal; monoclonal antibodies are preferred.

Monoclonal antibodies, particularly those derived from rodents including mice, have been used for the treatment of various diseases; however, there are limitations to their use including the induction of a human anti-mouse immunoglobulin response that causes rapid clearance and a reduction in the efficacy of the treatment. For example, a major limitation in the clinical use of rodent monoclonal antibodies is an anti-globulin response during therapy (Miller et al., *Blood*, 62:988-995 1983; Schroff et al., *Cancer Res.*, 45:879-885, 1985).

The art has attempted to overcome this problem by constructing "chimeric" antibodies in which an animal antigen-binding variable domain is coupled to a human constant domain (U.S. Pat. No. 4,816,567; Morrison et al., *Proc. Natl. Acad. Sci. USA*, 81:6851-6855, 1984; Boulianne et al., *Nature*, 312:643-646, 1984; Neuberger et al., *Nature*, 314: 268-270, 1985). The production and use of such chimeric antibodies are described below.

Competitive inhibition of ligand binding to soluble endoglin is useful for the prevention or treatment of pre-eclampsia or eclampsia. Such an increase can result in a rescue of endothelial dysfunction and a shift in the balance of pro-angiogenic/anti-angiogenic factors towards angiogenesis.

A cocktail of the monoclonal antibodies of the present invention can be used as an effective treatment for pre-eclampsia or eclampsia. The cocktail may include as few as two, three, or four different antibodies or as many as six, eight, or ten different antibodies. In addition, the antibodies of the present invention can be combined with an antihypertensive drug (e.g., methyldopa, hydralazine hydrochloride, or labetalol) or any other medication used to treat pre-eclampsia, eclampsia, or the symptoms associated with pre-eclampsia or eclampsia.

Preparation of Antibodies

Monoclonal antibodies that specifically bind to the sFlt-1 receptor may be produced by methods known in the art. These methods include the immunological method described by Kohler and Milstein (*Nature*, 256: 495-497, 1975) and Campbell ("Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam, 1985), as well as by the recombinant DNA method described by Huse et al. (*Science*, 246, 1275-1281, 1989).

Monoclonal antibodies may be prepared from supernatants of cultured hybridoma cells or from ascites induced by intra-peritoneal inoculation of hybridoma cells into mice. The hybridoma technique described originally by Kohler and Milstein (*Eur. J. Immunol*, 6, 511-519, 1976) has been widely applied to produce hybrid cell lines that secrete high levels of monoclonal antibodies against many specific antigens.

The route and schedule of immunization of the host animal or cultured antibody-producing cells therefrom are generally in keeping with established and conventional techniques for antibody stimulation and production. Typically, mice are used as the test model, however, any mammalian subject including human subjects or antibody producing cells therefrom can be manipulated according to the processes of this invention to serve as the basis for production of mammalian, including human, hybrid cell lines.

After immunization, immune lymphoid cells are fused with myeloma cells to generate a hybrid cell line that can be cultivated and subcultivated indefinitely, to produce large quantities of monoclonal antibodies. For purposes of this invention, the immune lymphoid cells selected for fusion are lymphocytes and their normal differentiated progeny, taken either from lymph node tissue or spleen tissue from immunized animals. The use of spleen cells is preferred, since they offer a more concentrated and convenient source of antibody producing cells with respect to the mouse system. The myeloma cells provide the basis for continuous propagation of the fused hybrid. Myeloma cells are tumor cells derived from plasma cells. Murine myeloma cell lines can be obtained, for example, from the American Type Culture Collection (ATCC; Manassas, Va.). Human myeloma and mouse-human heteromyeloma cell lines have also been described (Kozbor et al., *J. Immunol.,* 133:3001-3005, 1984; Brodeur et al., Monoclonal Antibody Production Techniques and Applications, Marcel Dekker, Inc., New York, pp. 51-63, 1987).

The hybrid cell lines can be maintained in vitro in cell culture media. Once the hybridoma cell line is established, it can be maintained on a variety of nutritionally adequate media such as hypoxanthine-aminopterin-thymidine (HAT) medium. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, ion exchange chromotography, affinity chromatography, or the like.

The antibody may be prepared in any mammal, including mice, rats, rabbits, goats, and humans. The antibody may be a member of one of the following immunoglobulin classes: IgG, IgM, IgA, IgD, or IgE, and the subclasses thereof, and preferably is an IgG antibody.

While the preferred animal for producing monoclonal antibodies is mouse, the invention is not so limited; in fact, human antibodies may be used and may prove to be preferable. Such antibodies can be obtained by using human hybridomas (Cole et al., "Monoclonal Antibodies and Cancer Therapy", Alan R. Liss Inc., p. 77-96, 1985). In the present invention, techniques developed for the production of chimeric antibodies by splicing the genes from a mouse antibody molecule of appropriate antigen specificity together with genes from a human antibody molecule can be used (Morrison et al., *Proc. Natl. Acad. Sci.* 81, 6851-6855, 1984; Neuberger et al., *Nature* 312, 604-608, 1984; Takeda et al., *Nature* 314, 452-454, 1985); such antibodies are within the scope of this invention and are described below.

As another alternative to the cell fusion technique, Epstein-Barr virus (EBV) immortalized B cells are used to produce the monoclonal antibodies of the present invention (Crawford et al., *J. Gen. Virol.,* 64:697-700, 1983; Kozbor and Roder, *J. Immunol.,* 4:1275-1280, 1981; Kozbor et al., *Methods Enzymol.,* 121:120-140, 1986). In general, the procedure consists of isolating Epstein-Barr virus from a suitable source, generally an infected cell line, and exposing the target antibody secreting cells to supernatants containing the virus. The cells are washed, and cultured in an appropriate cell culture medium. Subsequently, virally transformed cells present in the cell culture can be identified by the presence of the Epstein-Barr viral nuclear antigen, and transformed antibody secreting cells can be identified using standard methods known in the art. Other methods for producing monoclonal antibodies, such as recombinant DNA, are also included within the scope of the invention.

Preparation of Soluble Endoglin Immunogens

Soluble endoglin may be used by itself as an immunogen, or may be attached to a carrier protein or to other objects, such as sepharose beads. Soluble endoglin may be purified from cells known to express the endogenous protein such as human umbilical vein endothelial cells (trophoblasts or HUVEC; Burrows et al., *Clin. Cancer Res.* 1:1623-1634, 1995; Fonsatti et al., *Clin. Cancer Res.* 6:2037-2043, 2000). Cells that express membrane bound endoglin can be treated with a proteolytic enzyme (e.g., a matrix metalloproteinase) to cleave the extracellular domain, thereby producing the soluble form. Additionally, nucleic acid molecules that encode soluble endoglin, or portions thereof, can be inserted into known vectors for expression in host cells using standard recombinant DNA techniques. Suitable host cells for soluble endoglin expression include baculovirus cells (e.g., Sf9 cells), bacterial cells (e.g., *E. coli*), and mammalian cells (e.g., NIH3T3 cells).

In addition, peptides can be synthesized and used as immunogens. The methods for making antibody to peptides are well known in the art and generally require coupling the peptide to a suitable carrier molecule, such as serum albumin. Peptides include any amino acid sequence that is substantially identical to any part of the soluble endoglin amino acid sequence corresponding to GenBank accession numbers AAH29080 and NP_031958 (mouse); AAS67893 (rat); NP_000109, P17813, VSP_004233, and CAA80673 (human); and A49722 (pig). Peptides can be any length, preferably 10 amino acids or greater, more preferably 25 amino acids or greater, and most preferably 40, 50, 60, 70, 80, 100, 200, 300, 400, 437 amino acids or greater. Preferably, the amino acid sequences are at least 60%, more preferably 85%, and, most preferably 90%, 95%, 96%, 97%, 98%, 99% or 100% identical to the sequence of any of the human endoglin sequences. The peptides can be commercially obtained or made using techniques well known in the art, such as, for example, the Merrifield solid-phase method (*Science,* 232:341-347, 1985). The procedure may use commercially available synthesizers such as a Biosearth 9500 automated peptide machine, with cleavage of the blocked amino acids being achieved with hydrogen fluoride, and the peptides purified by preparative HPLC using a Waters Delta Prep 3000 instrument, on a 15-20 µm Vydac C4 PrepPAK column.

Functional Equivalents of Antibodies

The invention also includes functional equivalents of the antibodies described in this specification. Functional equivalents include polypeptides with amino acid sequences substantially identical to the amino acid sequence of the variable or hypervariable regions of the antibodies of the invention. Functional equivalents have binding characteristics comparable to those of the antibodies, and include, for example, chimerized, humanized and single chain antibodies as well as fragments thereof. Methods of producing such functional equivalents are disclosed, for example, in PCT Publication No. WO93/21319; European Patent Application No. 239,400; PCT Publication No. WO89/09622; European Patent Application No. 338,745; European Patent Application No. 332424; and U.S. Pat. No. 4,816,567; each of which is herein incorporated by reference.

Chimerized antibodies preferably have constant regions derived substantially or exclusively from human antibody constant regions and variable regions derived substantially or exclusively from the sequence of the variable region from a mammal other than a human. Such humanized antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Methods for humanizing non-human antibodies are well known in the art (for reviews see Vaswani and Hamilton, *Ann. Allergy Asthma Immunol.*, 81:105-119, 1998 and Carter, *Nature Reviews Cancer*, 1:118-129, 2001). Generally, a humanized antibody has one or more amino acid residues introduced into it from a source that is non-human. These non-human amino acid residues are often referred to as import residues, which are typically taken from an import variable domain. Humanization can be essentially performed following the methods known in the art (Jones et al., *Nature*, 321:522-525, 1986; Riechmann et al., *Nature*, 332: 323-329, 1988; and Verhoeyen et al., *Science*, 239:1534-1536 1988), by substituting rodent CDRs or other CDR sequences for the corresponding sequences of a human antibody. Accordingly, such humanized antibodies are chimeric antibodies wherein substantially less than an intact human variable domain has been substituted by the corresponding sequence from a non-human species (see for example, U.S. Pat. No. 4,816,567). In practice, humanized antibodies are typically human antibodies in which some CDR residues and possibly some FR residues are substituted by residues from analogous sites in rodent antibodies (Presta, *Curr. Op. Struct. Biol.*, 2:593-596, 1992).

Additional methods for the preparation of humanized antibodies can be found in U.S. Pat. Nos. 5,821,337, and 6,054,297, and Carter, (supra) which are all incorporated herein by reference. The humanized antibody is selected from any class of immunoglobulins, including IgM, IgG, IgD, IgA and IgE, and any isotype, including $IgG_1$, $IgG_2$, $IgG_3$, and $IgG_4$. Where cytotoxic activity is not needed, such as in the present invention, the constant domain is preferably of the $IgG_2$ class. The humanized antibody may comprise sequences from more than one class or isotype, and selecting particular constant domains to optimize desired effector functions is within the ordinary skill in the art.

Human antibodies can also be produced using various techniques known in the art, including phage display libraries (Marks et al., *J. Mol. Biol.*, 222:581-597, 1991 and Winter et al. *Annu. Rev. Immunol.*, 12:433-455, 1994). The techniques of Cole et al. and Boerner et al. are also useful for the preparation of human monoclonal antibodies (Cole et al., supra; Boerner et al., *J. Immunol.*, 147: 86-95, 1991).

Suitable mammals other than a human include any mammal from which monoclonal antibodies may be made. Examples of mammals other than a human include, for example a rabbit, rat, mouse, horse, goat, or primate; a mouse is preferred.

Functional equivalents of antibodies also include single-chain antibody fragments, also known as single-chain antibodies (scFvs). Single-chain antibody fragments are recombinant polypeptides which typically bind antigens or receptors; these fragments contain at least one fragment of an antibody variable heavy-chain amino acid sequence ($V_H$) tethered to at least one fragment of an antibody variable light-chain sequence ($V_L$) with or without one or more interconnecting linkers. Such a linker may be a short, flexible peptide selected to assure that the proper three-dimensional folding of the $V_L$ and $V_H$ domains occurs once they are linked so as to maintain the target molecule binding-specificity of the whole antibody from which the single-chain antibody fragment is derived. Generally, the carboxyl terminus of the $V_L$ or $V_H$ sequence is covalently linked by such a peptide linker to the amino acid terminus of a complementary $V_L$ and $V_H$ sequence. Single-chain antibody fragments can be generated by molecular cloning, antibody phage display library or similar techniques. These proteins can be produced either in eukaryotic cells or prokaryotic cells, including bacteria.

Single-chain antibody fragments contain amino acid sequences having at least one of the variable regions or CDRs of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient.

Functional equivalents further include fragments of antibodies that have the same or comparable binding characteristics to those of the whole antibody. Such fragments may contain one or both Fab fragments or the $F(ab')_2$ fragment. Preferably the antibody fragments contain all six CDRs of the whole antibody, although fragments containing fewer than all of such regions, such as three, four or five CDRs, are also functional.

Further, the functional equivalents may be or may combine members of any one of the following immunoglobulin classes: IgG, IgM, IgA, IgD, or IgE, and the subclasses thereof.

Preparation of Functional Equivalents of Antibodies

Equivalents of antibodies are prepared by methods known in the art. For example, fragments of antibodies may be prepared enzymatically from whole antibodies. Preferably, equivalents of antibodies are prepared from DNA encoding such equivalents. DNA encoding fragments of antibodies may be prepared by deleting all but the desired portion of the DNA that encodes the full-length antibody.

DNA encoding chimerized antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions other than the CDRs derived substantially or exclusively from the corresponding human antibody regions and DNA encoding CDRs derived substantially or exclusively from a mammal other than a human.

Suitable sources of DNA molecules that encode fragments of antibodies include cells, such as hybridomas, that express the full-length antibody. The fragments may be used by themselves as antibody equivalents, or may be recombined into equivalents, as described above.

The DNA deletions and recombinations described in this section may be carried out by known methods, such as those described in the published patent applications listed above.

Antibody Screening and Selection

Monoclonal antibodies are isolated and purified using standard art-known methods. For example, antibodies can be screened using standard art-known methods such as ELISA against the soluble endoglin peptide antigen or western blot analysis. Non-limiting examples of such techniques are described in Examples II and III of U.S. Pat. No. 6,365,157, herein incorporated by reference.

Therapeutic Uses of Antibodies

When used in vivo for the treatment or prevention of pre-eclampsia or eclampsia, the antibodies of the subject invention are administered to the subject in therapeutically effective amounts. Preferably, the antibodies are administered parenterally or intravenously by continuous infusion. The dose and dosage regimen depends upon the severity of the disease, and the overall health of the subject. The amount of antibody administered is typically in the range of about 0.001 to about 10 mg/kg of subject weight, preferably 0.01 to about 5 mg/kg of subject weight.

For parenteral administration, the antibodies are formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibodies typically are formulated in such vehicles at concentrations of about 1 mg/ml to 10 mg/ml.

Combination Therapies

Optionally, a pre-eclampsia or eclampsia therapeutic may be administered in combination with any other standard pre-eclampsia or eclampsia therapy; such methods are known to the skilled artisan and include the methods described in U.S. Patent Application Publication Numbers 20040126828, 20050025762, and 2005017044 and PCT Publication Numbers WO 2004/008946 and WO 2005/077007.

Dosages and Modes of Administration

Preferably, the therapeutic is administered during pregnancy for the treatment or prevention of pre-eclampsia or eclampsia or after pregnancy to treat post-partum pre-eclampsia or eclampsia. Techniques and dosages for administration vary depending on the type of compound (e.g., chemical compound, purified protein, antibody, antisense, RNAi, or nucleic acid vector) and are well known to those skilled in the art or are readily determined.

Therapeutic compounds of the present invention may be administered with a pharmaceutically acceptable diluent, carrier, or excipient, in unit dosage form. Administration may be parenteral, intravenous, subcutaneous, oral or local by direct injection into the amniotic fluid. Intravenous delivery by continuous infusion is the preferred method for administering the therapeutic compounds of the present invention.

The composition can be in the form of a pill, tablet, capsule, liquid, or sustained release tablet for oral administration; or a liquid for intravenous, subcutaneous or parenteral administration; or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.).

Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The compound may be optionally administered as a pharmaceutically acceptable salts, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The dosage and the timing of administering the compound depends on various clinical factors including the overall health of the subject and the severity of the symptoms of pre-eclampsia. In general, once pre-eclampsia or a predisposition to pre-eclampsia is detected, continuous infusion of the purified protein is used to treat or prevent further progression of the condition. Treatment can be continued for a period of time ranging from 1 to 100 days, more preferably 1 to 60 days, and most preferably 1 to 20 days, or until the completion of pregnancy. Dosages vary depending on each compound and the severity of the condition and are titrated to achieve a steady-state blood serum concentration ranging from 10 to 20 ng/ml soluble endoglin; and/or 1 to 500 pg/mL free VEGF or free PlGF, or both, preferably 1 to 100 pg/mL, more preferably 5 to 50 pg/mL and most preferably 5 to 10 pg/mL VEGF or PlGF, or 1-5 ng of sFlt-1.

The diagnostic methods described herein can be used to monitor the pre-eclampsia or eclampsia during therapy or to determine the dosages of therapeutic compounds. In one example, a therapeutic compound is administered and the PAAI is determined during the course of therapy. If the PAAI is less than 20, preferably less than 10, then the therapeutic dosage is considered to be an effective dosage. In another example, a therapeutic compound is administered and the soluble endoglin anti-angiogenic index is determined during the course of therapy. If the soluble endoglin anti-angiogenic index is less than 200, preferably less than 100, then the therapeutic dosage is considered to be an effective dosage.

Subject Monitoring

The disease state or treatment of a subject having pre-eclampsia, eclampsia, or a predisposition to such a condition can be monitored using the methods and compositions of the invention. For example, the expression of a soluble endoglin polypeptide present in a bodily fluid, such as urine, plasma, amniotic fluid, or CSF, is monitored. The soluble endoglin monitoring can be combined with methods for monitoring the expression of an sFlt-1, VEGF, or PlGF polypeptide. Such monitoring may be useful, for example, in assessing the efficacy of a particular drug in a subject or in assessing disease progression. Therapeutics that decrease the expression of a soluble endoglin nucleic acid molecule or polypeptide are taken as particularly useful in the invention.

EXAMPLES

The following examples are intended to illustrate the invention. They are not meant to limit the invention in any way.

Example 1

Increased Levels of Endoglin mRNA and Protein in Pregnant Women with Pre-eclampsia In an attempt to identify novel secreted factors playing a pathologic role in pre-eclampsia, we performed gene expression profiling of placental tissue from 17 pregnant women with pre-eclampsia and 13 normal pregnant women using Affymetrix U95A microarray chips. We found that the gene for endoglin was upregulated in women with pre-eclampsia.

Figure 3:
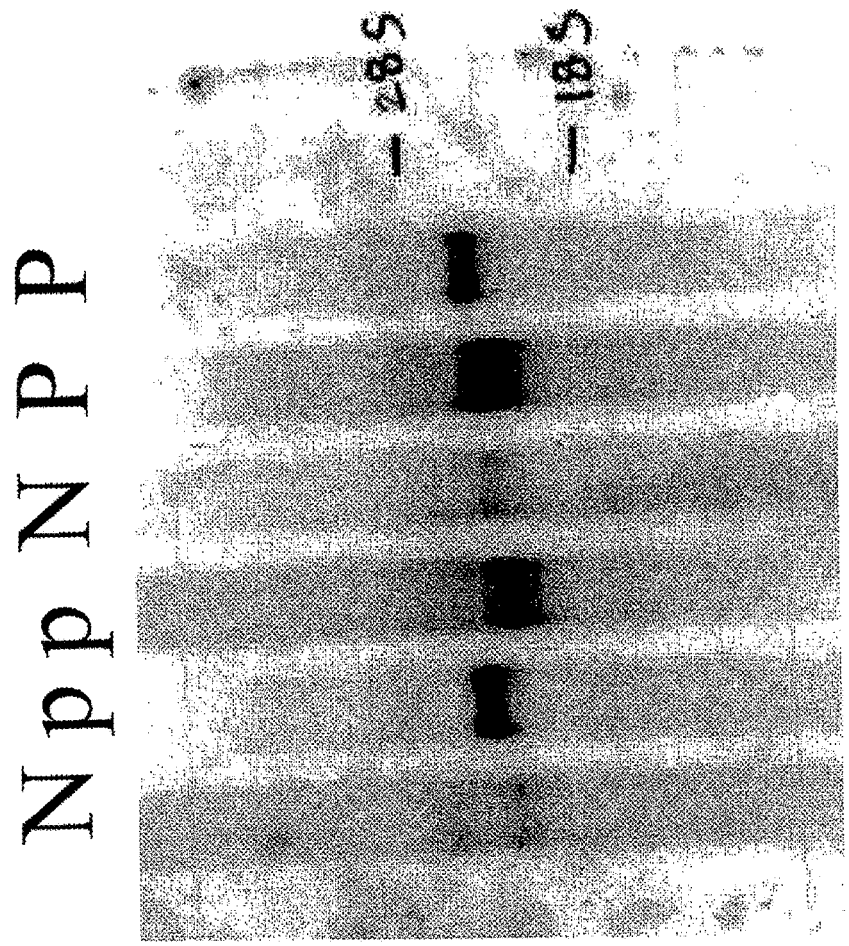
FIG. 3 is a Northern blot showing endoglin mRNA levels in placentas from normal pregnancies (N), placentas from mild pre-eclamptic pregnancies (p) and placentas from severe pre-eclamptic pregnancies (P).
Figure 4:
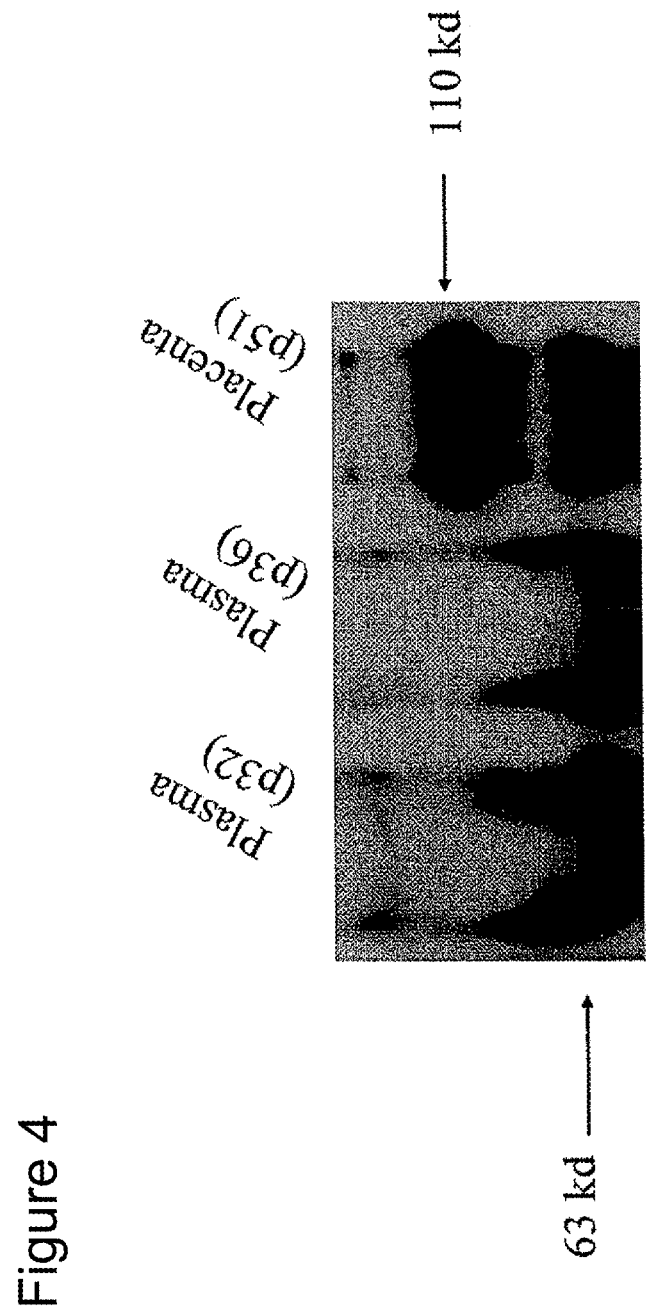
FIG. 4 is a western blot showing endoglin protein levels in the placenta. Samples are from two pre-eclamptic patients, p32 and p36, that presented to the Beth Israel Deaconess Medical Center in 2003 and maternal serum from a pregnant woman. The Western blot was probed using a N-terminal antibody obtained from Santa Cruz Biotechnology, Inc., (Santa Cruz, Calif.) that shows both the 110 kD band in the placenta and a smaller 63 kD band that is present in the placenta and the serum samples.

In order to confirm the upregulation of endoglin in pre-eclampsia, we performed Northern blots to analyze the placental endoglin mRNA levels (FIG. 3) and western blot analysis to measure serum protein levels of endoglin (FIG. 4) in pre-eclamptic pregnant women as compared with normotensive pregnant women. Pre-eclampsia was defined as (1) a systolic blood pressure (BP)>140 mmHg and a diastolic BP>90 mmHg after 20 weeks gestation, (2) new onset proteinuria (1+ by dipstik on urinalysis, >300 mg of protein in a 24 hour urine collection, or random urine protein/creatinine ratio >0.3, and (3) resolution of hypertension and proteinuria by 12 weeks postpartum. Patients with underlying hypertension, proteinuria, or renal disease were excluded. Patients were divided into mild and severe pre-eclampsia based on the presence or absence of nephritic range proteinuria (>3 g of protein on a 24 hour urine collection or urine protein/creatinine ratio greater than 3.0). The mean urine protein/creatinine ratios in the mild pre-eclampsia group were 0.94+/−0.2 and in the severe pre-eclampsia group were 7.8+/−2.1. The mean gestational ages of the various groups were as follows: normal 38.8+/−0.2 weeks, mild pre-eclampsia 34+/−1.2 weeks, severe pre-eclampsia 31.3+/−0.6 weeks, and pre-term 29.5+/−2.0 weeks. Placental samples were obtained immediately after delivery. Four random samples were taken from each placenta, placed in RNAlater stabilization solution (Ambion, Austin, Tex.) and stored at −70° C. RNA isolation was performed using Qiagen RNAeasy Maxi Kit (Qiagen, Valencia, Calif.).

Northern blots probed with a 400 base pair probe in the coding region of endoglin (Unigene Hs.76753) and a GAPDH probe as a normalization control showed an increase in placental endoglin mRNA. Western blots probed with an antibody to the amino terminus of endoglin showed an increase in both placental and maternal serum levels of endoglin protein in pre-eclamptic pregnant women as compared to normotensive pregnant women.

Example 2

Demonstration of a Soluble Endoglin Polypeptide in the Placentas and Serum of Pre-eclamptic Patients The western blot analysis used to measure the levels of endoglin protein in placentas and serum from pre-eclamptic women suggested the presence of a smaller protein (63 kDa), that was present in the placenta and serum of pre-eclamptic pregnant women. We have demonstrated that this smaller fragment is the extracellular domain of endoglin. This truncated version is likely to be shed from the placental syncitiotrophoblasts and endothelial cells and circulated in excess quantities in patients with pre-eclampsia. This soluble form of endoglin may be acting as an anti-angiogenic agent by binding to circulating ligands that are necessary for normal vascular health.

Example 3

Figure 5:
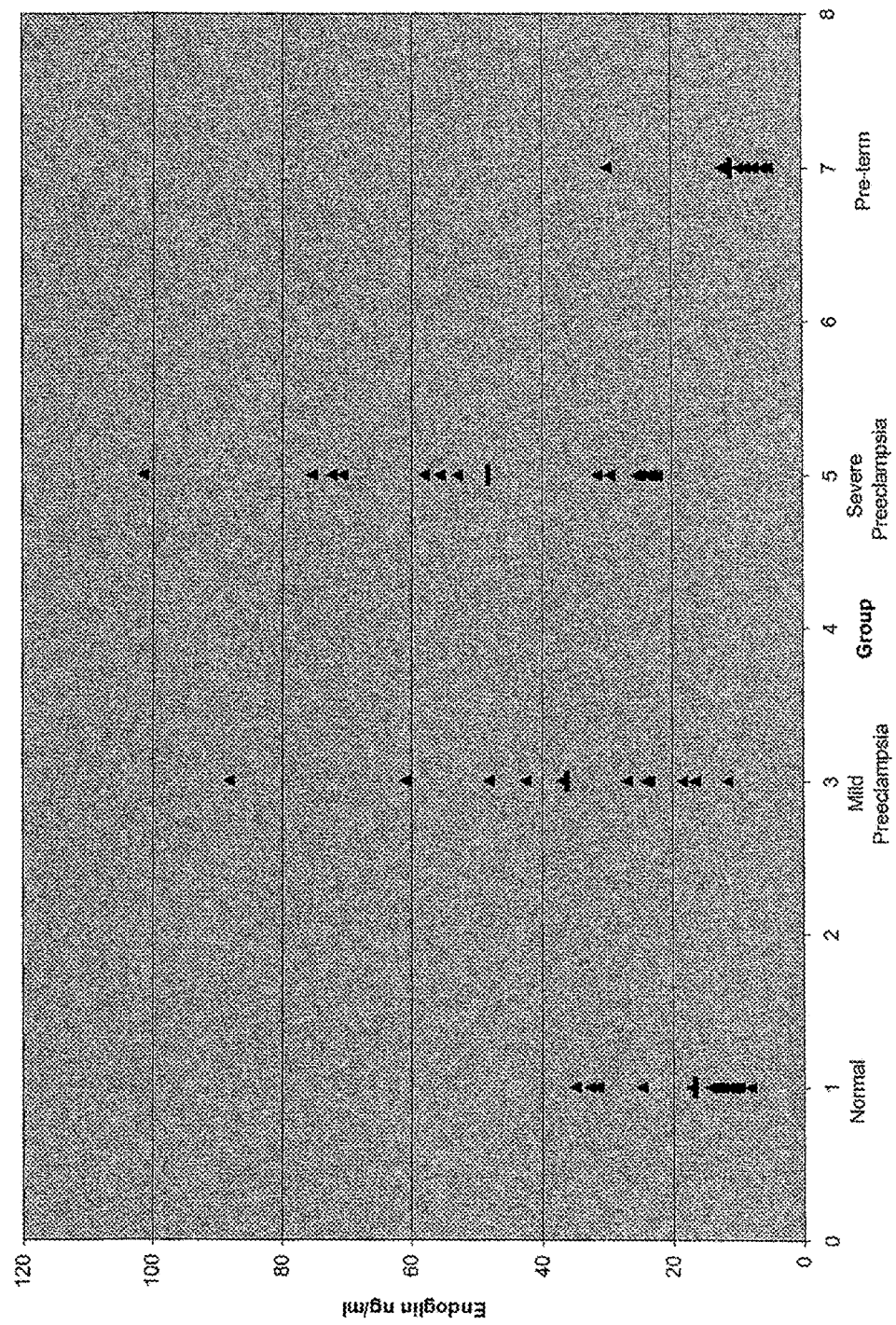
FIG. 5 is a graph that shows the circulating concentrations of soluble endoglin in women with normal pregnancy, mild pre-eclampsia, severe pre-eclampsia and non-pre-eclamptic pregnancies complicated by pre-term delivery. All blood specimens were obtained within 24 hours prior to delivery. Soluble endoglin was measured using an ELISA kit from R & D Systems, MN (Cat # DNDG00). These data show that soluble endoglin levels are significantly elevated in pre-eclamptic patients at the time of clinical disease.

Circulating Concentrations of Soluble Endoglin in Women with Normal Versus Pre-eclamptic Pregnancies In order to compare the levels of circulating, soluble endoglin from the serum of normal, mildly pre-eclamptic, or severely pre-eclamptic women, we performed ELISA analysis on blood samples taken from these women. Patients were divided into mild and severe pre-eclampsia based on the presence or absence of nephritic range proteinuria (>3 g of protein on a 24 hour urine collection or urine protein/creatinine ratio greater than 3.0). The mean urine protein/creatinine ratios in the mild pre-eclampsia group were 0.94+/−0.2 and in the severe pre-eclampsia group were 7.8+/−2.1 (FIG. 5). ELISA was performed using a commercially available ELISA kit from R & D Systems, MN (Cat # DNDG00) as previously described (Maynard et al, *J. Clin. Invest.* 111:649-658, 2003).

Example 4

Model Assay for Angiogenesis

An endothelial tube assay can be used an in vitro model of angiogenesis. Growth factor reduced Matrigel (7 mg/mL, Collaborative Biomedical Products, Bedford, Mass.) is placed in wells (100 μl/well) of a pre-chilled 48-well cell culture plate and is incubated at 37° C. for 25-30 minutes to allow polymerization. Human umbilical vein endothelial cells (30,000+ in 300 μl of endothelial basal medium with no serum, Clonetics, Walkersville, Md.) at passages 3-5 are treated with 10% patient serum, plated onto the Matrigel coated wells, and are incubated at 37° C. for 12-16 hours. Tube formation is then assessed through an inverted phase contrast microscope at 4× (Nikon Corporation, Tokyo, Japan) and is analyzed (tube area and total length) using the Simple PCI imaging analysis software.

Example 5

Soluble Endoglin Protein Levels as a Diagnostic Indicator of Pre-eclampsia and Eclampsia in Women (Romero Study)

This study was designed to evaluate whether soluble endoglin is altered during clinical pre-eclampsia and whether it can be used to predict pre-eclampsia and eclampsia in women.

This study was done under collaboration with Dr. Roberto Romero, at the Wayne State University/NICHD Perinatology Branch, Detroit, Mich. A retrospective longitudinal case-control study was conducted using a banked biological sample database as previously described in Chaiworapongsa et al. (The Journal of Maternal-Fetal and Neonatal Medicine, Jan. 2005, 17 (1):3-18). All women were enrolled in the prenatal clinic at the Sotero del Rio Hospital, Santiago, Chile, and followed until delivery. Prenatal visits were scheduled at 4-week intervals in the first and second trimester, and every two weeks in the third trimester until delivery. Plasma samples were selected from each patient only once for each of the following six intervals: (1) 7-16 weeks, (2) 16-24 weeks, (3) 24-28 weeks, (4) 28-32 weeks, (5) 32-37 weeks, and (6) >37 weeks of gestation. For each pre-eclamptic case, one control was selected by matching for gestational age (+/−2 weeks) at the time of clinical diagnosis of pre-eclampsia. The clinical criteria for the diagnosis of pre-eclampsia were the same as previously described in Chaiworapongsa et al, supra.

Measurement of Plasma Endoglin Levels

The plasma samples stored at −70° C. were thawed and plasma soluble endoglin levels were measured in one batch using the commercially available ELISA kits from R&D systems, Minneapolis, Minn. (Catalog # DNDG00).

Statistical Analysis

Analysis of covariance was used to assess the difference in plasma concentrations of soluble endoglin between patients destined to develop pre-eclampsia and in normal pregnancy after adjusting for gestational age at blood sampling and intervals of sample storage. Chi-square or Fisher's exact tests were employed for comparisons of proportions. The statistics package used was SPSS V.12 (SPSS Inc., Chicago, Ill.). Significance was assumed for a p value of less than 0.05.

Results

The clinical characteristics of the study population are described in Table 1. The group with pre-eclampsia included more nulliparous women and delivered earlier than the control group. Importantly, the birth weights of the fetuses were smaller in the pre-eclamptic group and there were a higher proportion of women carrying small-for-gestational-age (SGA) infants.

TABLE 1

Clinical characteristics of the study population

| | Normal pregnancy n = 44 | Pre-eclampsia n = 44 | p |
|---|---|---|---|
| Age (y) | 29 ± 6 | 26 ± 6 | 0.04* |
| Nulliparity | 11 (25%) | 30 (68.2%) | <0.001* |
| Smoking | 10 (22.7%) | 1 (2.3%) | 0.007* |
| GA at delivery (weeks) | 39.7 ± 1.1 | 36.9 ± 2.7 | <0.001* |
| Birthweight (grams) | 3,372 ± 383 | 2,710 ± 766 | <0.001* |
| Birthweight <10$^{th}$ percentile | 0 | 16 (36.4%) | <0.001* |

Value expressed as mean ± sd or number (percent)
GA: gestational age

The clinical characteristics of patients with pre-eclampsia are described in Table 2. Thirty-two (72%) of the patients had severe pre-eclampsia, while 10 patients had severe early-onset pre-eclampsia defined as onset <34 weeks.

TABLE 2

Clinical characteristics of patients with pre-eclampsia

| Blood pressure (mmHg) | |
|---|---|
| Systolic | 155 ±15 |
| Diastolic | 100 ± 8 |
| Mean arterial pressure | 118 ± 9 |
| Proteinuria (dipstick) | 3 ± 0.8 |
| Aspartate aminotransferase$^\alpha$ (SGOT) (U/L) | 29 ± 31 |
| Platelet count$^\beta$ (×10$^3$) (μ/L) | 206 ± 59 |
| Severe pre-eclampsia | 32 (72.7%) |
| GA at pre-eclampsia diagnosed ≤34 weeks | 10 (22.7%) |
| GA at pre-eclampsia diagnosed ≥37 weeks | 27 (61.4%) |

Value expressed as mean ± sd or number (percent)
$^\alpha$(n = 26);
$^\beta$(n = 42)

The serum soluble endoglin levels in the controls and the pre-eclamptic women measured in the 6 gestational age windows are shown in Table 3. Amongst the pre-eclamptics, their specimens were divided into two groups—clinical pre-eclampsia (samples taken at the time of symptoms of pre-eclampsia) and preclinical pre-eclampsia (samples taken prior to clinical symptoms). The data shows that at midpregnancy (24-28 weeks of gestation), serum soluble endoglin concentrations start rising in women destined to develop pre-eclampsia and become at least 3 fold higher than controls by 28-32 weeks of gestation. Blood samples taken from women with clinical pre-eclampsia show a very dramatic (nearly 10-15 fold) elevation when compared to gestational age matched controls.

TABLE 3

Plasma soluble endoglin concentrations in normal pregnancy and pre-eclampsia

| | Normal pregnancy | p | Pre-clinical samples Pre-eclampsia | p | Clinical samples Pre-eclampsia | p$^\beta$ |
|---|---|---|---|---|---|---|
| 1$^{st}$ blood sampling (7.1-16 weeks) | | | | | | |
| Soluble Endoglin (ng/ml) | 3.89 ± .928 | 0.9 | 3.96 ± 1.28 | | | |
| Gestational age (weeks) | 12.3 ± 2.2 | 0.2 | 11.6 ± 2.4 | | | |
| Range | 8.4-15.9 | | 7.7-15.1 | | | |
| | n = 37 | | n = 34 | | | |

TABLE 3-continued

Plasma soluble endoglin concentrations in normal pregnancy and pre-eclampsia

|  | Normal pregnancy | p | Pre-clinical samples Pre-eclampsia | p | Clinical samples Pre-eclampsia | $p^\beta$ |
|---|---|---|---|---|---|---|
| $2^{nd}$ blood sampling (16.1-24 weeks) | | | | | | |
| Soluble Endoglin (ng/ml) | 3.36 ± 1.11 | 0.1 | 3.79 ± 1.37 | | | |
| Gestational age (weeks) | 19.4 ± 1.7 | 0.06 | 20.2 ± 2.1 | | | |
| Range | 16.3-23.4 | | 16.7-24.0 | | | |
|  | n = 44 | | n = 36 | | | |
| $3^{rd}$ blood sampling (24.1-28 weeks) | | | | | | |
| Soluble Endoglin (ng/ml) | 3.18 ± .729 | 0.009* | 5.27 ± 4.12 | | | |
| Gestational age (weeks) | 25.9 ± 1.3 | 0.2 | 26.4 ± 1.1 | | | |
| Range | 24.1-28.0 | | 24.6-28.0 | | | |
|  | n = 38 | | n = 29 | | | |
| $4^{th}$ blood sampling (28.1-32 weeks) | | | | | | |
| Soluble Endoglin (ng/ml) | 3.7 ± 1.1 | <0.001* | 10.2 ± 9.8 | 0.01* | 96.1 ± 25.7 | 0.05 |
| Gestational age (weeks) | 29.9 ± 1.1 | 1.0 | 30.2 ± 1.0 | 1.0 | 30.4 ± 1.4 | 1.0 |
| Range | 28.3-32.0 | | 28.7-32.0 | | 29.4-31.4 | |
|  | n = 42 | | n = 33 | | n = $2^\delta$ | |
| $5^{th}$ blood sampling (32.1-36.9 weeks) | | | | | | |
| Soluble Endoglin (ng/ml) | 5.79 ± 2.42 | 0.003* | 10.51 ± 6.59 | <0.001* | 43.14 ± 25.6 | <0.001* |
| Gestational age (weeks) | 34.7 ± 1.3 | 1.0 | 34.8 ± 1.5 | 1.0 | 34.5 ± 1.2 | 1.0 |
| Range | 32.4-36.6 | | 32.6-36.7 | | 32.6-36.6 | |
|  | n = 37 | | n = 20 | | n = 13 | |
| $6^{th}$ blood sampling (>=37 weeks) | | | | | | |
| Soluble Endoglin (ng/ml) | 8.9 ± 4.5 | | — | | 15.23 ± 10.61 | 0.006* |
| Gestational age (weeks) | 39.4 ± 1.0 | | | | 38.8 ± 1.1 | 0.05 |
| Range | 37.0-40.7 | | | | 37.6-41.4 | |
|  | n = 27 | | | | n = 27 | |

$p^\beta$: compared between samples at clinical manifestation of pre-eclampsia and normal pregnancy
Value expressed as mean ± sd
$^\delta$2 pre-eclamptic patients had no blood samples available at clinical manifestation To examine the relationship between plasma soluble endoglin concentrations and the interval to clinical diagnosis of pre-eclampsia, plasma samples of pre-eclamptic patients at different gestational ages were stratified according to the interval from blood sampling to clinical diagnosis into five groups: (1) at clinical diagnosis, (2) 2-5.9 weeks before clinical manifestation, (3) 6-10.9 weeks before clinical manifestation, (4) 11-15.9 weeks before clinical manifestation, and (5) 16-25 weeks before clinical manifestation. The data shown in Table 4 demonstrates that the plasma soluble endoglin levels start going up at 6-10.9 weeks before onset of symptoms in pre-eclamptics and are at least 3 fold higher at 2-5.9 weeks before symptoms in women destined to develop pre-eclampsia.

TABLE 4

Plasma soluble endoglin concentrations in normal and pre-eclamptic pregnant women.

| Blood sampling | Normal pregnancy | Pre-eclampsia | p |
|---|---|---|---|
| At clinical manifestation | | | |
| Soluble Endoglin (ng/ml) | 7.63 ± 4.22 | 27.72 ± 26.20 | <0.001* |
| Gestational age (weeks) | 37.2 ± 3.0 | 37.1 ± 2.7 | 0.9 |
| Range | 28.9-40.7 | 29.4-41.4 | |
|  | n = 42 | n = $42^\delta$ | |
| 2-5.9 weeks before clinical manifestation | | | |
| Soluble Endoglin (ng/ml) | 4.67 ± 2.32 | 15.07 ± 10.15 | <0.001* |
| Gestational age (weeks) | 31.6 ± 3.8 | 32.8 ± 2.8 | 0.2 |
| Range | 24.1-36.3 | 27.1-36.7 | |
|  | n = 27 | n = 27 | |
| Interval before clinical manifestation (weeks) | | 3.8 ± 1.1 | |
| 6-10.9 weeks before clinical manifestation | | | |
| Soluble Endoglin (ng/ml) | 3.61 ± 1.05 | 5.89 ± 3.07 | <0.001* |
| Gestational age (weeks) | 28.5 ± 2.9 | 28.5 ± 2.9 | 0.9 |
| Range | 19.7-32.6 | 19.6-34.4 | |
|  | n = 37 | n = 37 | |
| Interval before clinical manifestation (weeks) | | 8.3 ± 1.4 | |
| 11-15.9 weeks before clinical manifestation | | | |
| Soluble Endoglin (ng/ml) | 3.35 ± 0.77 | 3.57 ± 0.92 | 0.5 |
| Gestational age (weeks) | 24.5 ± 3.1 | 24.2 ± 3.3 | 0.8 |
| Range | 17.6-27.9 | 17.7-28.0 | |
|  | n = 19 | n = 19 | |
| Interval before clinical manifestation (weeks) | | 13.2 ± 1.3 | |
| 16-25 weeks before clinical manifestation | | | |
| Soluble Endoglin (ng/ml) | 3.44 ± 1.07 | 3.69 ± 1.18 | 0.3 |
| Gestational age (weeks) | 17.6 ± 3.5 | 16.5 ± 4.5 | 0.2 |
| Range | 9.1-23.4 | 8.0-22.7 | |
|  | n = 42 | n = 42 | |

TABLE 4-continued

Plasma soluble endoglin concentrations in
normal and pre-eclamptic pregnant women.

| Blood sampling | Normal pregnancy | Pre-eclampsia | p |
|---|---|---|---|
| Interval before clinical manifestation (weeks) | | 20.6 ± 3.6 | |

Value expressed as mean ± sd
[δ] 2 pre-eclamptic patients had no blood samples available at clinical manifestation To examine the diagnostic potential of plasma soluble endoglin concentrations to identify those destined to develop pre-eclampsia, patients were stratified into early onset pre-eclampsia (PE<34 weeks) and late onset pre-eclampsia (PE>34 weeks). For patients with early-onset pre-eclampsia, the mean plasma soluble endoglin levels was significantly higher in pre-eclampsia (before clinical diagnosis) than in normal pregnancy starting around 16-24 weeks of gestation (Table 5) with very dramatic differences in 24-28 week and 28-32 week gestational windows. In contrast, for patients with late-onset pre-eclampsia, plasma soluble endoglin concentrations in pre-clinical pre-eclampsia was significantly higher than in normal pregnancy only at 28-32 weeks with very dramatic differences at 32-36 week of gestation (Table 6).

TABLE 5

Plasma soluble endoglin concentrations in normal pregnant women and patients who developed clinical Pre-eclampsia at 34 weeks of gestation or less.

| | Normal pregnancy | p | Pre-clinical samples Pre-eclampsia | p | Clinical samples pre-eclampsia[δ] | $p^\beta$ |
|---|---|---|---|---|---|---|
| 1st blood sampling (7.1-16 weeks) | | | | | | |
| Soluble Endoglin (ng/ml) | 3.89 ± .928 | 0.7 | 3.81 ± 1.11 | | | |
| Gestational age (weeks) | 12.3 ± 2.2 | 0.4 | 11.6 ± 2.6 | | | |
| Range | 8.4-15.9 | | 8.0-15.1 | | | |
| | n = 37 | | n = 8 | | | |
| 2nd blood sampling (16.1-24 weeks) | | | | | | |
| Soluble Endoglin (ng/ml) | 3.36 ± 1.11 | 0.02* | 4.60 ± 1.72 | | | |
| Gestational age (weeks) | 19.4 ± 1.7 | 0.7 | 19.8 ± 2.9 | | | |
| Range | 16.3-23.4 | | 17.3-23.9 | | | |
| | n = 44 | | n = 7 | | | |
| 3rd blood sampling (24.1-28 weeks) | | | | | | |
| Soluble Endoglin (ng/ml) | 3.189 ± .729 | <0.001* | 10.22 ± 6.17 | | | |
| Gestational age (weeks) | 25.9 ± 1.3 | 0.03* | 26.8 ± 0.6 | | | |
| Range | 24.1-28.0 | | 26.0-27.3 | | | |
| | n = 38 | | n = 6 | | | |
| 4th blood sampling (28.1-32 weeks) | | | | | | |
| Soluble Endoglin (ng/ml) | 3.70 ± 1.10 | 0.01* | 17.66 ± 8.9 | 0.008* | 96.10 ± 25.76 | 0.05 |
| Gestational age (weeks) | 29.9 ± 1.1 | 1.0 | 29.7 ± 1.1 | 1.0 | 30.4 ± 1.4 | 1.0 |
| Range | 28.3-32.0 | | 28.7-31.3 | | 29.4-31.4 | |
| | n = 42 | | n = 6 | | n = 2[δ] | |
| 5th blood sampling (32.1-36.9 weeks) | | | | | | |
| Soluble Endoglin (ng/ml) | 5.79 ± 2.42 | | | | 53.38 ± 32.09 | 0.001* |
| Gestational age (weeks) | 34.7 ± 1.3 | | | | 33.5 ± 0.5 | <0.001* |
| Range | 32.4-36.6 | | | | 32.6-34.0 | |
| | n = 37 | | | | n = 6 | |

$p^\beta$: compared between samples at clinical manifestation of pre-eclampsia and normal pregnancy
Value expressed as mean ± sd
[δ]2 pre-eclamptic patients had no blood samples available at clinical manifestation

TABLE 6

Plasma soluble endoglin concentrations in normal pregnant women and pre-eclamsptics (34 weeks of gestation)

| | Normal pregnancy | p | Pre-clinical samples Pre-eclampsia | p | Clinical samples Pre-eclampsia | $p^\beta$ |
|---|---|---|---|---|---|---|
| 1st blood sampling (7.1-16 weeks) | | | | | | |
| Soluble Endoglin (ng/ml) | 3.89 ± .928 | 0.9 | 4.01 ± 1.35 | | | |
| Gestational age (weeks) | 12.3 ± 2.2 | 0.2 | 11.6 ± 2.4 | | | |
| Range | 8.4-15.9 | | 7.7-15.1 | | | |
| | n = 37 | | n = 26 | | | |
| 2nd blood sampling (16.1-24 weeks) | | | | | | |
| Soluble Endoglin (ng/ml) | 3.36 ± 1.11 | 0.4 | 3.59 ± 1.23 | | | |
| Gestational age (weeks) | 19.4 ± 1.7 | 0.04* | 20.3 ± 1.9 | | | |

TABLE 6-continued

Plasma soluble endoglin concentrations in normal pregnant women and pre-eclamsptics (34 weeks of gestation)

|  | Normal pregnancy | p | Pre-clinical samples Pre-eclampsia | p | Clinical samples Pre-eclampsia | p$^\beta$ |
|---|---|---|---|---|---|---|
| Range | 16.3-23.4 n = 44 |  | 16.7-24.0 n = 29 |  |  |  |
| 3$^{rd}$ blood sampling (24.1-28 weeks) |  |  |  |  |  |  |
| Soluble Endoglin (ng/ml) | 3.18 ± .729 | 0.1 | 3.98 ± 2.13 |  |  |  |
| Gestational age (weeks) | 25.9 ± 1.3 | 0.4 | 26.3 ± 1.1 |  |  |  |
| Range | 24.1-28.0 n = 38 |  | 24.6-28.0 n = 23 |  |  |  |
| 4$^{th}$ blood sampling (28.1-32 weeks) |  |  |  |  |  |  |
| Soluble Endoglin (ng/ml) | 3.70 ± 1.10 | 0.001* | 8.57 ± 9.45 |  |  |  |
| Gestational age (weeks) | 29.9 ± 1.1 | 0.2 | 30.3 ± 1.0 |  |  |  |
| Range | 28.3-32.0 n = 42 |  | 28.7-32.0 n = 27 |  |  |  |
| 5$^{th}$ blood sampling (32.1-36.9 weeks) |  |  |  |  |  |  |
| Soluble Endoglin (ng/ml) | 5.79 ± 2.42 | <0.001* | 10.51 ± 6.59 | <0.001* | 34.36 ± 16.30 | <0.001* |
| Gestational age (weeks) | 34.7 ± 1.3 | 1.0 | 34.8 ± 1.5 | 0.9 | 35.4 ± 0.9 | 0.7 |
| Range | 32.4-36.6 n = 37 |  | 32.6-36.7 n = 20 |  | 34.3-36.6 n = 7 |  |
| 6$^{th}$ blood sampling (>=37 weeks) |  |  |  |  |  |  |
| Soluble Endoglin (ng/ml) | 8.98 ± 45.12 |  | — |  | 15.23 ± 10.61 | 0.006* |
| Gestational age (weeks) | 39.4 ± 1.0 |  |  |  | 38.8 ± 1.1 | 0.05 |
| Range | 37.0-40.7 n = 27 |  |  |  | 37.6-41.4 n = 27 |  | p$^\beta$: compared between samples at clinical manifestation of pre-eclampsia and normal pregnancy
Value expressed as mean ± sd Summary The results of these experiments demonstrate that women with clinical pre-eclampsia have very high levels of circulating soluble endoglin when compared to gestational age matched controls. The results also demonstrate that women destined to develop pre-eclampsia (pre-clinical pre-eclampsia) have higher plasma soluble endoglin levels than those who are predicted to have a normal pregnancy. The increase in soluble endoglin levels is detectable at least 6-10 weeks prior to onset of clinical symptoms. Finally, these results demonstrate that both early onset and late onset pre-eclampsia have elevated circulating soluble endoglin concentrations, but the alterations are more dramatic in the early onset pre-eclampsia.

Example 6

Soluble Endoglin Protein Levels as a Diagnostic Indicator of Pre-eclampsia and Eclampsia in Women (CPEP Study)

As described above, we have discovered that soluble endoglin, a cell surface receptor for the pro-angiogenic protein TGF-β and expressed on endothelium and syncytiotrophoblast, is upregulated in pre-eclamptic placentas. In the experiments described above, we have shown that in pre-eclampsia excess soluble endoglin is released from the placenta into the circulation through shedding of the extracellular domain; soluble endoglin may then synergize with sFlt1, an anti-angiogenic factor which binds placental growth factor (PlGF) and VEGF, to cause endothelial dysfunction. To test this hypothesis, we compared serum concentrations of soluble endoglin, sFlt1, and free PlGF throughout pregnancy in women who developed pre-eclampsia and in those women with other pregnancy complication such as gestational hypertension (GH) and pregnancies complicated by Small-for-gestational (SGA) infants to those of women with normotensive control pregnancies. This study was done in collaboration with the Dr. Richard Levine at the NIH.

There were two principal objectives of this study. The first objective was to determine whether, in comparison with normotensive controls, elevated serum concentrations of soluble endoglin, sFlt1, and reduced levels of PlGF can be detected before the onset of pre-eclampsia and other gestational disorders such as gestational hypertension or pregnancies complicated by small-for-gestational (SGA) infants. The second objective was to describe the time course of maternal serum concentrations of soluble endoglin, sFlt-1, and free PlGF with respect to gestational age in women with pre-eclampsia, gestational hypertension, or SGA with separate examination of specimens obtained before and after onset of clinical symptoms, and in normotensive controls.

Methods

Clinical Information

This study was a case control study of pregnancy complications (premature pre-eclampsia, term pre-eclampsia, gestational hypertension, pregnancies with SGA infants, normotensive control pregnancies) nested within the cohort of 4,589 healthy nulliparous women who participated in the Calcium for Pre-eclampsia Prevention trial (CPEP). 120 random cases were selected from each of the study groups. The study methods were identical to the nested case control study recently performed for pre-eclampsia (Levine et al, N. Eng. J. Med. 2004, 350:672-83). From each woman blood specimens were obtained before study enrollment (13-21 wks), at 26-29 wks, at 36 wks, and on suspicion of hypertension or proteinuria. All serum specimens collected at any time during pregnancy before onset of labor and delivery were eligible for the study. Cases included 120 women who developed term pre-eclampsia, gestational hypertension, or SGA and who delivered a liveborn or stillborn male baby without known major structural or chromosomal abnormalities, and from whom a baseline serum specimen was obtained. For premature pre-eclampsia, defined as (PE<37 weeks) all 72 patients from the CPEP cohort were studied. The clinical criterion for the diagnosis of pre-eclampsia is described in Levine et al., (2004), supra. All cases of gestational hypertension were required to have a normal urine protein measurement within the interval from 1 day prior to onset of gestational hypertension through 7 days following. SGA was defined as <10th and <5th (severe SGA) percentile, using Zhang & Bowes' tables of birthweight for gestational age, specific for race, nulliparity, and infant gender. Controls were randomly selected from women without pre-eclampsia or gestational hypertension or SGA who delivered a liveborn or stillborn baby without known major structural malformations or chromosomal anomalies and matched, one control to one case, by the clinical center, gestational age at collection of the first serum specimen (±1 wk), by freezer storage time (±1 year), and by number of freeze-thaws. A total of 1674 serum specimens were studied. Matching by gestational age was done to control for gestational age-related differences in levels of sFlt-1, VEGF, and PlGF. Matching for freezer storage time was done to minimize differences due to possible degradation during freezer storage. Matching by clinical center was done to control for the fact that pre-eclampsia rates differed significantly between centers, perhaps due to differences in the pathophysiology of the disease. In addition, the centers may have used slightly different procedures for collecting, preparing, and storing specimens. Matching by number of thaws was also performed to ensure that cases and controls will have been subjected equally to freeze thaw degradation.

ELISA Measurements

ELISA for the various angiogenic markers were performed at the Karumanchi laboratory by a single research assistant that was blinded to the clinical outcomes.

Commercially available ELISA kits for soluble endoglin (DNDG00), sFlt1 (DVR100), PlGF (DPG00) were obtained from R&D systems, (Minneapolis, Minn.).

Statistical Analysis

T-test was used for the comparison of the various measurements after logarithmic transformation to determine significance. P<0.05 was considered as statistically significant.

Results

Figure 6:
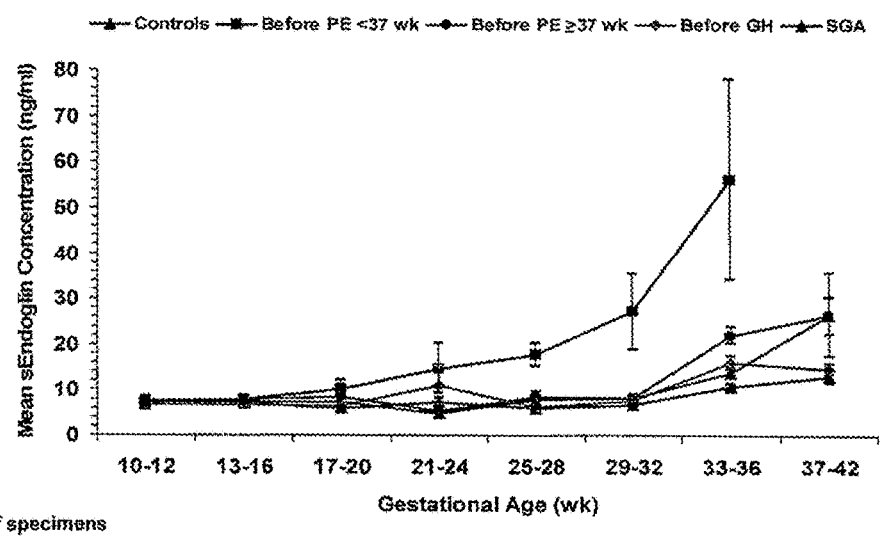
FIG. 6 is a graph showing the mean soluble endoglin concentration for the five different study groups of pregnant women throughout pregnancy during the various gestational age group windows.
Figure 7:
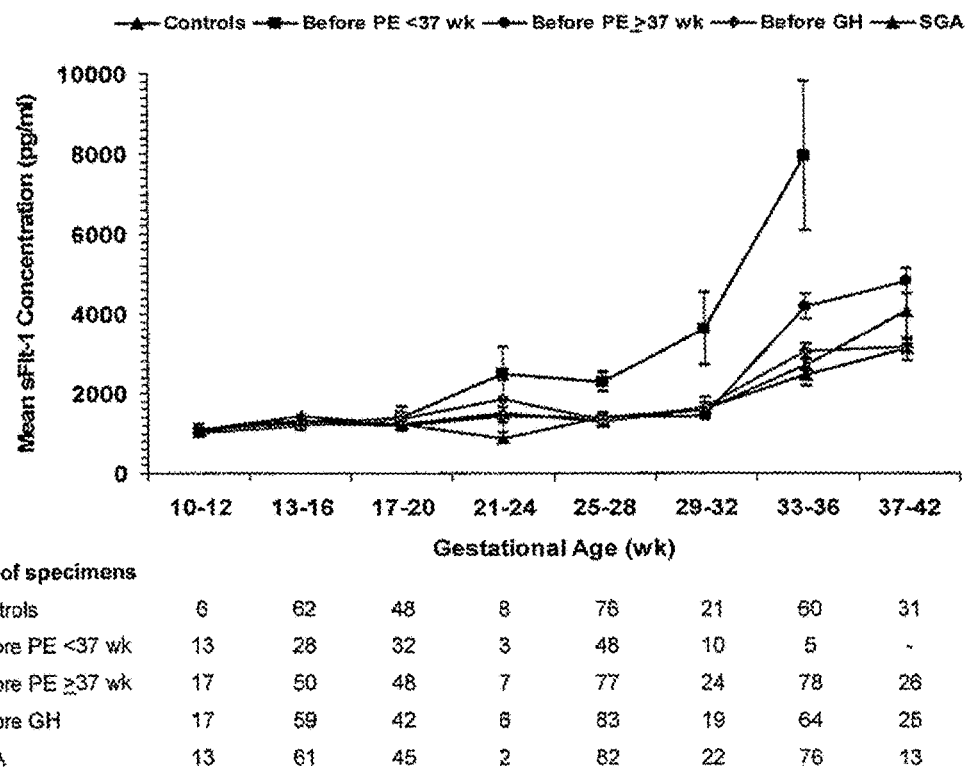
FIG. 7 is a graph showing the mean sFlt1 concentrations for the five different study groups of pregnant women throughout pregnancy during the various gestational age group windows.
Figure 8:
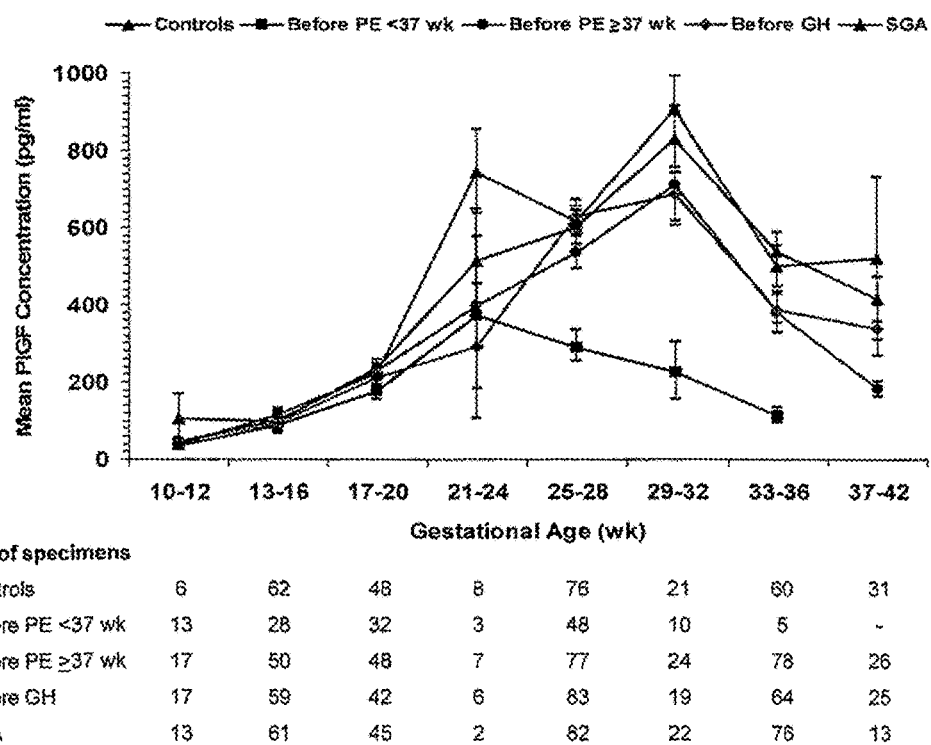
FIG. 8 is a graph showing the mean PlGF concentrations for the five different study groups of pregnant women throughout pregnancy during the various gestational age group windows.

The mean soluble endoglin (FIG. 6), sFlt1 (FIG. 7) and PlGF (FIG. 8) concentrations for the five different study groups of pregnant women throughout pregnancy during the various gestational age group windows as described in the methods are shown in FIGS. 6-8. For the pre-eclampsia groups and gestational hypertensive groups, specimens taken after onset of clinical symptoms are not shown here. Compared with gestational age-matched control specimens, soluble endoglin and sFlt1 increased and free PlGF decreased beginning 9-11 wks before preterm pre-eclampsia, reaching levels 5-fold (46.4 vs 9.8 ng/ml, P<0.0001) and 3-fold higher (6356 vs 2316 pg/ml, P<0.0001) and 4-fold lower (144 vs 546 pg/ml, P<0.0001), respectively, after pre-eclampsia onset. For term pre-eclampsia, soluble endoglin increased beginning 12-14 wks, free PlGF decreased beginning 9-11 wks, and sFlt1 increased <5 wks before pre-eclampsia onset. Serum concentrations of sFlt1 and free PlGF did not differ significantly between pregnancies with SGA or average for gestation age/large for gestation age (AGA/LGA) infants from 10-42 wks of gestation. Serum soluble endoglin was modestly increased in SGA pregnancies beginning at 17-20 wks (7.2 vs 5.8 ng/ml, P=0.03), attaining concentrations of 15.7 and 43.7 ng/ml at 37-42 wks for mild and severe SGA, respectively, as compared with 12.9 ng/ml in AGA/LGA pregnancies (severe SGA vs AGA/LGA, P=0.002). In gestation hypertensive study, compared with GA-matched control specimens, modest increases in soluble endoglin were apparent <1-5 wks before gestational hypertension, reaching levels 2-fold higher for soluble endoglin (29.7 vs 12.5 ng/ml, P=0.002) after onset of gestational hypertension. The adjusted odds ratio for subsequent preterm PE for specimens obtained at 21-32 wks which were in the highest quartile of control soluble endoglin concentrations (>7.2 ng/ml), as compared to all other quartiles, was 9.8 (95% CI 4.5-21.5).

Figure 9:
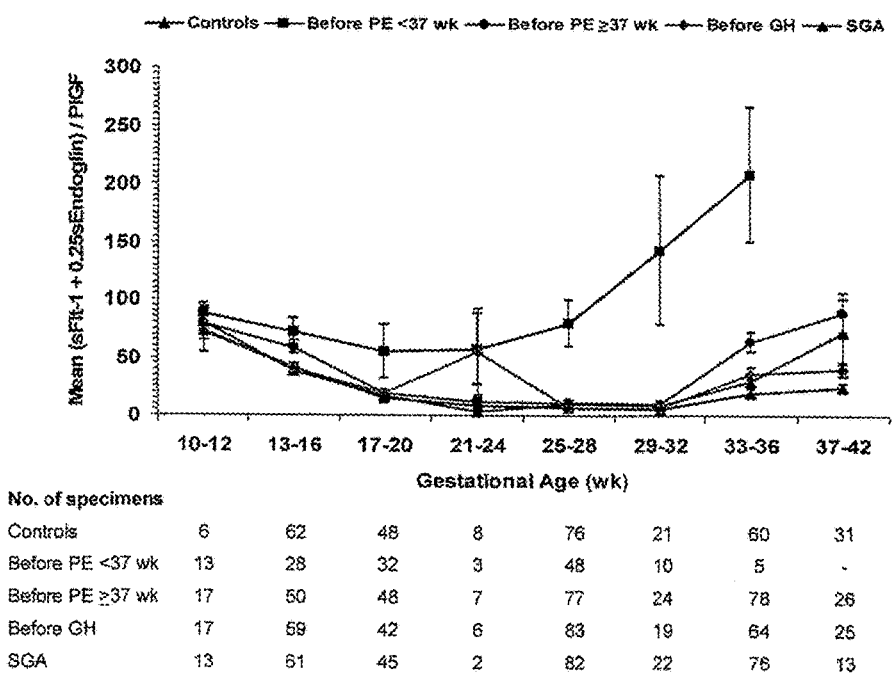
FIG. 9 is a graph showing the values for the soluble endoglin anti-angiogenic index for pre-eclampsia anti-angiogenesis for samples taken prior to clinical symptoms.

The soluble endoglin anti-angiogenic index for pre-eclampsia was defined as (sFlt1+0.25 soluble endoglin)/PlGF. The index was calculated throughout the various gestational age groups for the five different study groups. The soluble endoglin anti-angiogenic index for pre-eclampsia anti-angiogenesis for samples taken prior to clinical symptoms is shown in FIG. 9. Elevated values for the soluble endoglin anti-angiogenic index were noted as early as 17-20 weeks of pregnancies and seemed to get more dramatic with advancing gestation in severe premature pre-eclampsia. In term pre-eclampsia, SGA and GH, there was a modest elevation during the end of pregnancy (33-36 weeks) when compared to control women.

Figure 10:
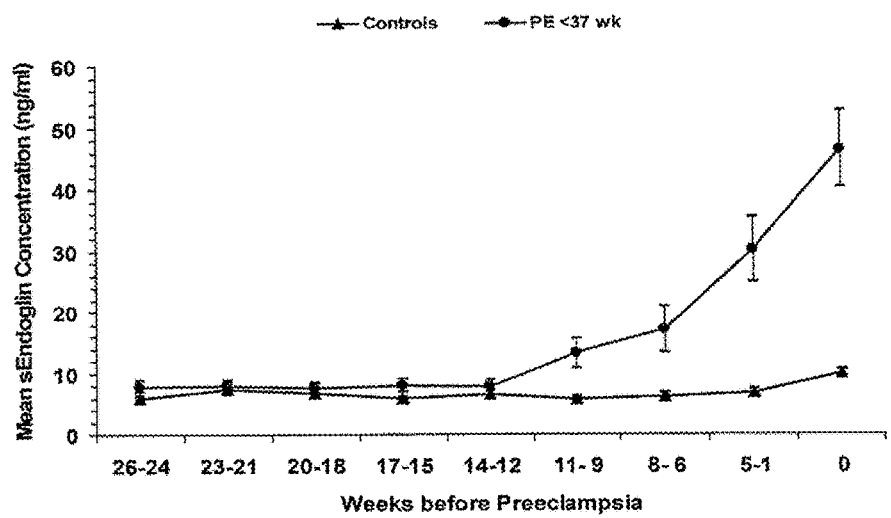
FIG. 10 is a graph showing the mean concentrations of soluble endoglin according to the number of weeks before clinical premature pre-eclampsia (PE<37 weeks).
Figure 11:
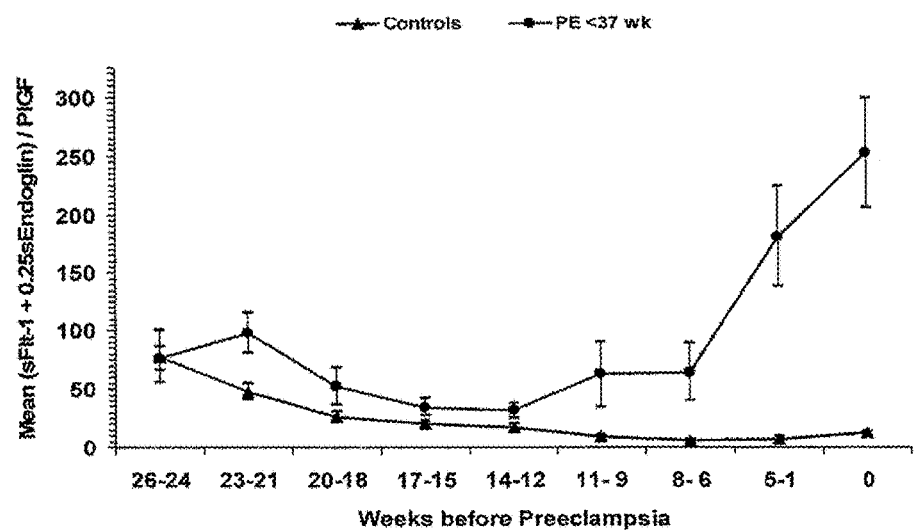
FIG. 11 is a graph showing the soluble endoglin anti-angiogenic index values according to the number of weeks before clinical premature pre-eclampsia (PE<37 weeks).

FIGS. 10 and 11 depict the mean concentrations of soluble endoglin (FIG. 10) and soluble endoglin anti-angiogenic index (FIG. 11) according to the number of weeks before clinical premature pre-eclampsia (PE<37 weeks). Even as early 9-11 weeks prior to the onset of premature pre-eclampsia, there was a 2-3 fold elevation in soluble endoglin and soluble endoglin anti-angiogenic index in women destined to develop pre-eclampsia with dramatic elevations (>5 fold) in 1-5 weeks preceding clinical symptoms.

Figure 12:
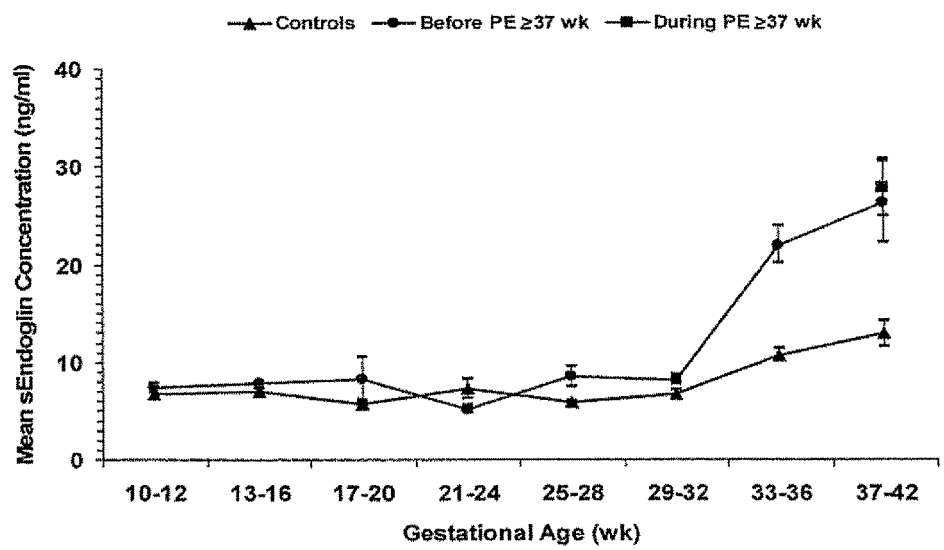
FIG. 12 is a graph showing the alteration in soluble endoglin levels throughout pregnancy for term pre-eclampsia (PE>37 weeks) before and after symptoms.
Figure 13:
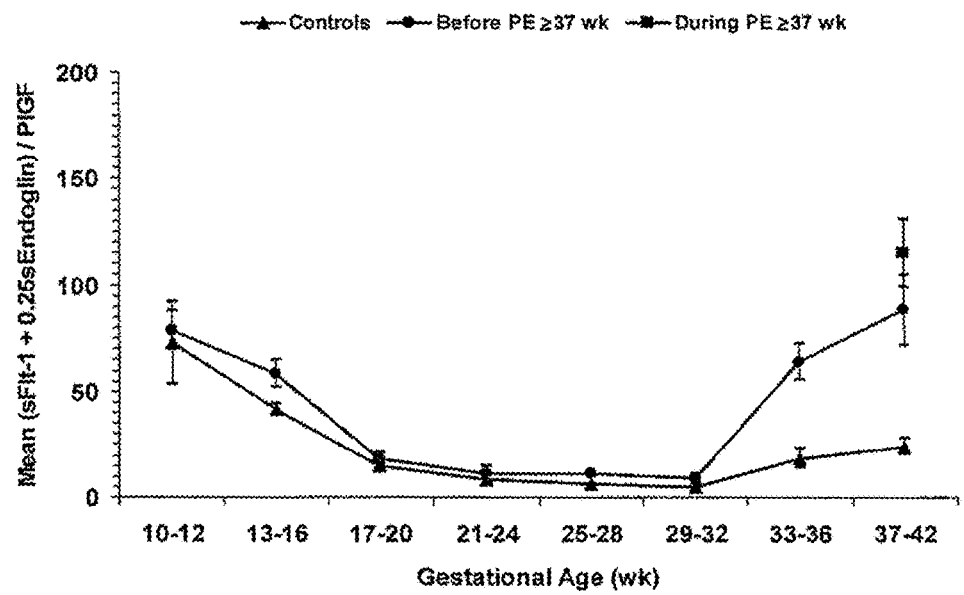
FIG. 13 is a graph showing the alteration in the soluble endoglin anti-angiogenic index levels throughout pregnancy for term pre-eclampsia (PE>37 weeks) before and after symptoms.

FIGS. 12 and 13 show the alteration in soluble endoglin (FIG. 12) and the soluble endoglin anti-angiogenic index (FIG. 13) throughout pregnancy for term pre-eclampsia (PE>37 weeks) before and after symptoms. Elevation in soluble endoglin and the soluble endoglin anti-angiogenic index are noted starting at 33-36 weeks of pregnancy reaching on average 2-fold higher levels at the time of clinical pre-eclampsia.

Figure 14:
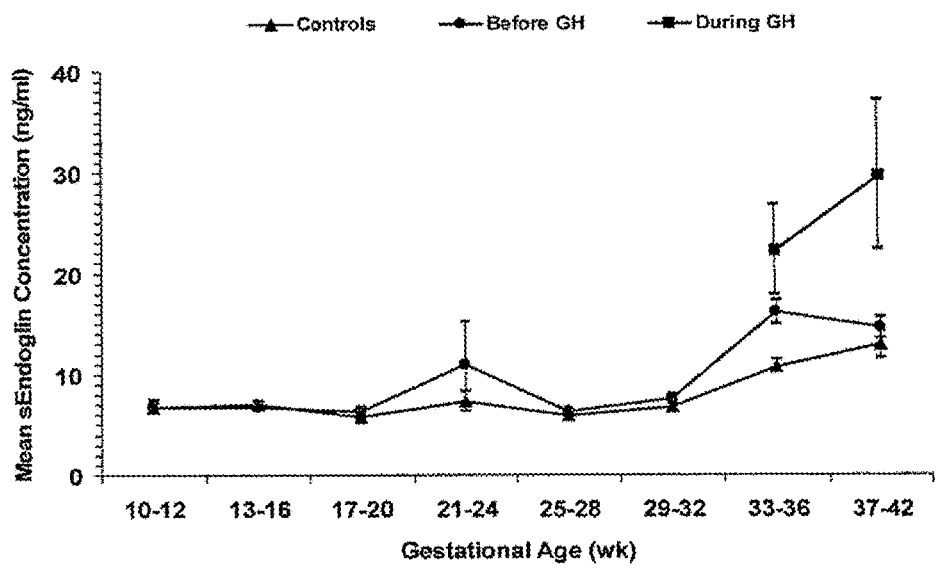
FIG. 14 is a graph showing the soluble endoglin levels detected in women during gestational hypertension and before gestational hypertension (1-5 weeks preceding gestational hypertension (during 33-36 week of pregnancy)) and normotensive controls.
Figure 15:
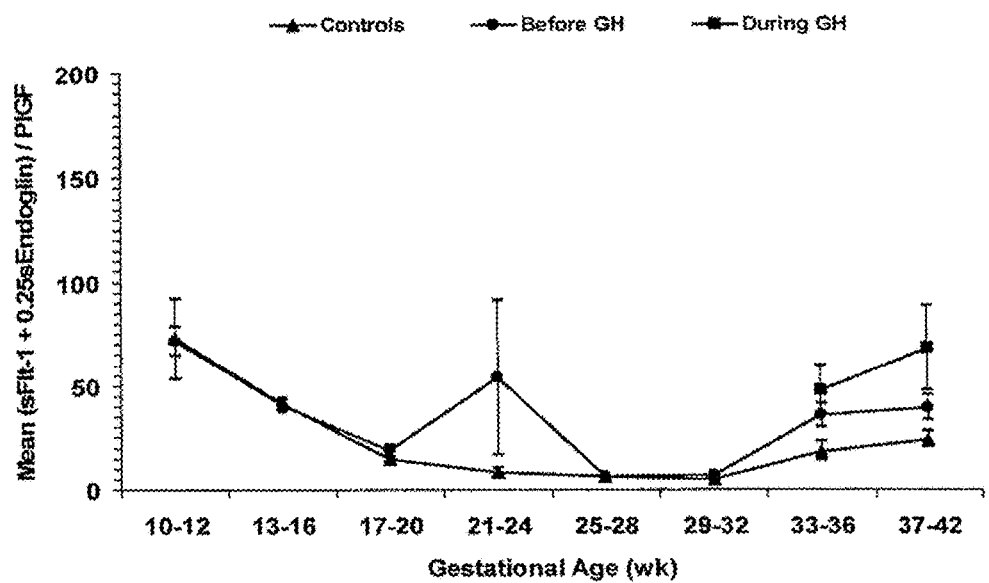
FIG. 15 is a graph showing the soluble endoglin anti-angiogenic index levels in women during gestational hypertension and before gestational hypertension (1-5 weeks preceding gestational hypertension (during 33-36 week of pregnancy)) and normotensive controls.

FIGS. 14 and 15 show a modest elevation in soluble endoglin (FIG. 14) and the soluble endoglin anti-angiogenic index (FIG. 15) detected in women during gestational hypertension, and 1-5 weeks preceding gestational hypertension (during 33-36 week of pregnancy) when compared to normotensive controls.

Figure 16:
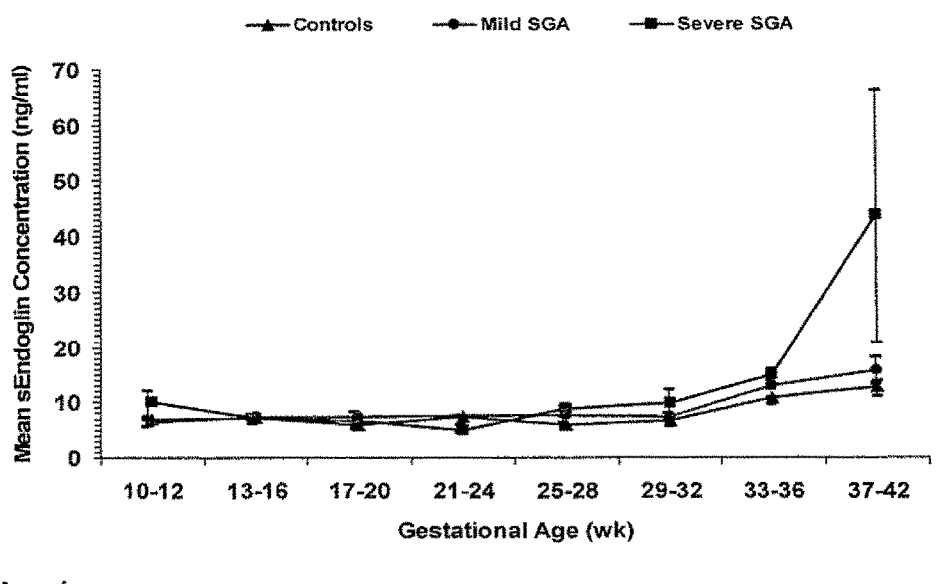
FIG. 16 is a graph showing the soluble endoglin levels detected during the 33-36 week gestational windows in women with severe SGA, mild SGA, and normotensive controls.
Figure 17:
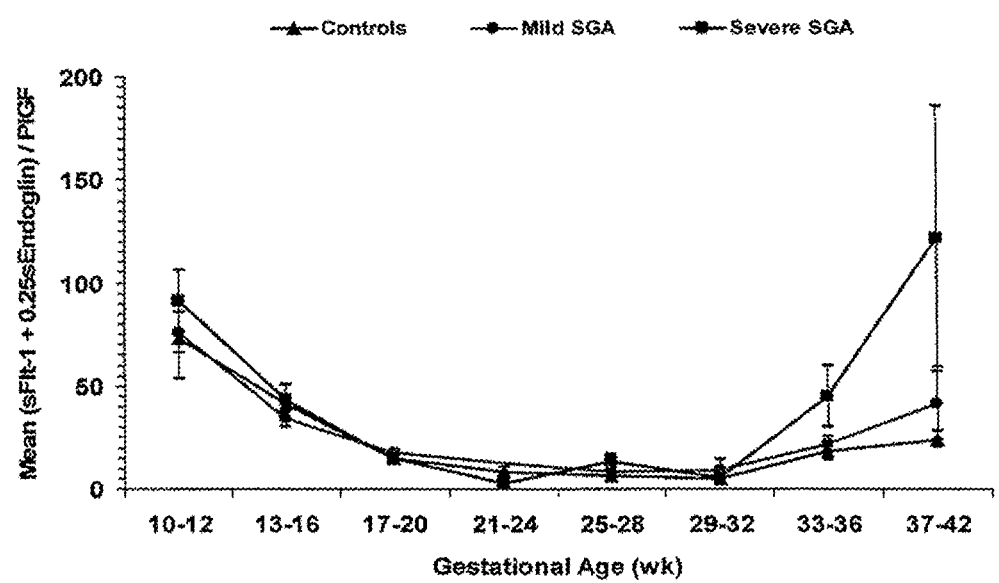
FIG. 17 is a graph showing the soluble endoglin anti-angiogenic index levels detected during the 33-36 week gestational windows in women with severe SGA, mild SGA, and normotensive controls.

FIGS. 16 and 17 show a modest elevations in soluble endoglin (FIG. 16) and the soluble endoglin anti-angiogenic index (FIG. 17) detected during the 33-36 week gestational windows in women with severe SGA and not in all women with SGA when compared to control pregnancies.

Summary

The results of this study show that the soluble endoglin levels and soluble endoglin anti-angiogenic index levels, when measured prior to 33 weeks of pregnancy, was dramatically elevated in women destined to develop premature pre-eclampsia and in women with clinical premature pre-eclampsia (PE<37 weeks) when compared to normal control pregnancy. Therefore, soluble endoglin levels and soluble endoglin anti-angiogenic index levels (prior to 33 weeks)

can not only be used for the diagnosis of premature pre-eclampsia, but also for the prediction of pre-eclampsia. It appears that elevations in soluble endoglin levels and soluble endoglin anti-angiogenic index levels start as early as 10-12 weeks prior to symptoms of pre-eclampsia.

The soluble endoglin levels and soluble endoglin anti-angiogenic index levels were also significantly elevated in term pre-eclampsia (PE>37 weeks) and modestly elevated in gestational hypertension and severe SGA when measured late in pregnancy (33-36 week gestational windows). Therefore, soluble endoglin levels and soluble endoglin anti-angiogenic index levels can also be used to identify other pregnancy complications such as SGA and gestation hypertension when measured after 33 weeks of pregnancy.

Example 7

Involvement of Soluble Endoglin in the Pathogenesis of Pre-eclampsia

We have shown that endoglin, a cell surface receptor for the pro-angiogenic protein TGF-β and expressed on endothelium and syncytiotrophoblast, is upregulated in pre-eclamptic placentas. We have also shown that in pre-eclampsia, excess soluble endoglin is released from the placenta into the circulation through shedding of the extracellular domain. The experiments described below were designed to test the hypothesis that soluble endoling may synergize with sFlt1, an anti-angiogenic factor which binds placental growth factor (PlGF) and VEGF, to cause endothelial dysfunction.

Materials and Methods

Reagents

Recombinant Human endoglin, human sFlt1, mouse endoglin, mouse sFlt1, human TGF-β1, human TGF-β3, mouse VEGF were obtained from R&D systems (Minneapolis, Minn.). Mouse monoclonal antibody (catalog # sc 20072) and polyclonal antibody (sc 20632) against the N-terminal region of human endoglin was obtained from Santa Cruz Biotechnology, Inc. ELISA kits for human sFlt1, mouse sFlt1 and human soluble endoglin were obtained from R&D systems, MN.

Generation of Adenoviruses

Adenoviruses against sFlt1 and control adenovirus (CMV) have been previously described (Maynard et al, *J. Clin. Invest.* 111: 649:658 (2003)) and were generated at the Harvard Medical Core facility in collaboration with Dr. Richard Mulligan. To create the soluble endoglin adenovirus, we used the Adeasy Kit (Stratagene). Briefly, human soluble endoglin (Thr 27-Leu 586) was PCR amplified using human cDNA full length endoglin clone (Invitrogen, CA) as the template and the following oligonucleotides as primers: forward 5'-ACG AAG CTT GAA ACA GTC CAT TGT GAC CTT-3' (SEQ ID NO: 3) and reverse 5'TTA GAT ATC TGG CCT TTG CTT GTG CAA CC-3' (SEQ ID NO: 4). Amplified PCR fragments were initially subcloned into pSecTag2-B (Invitrogen, CA) and the DNA sequence was confirmed. A mammalian expression construct encoding His-tagged human soluble endoglin was PCR amplified using pSecTag2 B-soluble endoglin as the template and subcloned into pShuttle-CMV vector (Stratagene; Kpn1 and Sca1 sites), an adenovirus transfer vector, for adenovirus generation. Adenovirus expressing soluble endoglin (sE) was then generated using the standard protocol per manufacturer instructions and confirmed for expression by western blotting. The confirmed clone was then amplified on 293 cells and purified on a CsCl2 density gradient as previously described (Kuo et al, *Proc. Natl. Acad. Sci. USA* 98:4605-4610 (2001)). The final products were titered by an optical absorbance method (Sweeney et al, *Virology*, 2002, 295: 284-288). The titer is expressed as plaque forming units (pfu)/mL based on a formula derived from previous virus preps that were titered using the standard plaque dilution based titration assay kit (BD Biosciences Clontech, Palo Alto, Calif., Cat. No. K1653-1) and the optical absorbance method.

Patients

All the patients for this study were recruited at the Beth Israel Deaconess Medical Center after obtaining appropriate IRB-approved consents. Pre-eclampsia was defined as (1) Systolic BP>140 and diastolic BP>90 after 20 weeks gestation in a previously normotensive patient, (2) new onset proteinuria (1+ by dipstick on urinalysis or >300 mg of protein in a 24 hr urine collection or random urine protein/creatinine ratio >0.3), and (3) resolution of hypertension and proteinuria by 12 weeks postpartum. Patients with baseline hypertension, proteinuria, or renal disease were excluded. For the purposes of this study, patients were divided into mild and severe pre-eclampsia based on the absence or presence of nephrotic-range proteinuria (>3 g of protein on a 24 hour urine collection or urine protein to creatinine ratio greater than 3.0). HELLP syndrome was defined when patients had evidence of thrombocytopenia (<100000 cells/μl), increased LDH (>600 IU/L) and increased AST (>70 IU/L). Healthy pregnant women were included as controls. 8 patients with pre-term deliveries for other medical reasons were included as additional controls. Placental samples were obtained immediately after delivery. Serum was collected from pregnant patients at the time of delivery (0-12 hours prior to delivery of the placenta) after obtaining informed consent. These experiments were approved by the Institutional Review Board at the Beth Israel Deaconess Medical Center.

ELISA and Western Blots

ELISA for various proteins (sFlt1, soluble endoglin) was done as per manufacturer's instructions using commercial kits from R&D systems, MN. Western blots and ELISA were used for checking the expression of adenoviral-infected transgenes in the rat plasma as described elsewhere (Maynard et al, supra).

Immunoprecipitation (IP) Experiments

IP followed by western blots were used to identify and characterize soluble endoglin in the placental tissue and serum specimens from patients with pre-eclampsia. Human placental tissue was washed with cold PBS and lysed in homogenization buffer [10 mM Tris-HCl, pH 7.4; 15 mM NaCl; 60 mM KCl; 1 mM EDTA; 0.1 mM EGTA; 0.5% Nonidet P-40; 5% sucrose; protease mixture from Roche (Indianapolis, Ind.)] for 10 minutes. Placental lysates were then subjected to immunoprecipitation with an anti-human monoclonal mouse endoglin antibody (Santa Cruz Biotechnology, Inc., Santa Cruz, Calif.). Immunoaffinity columns were prepared by the directional coupling of 3-5 mg of the purified antibody to 2 ml protein A-Sepharose using an immunopure IgG orientation kit (Pierce Chemical Co., Rockford, Ill., USA) according to the manufacturer's instructions. Columns were then washed extensively with RIPA buffer containing protease mixture, and bound proteins were eluted with 0.1 mol/L glycine-HCl buffer, pH 2.8. The eluent was collected in 0.5-ml fractions containing 1 mol/L Tris-HCl buffer. Protein-containing fractions were pooled and concentrated 9- to 10-fold with CENTRICON Centrifugal Concentrator (Millipore Corp., Bedford, Mass., USA). The immunoprecipitated samples were separated on a 4-12% gradient gel (Invitrogen) and proteins were transferred to polyvinylidene difluoride (PVDF) membranes. Endoglin protein was detected by western blots using polyclonal anti-human rabbit endoglin primary antibody (Santa Cruz Biotechnology, Inc., Santa Cruz, Calif.).

Endothelial Tube Assay

Growth factor reduced matrigel (7 mg/mL, Collaborative Biomedical Products, Bedford, Mass.) was placed in wells (100l/well) of a pre-chilled 48-well cell culture plate and incubated at 37° C. for 30 minutes to allow polymerization. HUVEC cells (30,000+ in 300 μl of endothelial basal medium with no serum, Clonetics, Walkersville, Md.) were treated with various combinations of recombinant protein (soluble endoglin, sFlt1, or both) and plated onto the Matrigel coated wells, and incubated at 37° C. for 12-16 hours. Tube formation was then assessed through an inverted phase contrast microscope at 4x (Nikon Corporation, Tokyo, Japan) and quantitatively analyzed (tube area and total length) using the Simple PCI imaging analysis software.

Microvascular Permeability Experiments

Balb-C mice were injected through the retro-orbital venous plexus with $1 \times 10^8$ pfu of adenovirus expressing GFP or soluble endoglin or sFlt1 or combinations and microvascular permeability assay was performed 48 hours later. Mice were anesthetized by IP injection of 0.5 ml Avertin. 100 ml of 1% Evans blue dye (in PBS) was injected into the tail vein. 40 minutes later, mice were perfused via heart puncture with PBS containing 2 mM EDTA for 20 minutes. Organs (brain, lung, liver, kidney) were harvested and incubated in formamide for 3 days to elute Evans blue dye. OD of formamide solution was measured using 620 nm wave length.

Renal Microvascular Reactivity Experiments

Microvascular reactivity experiments were done as described previously (Maynard et al., supra) using rat renal microvessels (70-170 μm internal diameter). In all experimental groups, the relaxation responses of kidney microvessels were examined after pre-contraction of the microvessels with U46619 (thromboxane agonist) to 40-60% of their baseline diameter at a distending pressure of 40 mmHg. Once the steady-state tone was reached, the responses to various reagents such as TGF-β1 or TGF-β3 or VEGF were examined in a standardized order. All drugs were applied extraluminally.

Animal Models

Both pregnant and non-pregnant Sprague-Dawley rats were injected with $2 \times 10^9$ pfu of adenoviruses (Ad CMV or Ad sFlt1 or Ad sE or Ad sFlt1+Ad sE) by tail vein injections. Pregnant rats were injected at day 8-9 of pregnancy (early second trimester) and blood pressure measured at day 16-17 of pregnancy (early third trimester). Blood pressures were measured in the rats after anesthesia with pentobarbital sodium (60 mg/kg, i.p.). The carotid artery was isolated and cannulated with a 3-Fr high-fidelity microtip catheter connected to a pressure transducer (Millar Instruments, Houston, Tex.). Blood pressure was recorded and averaged over a 10-minute period. Blood, tissue and urine samples were then obtained before euthanasia. Plasma levels were measured on the day of blood pressure measurement (day 8 after injection of the adenoviruses), recognizing that 7-10 days after adenoviral injection corresponds to the peak level of expression of these proteins. Circulating sFlt-1 and soluble endoglin levels were confirmed initially by western blotting and then quantified using commercially available murine ELISA kits (R & D Systems, Minneapolis, Minn.). Urinary albumin was measured both by both standard dipstick and quantified by competitive enzyme-linked immunoassay using a commercially available rat albumin ELISA kit (Nephrat kit, Exocell Inc, Philadelphia, Pa.). Urinary creatinine was measured by a picric acid colorimetric procedure kit (Metra creatinine assay kit, Quidel Corp, San Diego, Calif.). AST and LDH were measured using the commercially available kits (Thermo Electron, Louisville, Colo.). Platelet counts from rat blood were measured using an automated hemocytometer (Hemavet 850, Drew Scientific Inc, Oxford, Conn.). A peripheral smear of the blood with Wright's stain was performed for the detection of schistocytes in circulating blood. After the measurement of blood pressure and collection of specimens, the rats were sacrificed and organs harvested for histology. The litter was counted and individual placentas and fetuses weighed. Harvested kidneys were placed in Bouin's solution, paraffin embedded, sectioned and stained with H&E, PAS or Masson's trichrome stain.

Statistical Comparisons

Results are presented as mean±standard error of mean (SEM) and comparisons between multiple groups were made by analysis of variance using ANOVA. Significant differences are reported when $p<0.05$.

Results

Elevated Soluble Endoglin in Patients with Pre-eclampsia

Using the serum specimens from patients described in Table 7, we measured the circulating concentrations of soluble endoglin in the various groups of pre-eclamptic patients and control pregnant patients.

TABLE 7

Clinical characteristics and circulating soluble endoglin in the various patient groups

|  | Normal (n = 30) | Mild pre-eclampsia (n = 11) | Severe pre-eclampsia, no HELLP (n = 17) | Severe pre-eclampsia with HELLP (n = 11) | Pre-term (n = 8) |
|---|---|---|---|---|---|
| Maternal age (yrs) | 32.43 | 33.18 | 29.5 | 33.73 | 31.88 |
| Gestational age (wks) | 38.65 | 31.91* | 29.06* | 26.52* | 30.99* |
| Primiparous (%) | 43.3 | 63.6 | 47.1 | 90.9 | 62.5 |
| Systolic blood pressure (mmHg) | 122 | 157* | 170* | 166* | 123 |
| Diastolic blood pressure (mmHg) | 72 | 99* | 104* | 103* | 77 |
| Proteinuria (g protein/g creatinine) | 0.37 | 2.5* | 8.64* | 5.16* | 0.6 |
| Uric acid (mg/dl) | 5.27 | 6.24 | 7.29* | 6.31 | 7.35 |
| Hematocrit (%) | 35.5 | 33.6 | 33.7 | 33.5 | 34.3 |
| Platelet count | 238 | 230 | 249 | 69.4* | 229 |
| Creatinine (mg/dl) | 0.55 | 0.62 | 0.62 | 0.64 | 0.67 |
| Soluble endoglin in (ng/ml) | 18.73 | 36.12* | 52.55** | 99.83** | 10.9 |

*P < 0.05,
**P < 0.005

Figure 18:
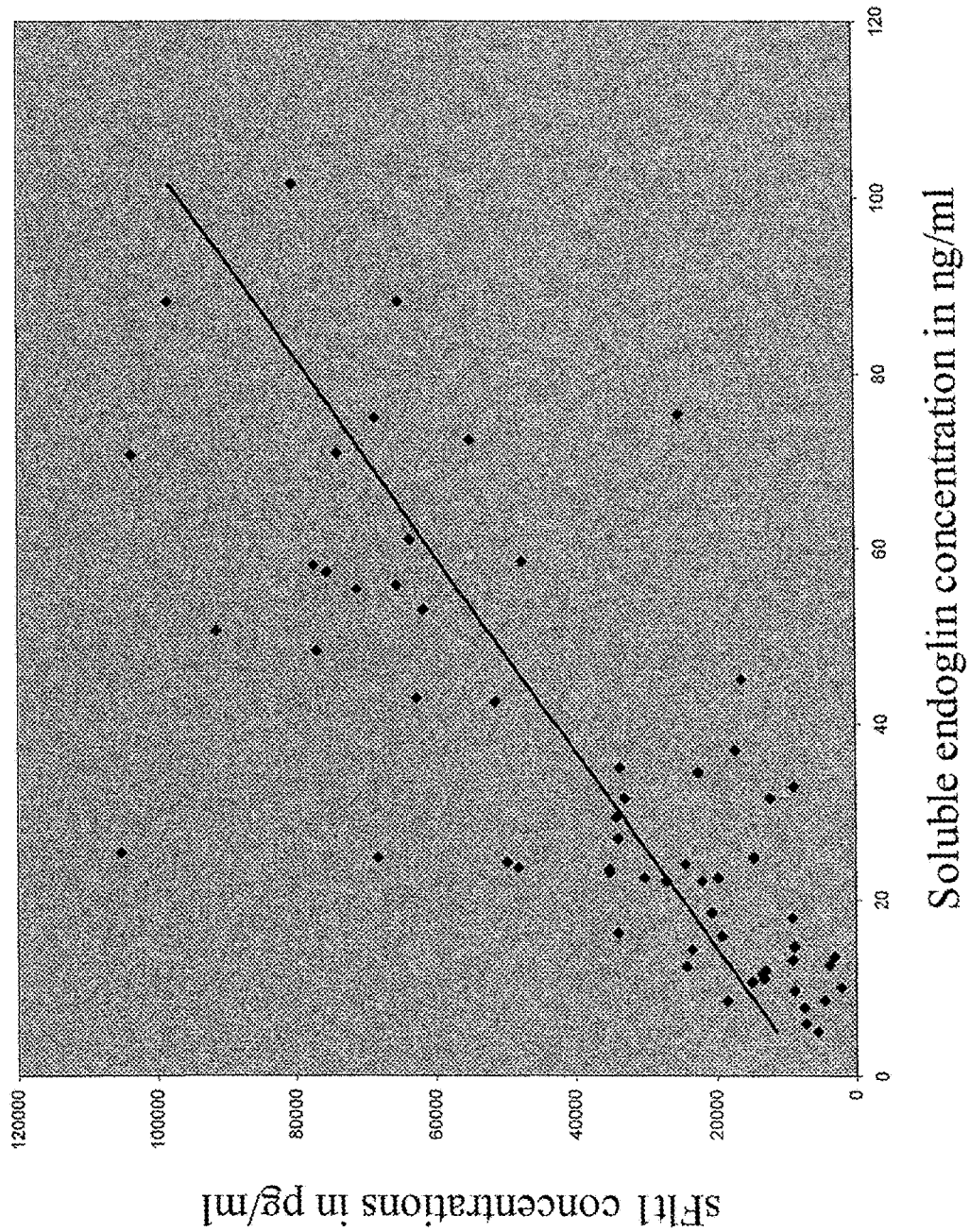
FIG. 18 is a graph showing the concentration of sFlt1 and soluble endoglin in the same pregnant patients plotted against each other.
Figure 20:
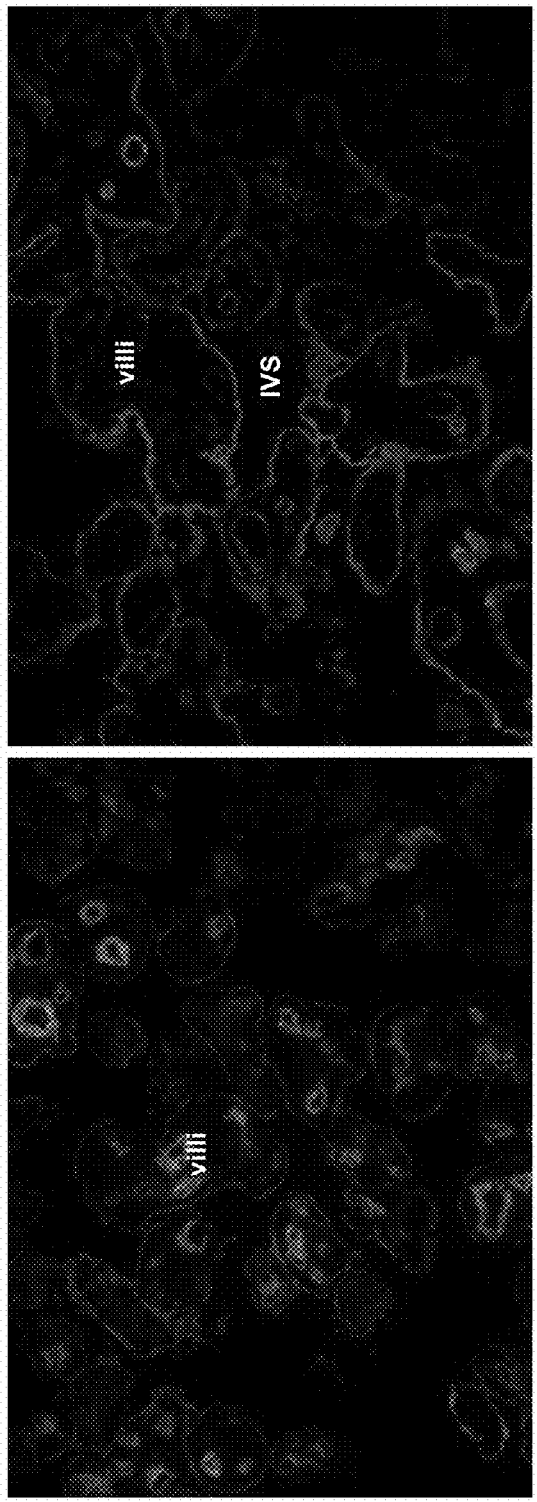
FIG. 20 shows photomicrographs of double immunofluorescence staining of endoglin (red) and smooth muscle actin (green) for pre-eclamptic placentas taken at 41.3 weeks. The antibody used to detect endoglin stains both full-length endoglin and the soluble endoglin. Control placentas for the appropriate gestational windows were derived from patients with pre-term labor.
Figure 21A:
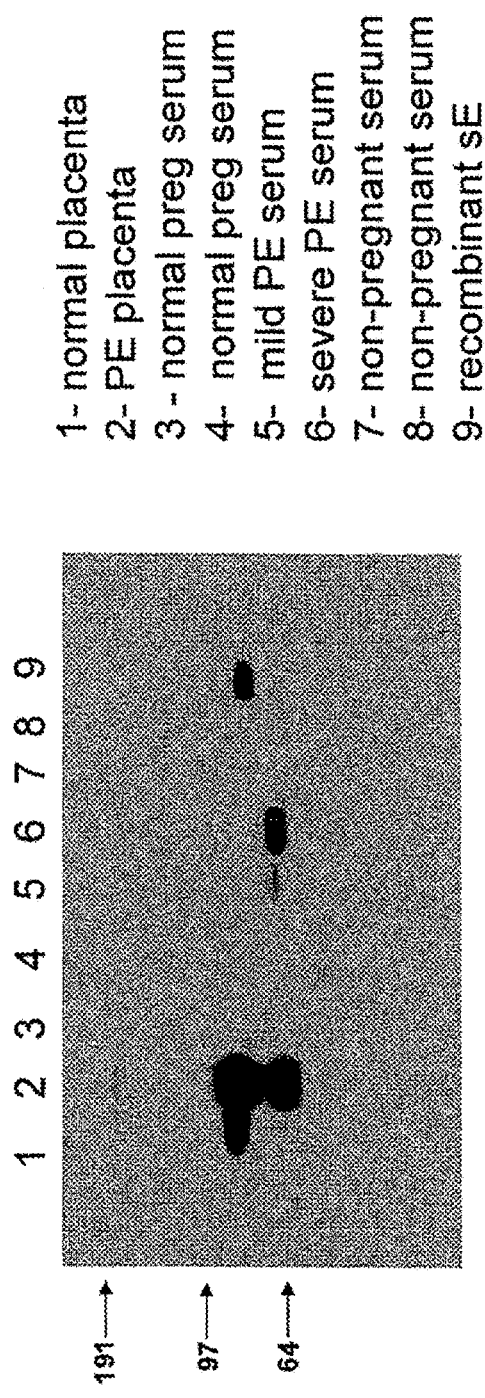
FIGS. 21A and 21B are photographs of autoradiograms from immunoprecipitation and western blot experiments for endoglin.
Figure 21B:
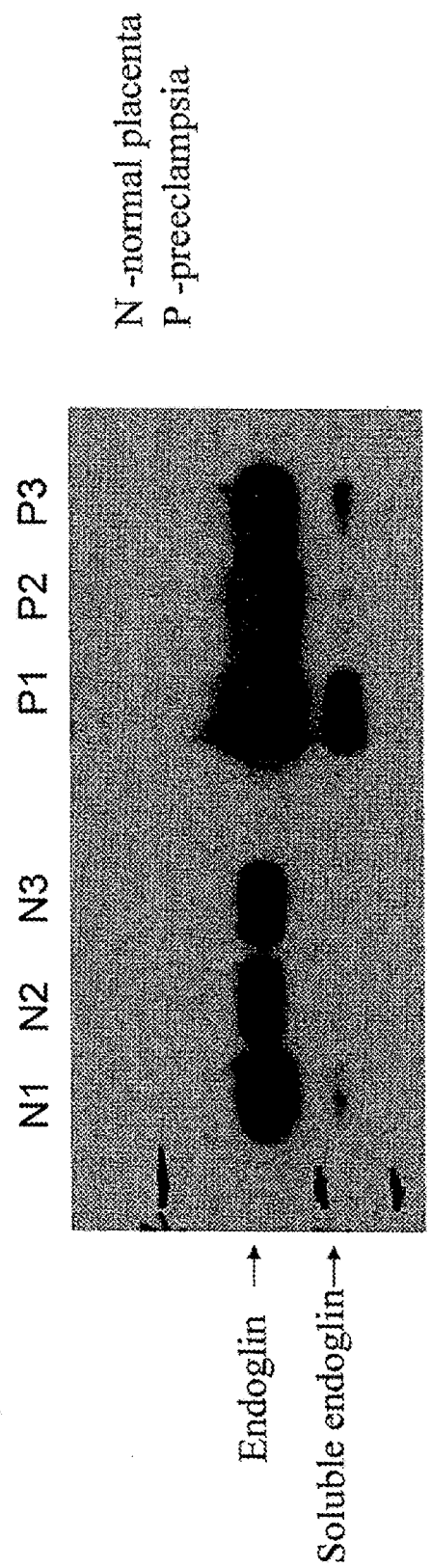

The average serum concentrations of soluble endoglin was at least two fold higher in mild pre-eclampsia and 3-4 fold higher in patients with severe pre-eclampsia. In pre-eclamptic patients complicated with the HELLP syndrome, the concentration of soluble endoglin was at least 5-10 fold higher than gestational age matched control specimens. Additionally, the levels of soluble endoglin in pregnant patients correlate with the levels of sFlt1 (FIG. 18). The R2 value for correlation was 0.6. (Note that the circulating concentrations of sFlt-1 reported here are at least 4-5 fold higher than previously published (Maynard et al., supra). This is due to a difference in the sensitivity of a new ELISA kit from R&D systems which lacks urea in the assay diluent and therefore gives consistently higher values than previously published.) In other words, patients with the highest levels of soluble endoglin also had the highest circulating levels of sFlt1. The origin of soluble endoglin is most likely the syncitiotrophoblast of the placenta as evidenced by the enhanced staining seen on our placental immunohistochemistry (FIGS. 19 and 20). These figures show that endoglin protein is expressed by the syncitiotrophoblasts and is vastly upregulated in pre-eclampsia. Our western blot data (FIGS. 21A and 21B) and northern blot further confirms that the soluble endoglin is a shed form of the extracellular domain of endoglin protein and is approximately 65 kDA in size and is expressed in excess quantities in pre-eclamptic placentas and that it circulates in excess quantities in pre-eclamptic placentas. The predicted length of the protein is approximately 437 amino acids.

Figure 22:
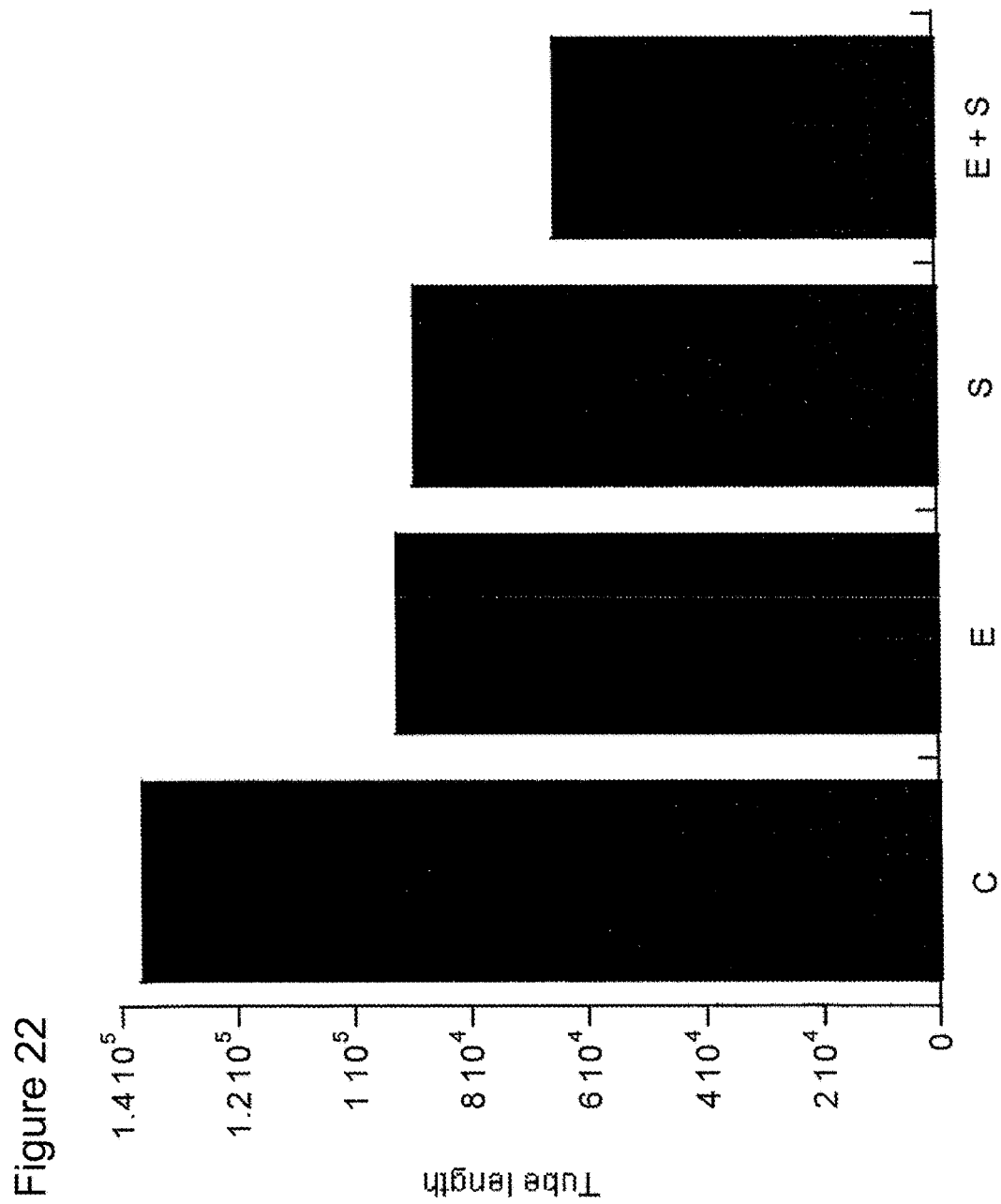
FIG. 22 is a graph showing the results of angiogenesis assays using HUVECs in growth factor reduced matrigels. Angiogenesis assays were performed in the presence of soluble endoglin or sFlt1 or both and the endothelial tube lengths quantitated. C—represents control, E—represents 1 µg/ml of soluble endoglin and S represents 1 µg/ml of sFlt1. E+S represent the combination of 1 µg/ml of E+1 µg/ml of sFlt1. Data represents a mean of three independent experiments.
Figure 23:
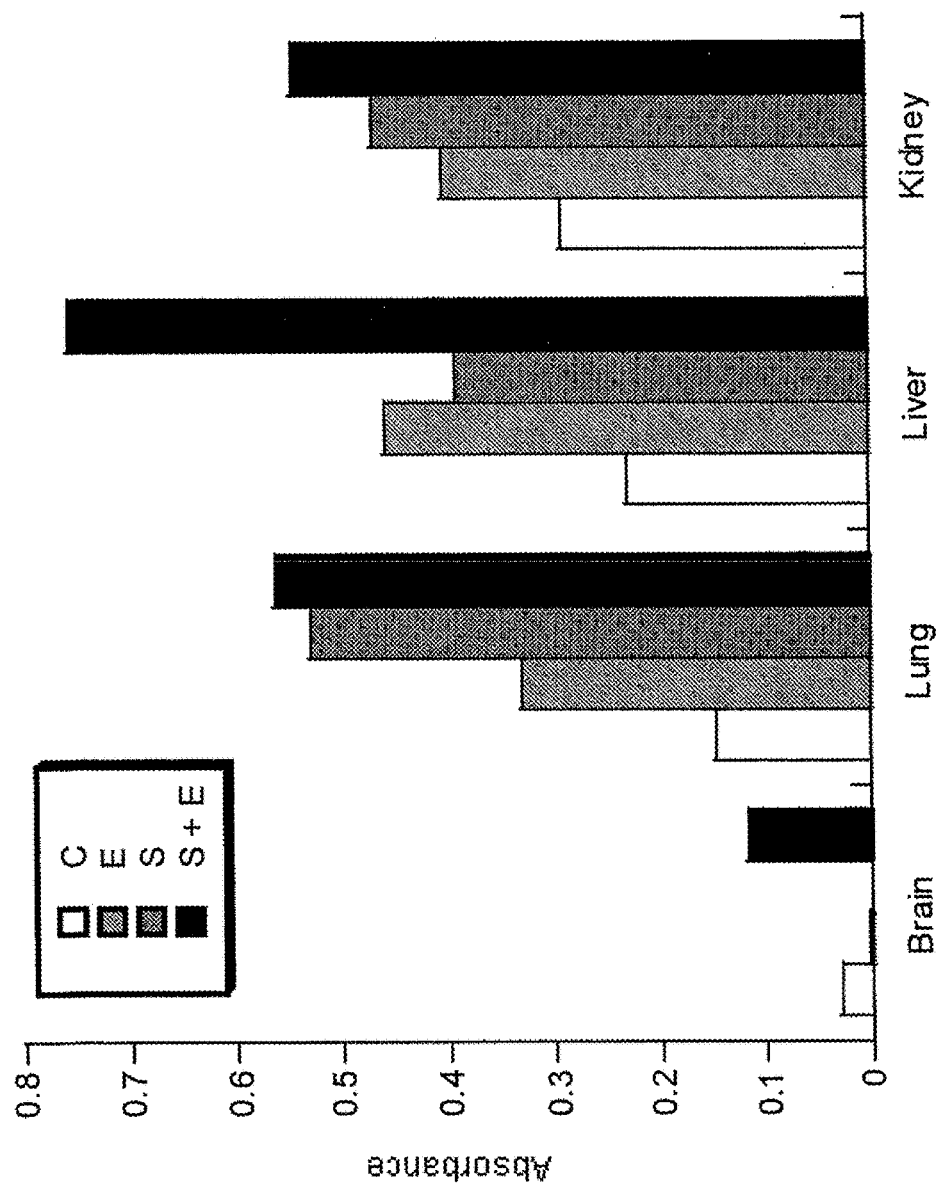
FIG. 23 is a graph showing the microvascular permeability in several organ beds assessed using Evans blue leakage in mice as described in the materials and methods. C—control (GFP), E—soluble endoglin, S-sFlt1 and S+E-sFlt1+soluble endoglin. Data represents a mean of 4 independent experiments.

Soluble Endoglin is an Anti-angiogenic Molecule and Induces Vascular Dysfunction We used an in vitro model of angiogenesis to understand the function of the soluble endoglin. Soluble endoglin modestly inhibits endothelial tube formation, that is further enhanced by the presence of sFlt1 (FIG. 22). In pre-eclampsia, it has been reported that in addition to endothelial dysfunction, there is also enhanced microvascular permeability as evidenced by edema and enhanced leakage of Evan's blue bound albumin extracellularly. In order to see if soluble endoglin induces microvascular leak, we used mice treated for 48 hours with soluble endoglin and sFlt. A combination of soluble endoglin and sFlt1 induced a dramatic increase in albumin leakage in the lungs, liver and the kidney and a modest leakage in the brain as demonstrated using Evan's blue assay (FIG. 23). soluble endoglin alone induced a modest leakage in the liver. These data suggest that soluble endoglin and sFlt1 combination are potent anti-angiogenic molecules and can induce significant vascular leakage.

Figure 24:
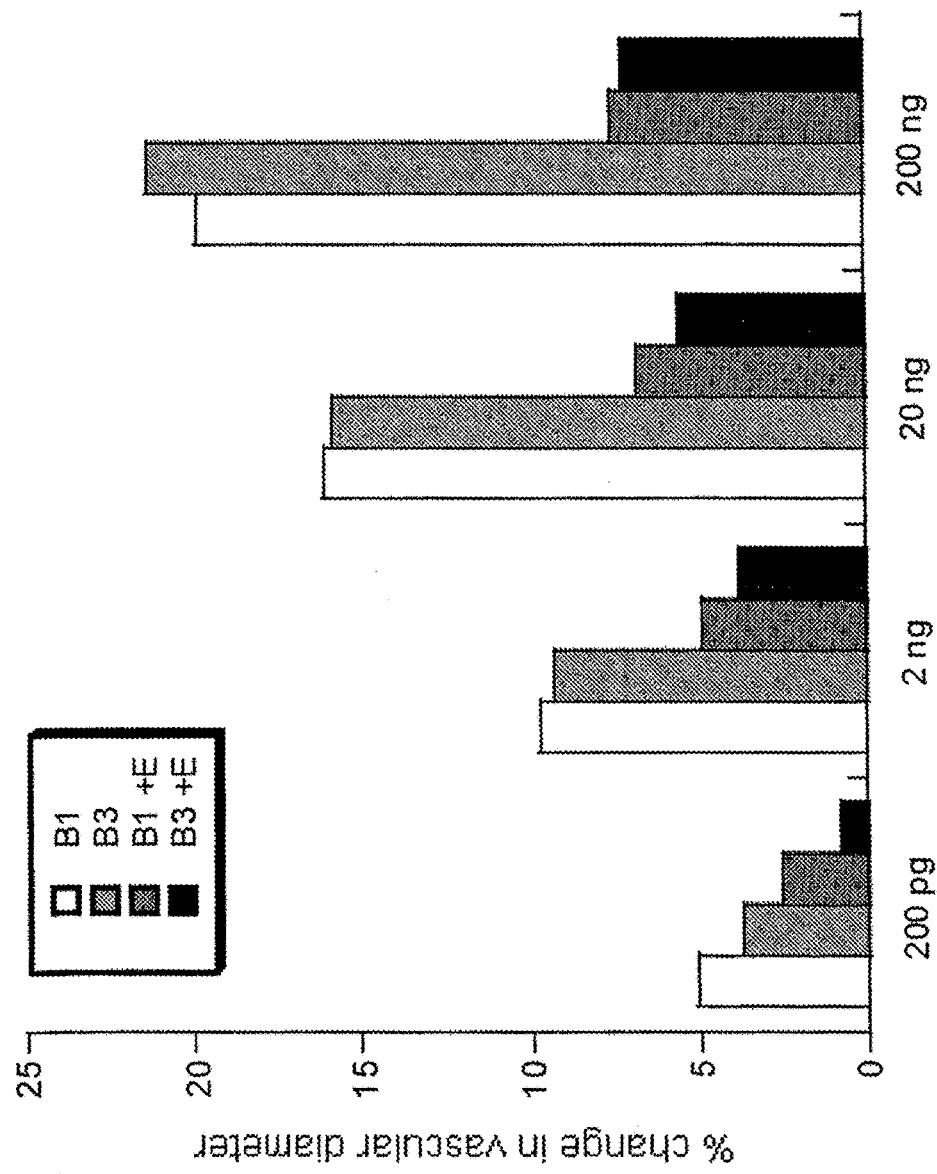
FIG. 24 is a graph showing the percent change in rat renal microvessel diameter were subjected to microvascular reactivity experiments in the presence of TGF-β1 (B1) and TGF-β3 (B3) from doses ranging from 200 pg/ml-200 ng/ml. These same experiments were repeated in the presence of soluble endoglin (E) at 1 µg/ml. These data presented are a mean of 4 independent experiments.
Figure 25:
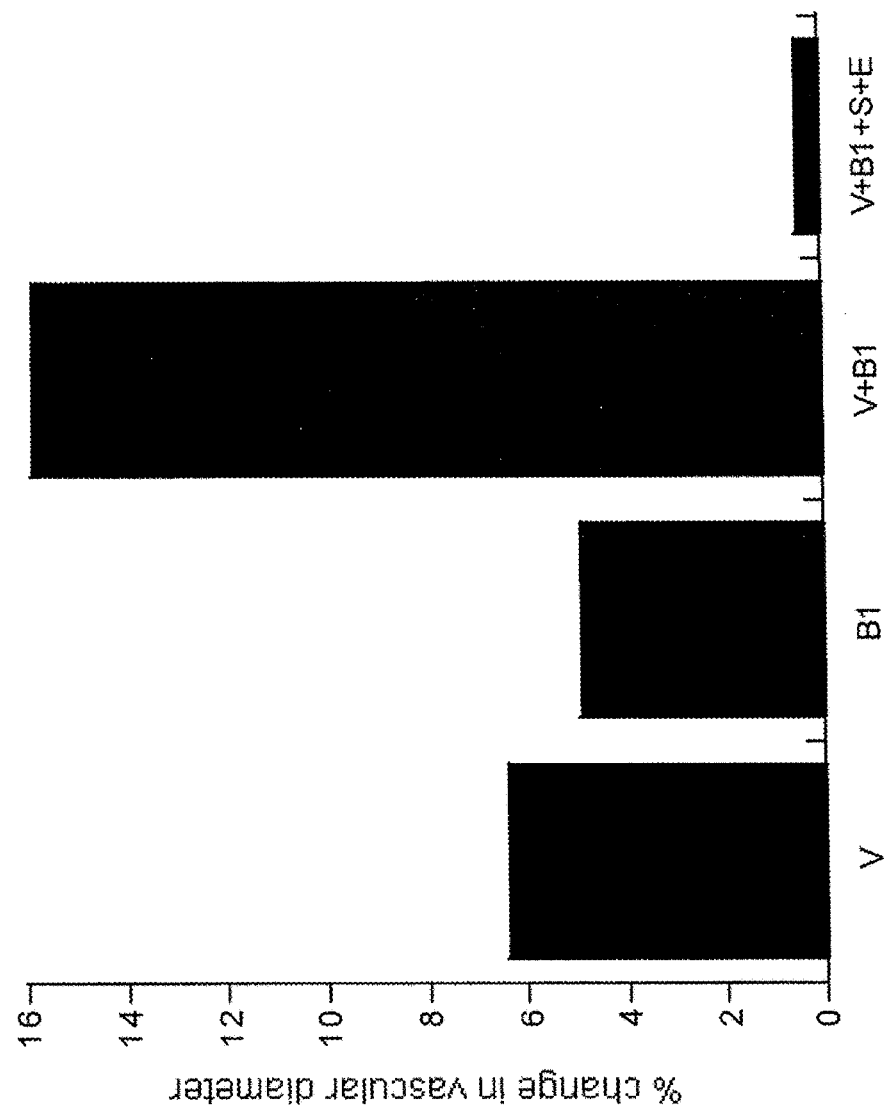
FIG. 25 is a graph showing the percent change in the vascular diameter of renal microvessels in the presence of 1 ng/ml of VEGF (V), TGF-β1 (B1) and the combination (V+B1). Also shown is the effect of this combination in the presence of 1 µg/ml each of sFlt1 (S) and soluble endoglin (E) (V+B1+S+E). The data represents a mean of 4 independent experiments.

To assess the hemodynamic effects of soluble endoglin, a series of microvascular reactivity experiments in rat renal microvessels were performed. We studied first the effects of TGF-β1 and TGF-β3—two known ligands of endoglin. Both TGF-β1 and TGF-β3 induced a dose-dependent increase in vascular diameter. Importantly in the presence of excess soluble endoglin, the effect of both the TGFs were significantly attenuated (FIG. 24). Finally, the combination of VEGF and TGF-β1 induced vasodilation which was blocked by excess soluble endoglin and sFlt1 (FIG. 25). This suggests that the sFlt1 and soluble endoglin may oppose the physiological vasodilation induced by angiogenic growth factors such as VEGF and TGF-β1 and induce hypertension.

In Vivo Effects of Soluble Endoglin and sFlt1

In order to assess the vascular effects of soluble endoglin and sFlt1, we resorted to adenoviral expression system in pregnant rats. Adenovirus encoding a control gene (CMV) or soluble endoglin or sFlt1 or sFlt1+ soluble endoglin were injected by tail vein on day 8 of pregnancy in Sprague Dawley rats. On day 17, animals were examined for pre-eclampsia phenotype. Table 8 includes the hemodynamic and biochemical data.

TABLE 8

Hemodynamic and biochemical data for adenovirus treated rat animal models.

| Groups | N | MAP in mmHg | Urine Alb/creat μg/mg | Platelet count × 1000/μl | LDH U/L | AST U/L | Fetal weight in gms |
|---|---|---|---|---|---|---|---|
| Control (CMV) | 4 | 86.33 | 84.17 | 1378 | 257 | 43 | 4.56 |
| sFlt1 | 4 | 134* | 3478.3* | 1247 | 324 | 78 | 3.55 |
| sE | 4 | 112* | 366.90 | 1406 | 463 | 95 | 3.20 |
| sFlt1 + sE | 4 | 145* | 6478.2* | 538* | 1428* | 187* | 2.50* |

MAP—mean arterial pressure (diastolic pressure + ⅓ pulse pressure);
Alb/Creat—Albumin/creatinine ratios;
LDH—Lactate dehydrogenase;
AST—Aspartate Aminotransferase.
*$P < 0.05$ when compared to control group.
Fetal weight is the sum of 4 fetuses chosen randomly per group
The average circulating concentrations of sFlt1 was 410 ng/ml in the sFlt1 group and 430 ng/ml in the sFlt1 + sE group. Average circulating concentrations of sE was 318 ng/ml in the sE group and 319 ng/ml in the sFlt1 + sE group.

Figure 26A:
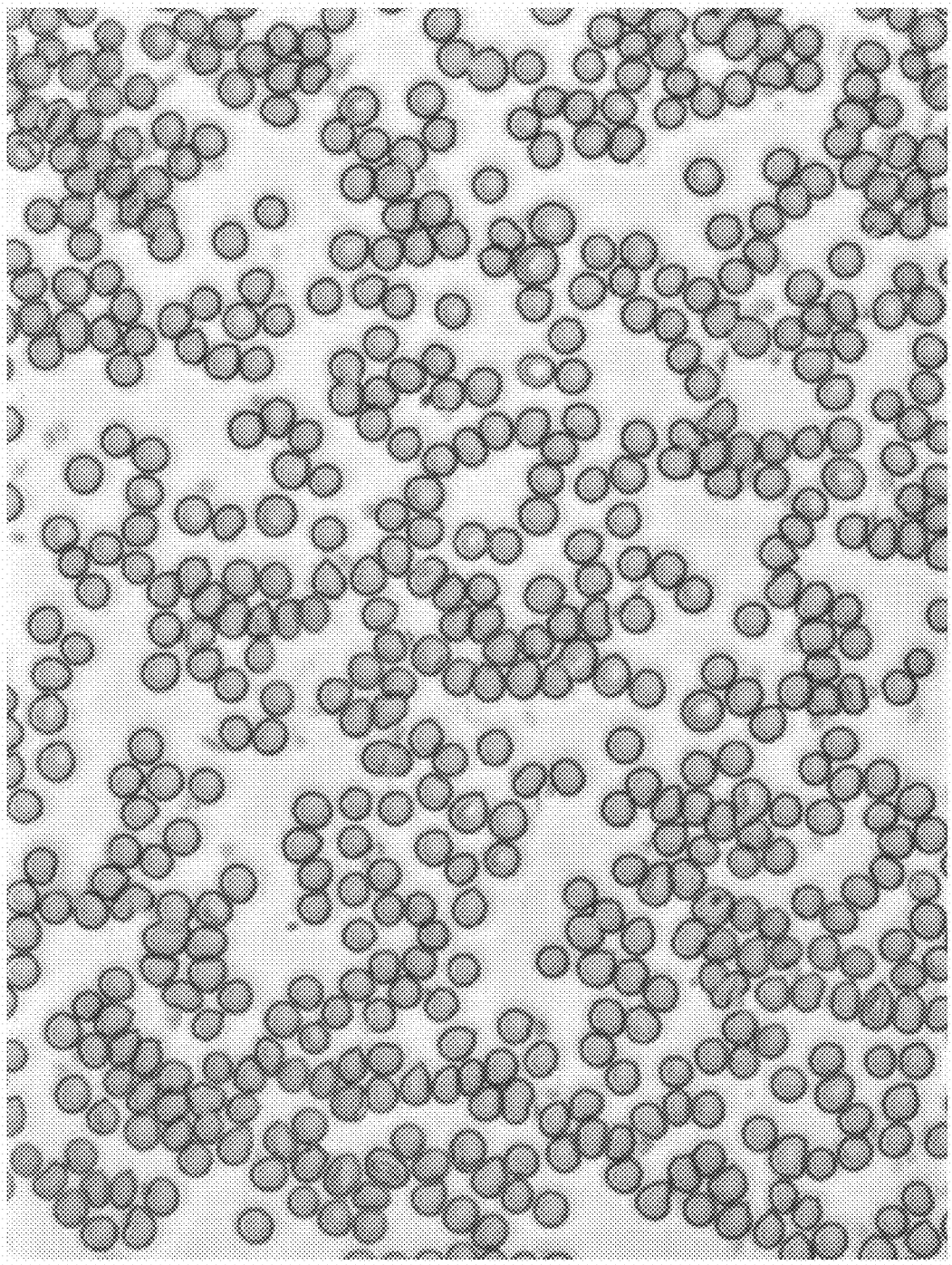
FIG. 26A is a photograph of a peripheral smear of blood samples taken at the time of sacrifice from pregnant rats injected with the combination of sFlt1 and a control adenoviruses (CMV).
Figure 26B:
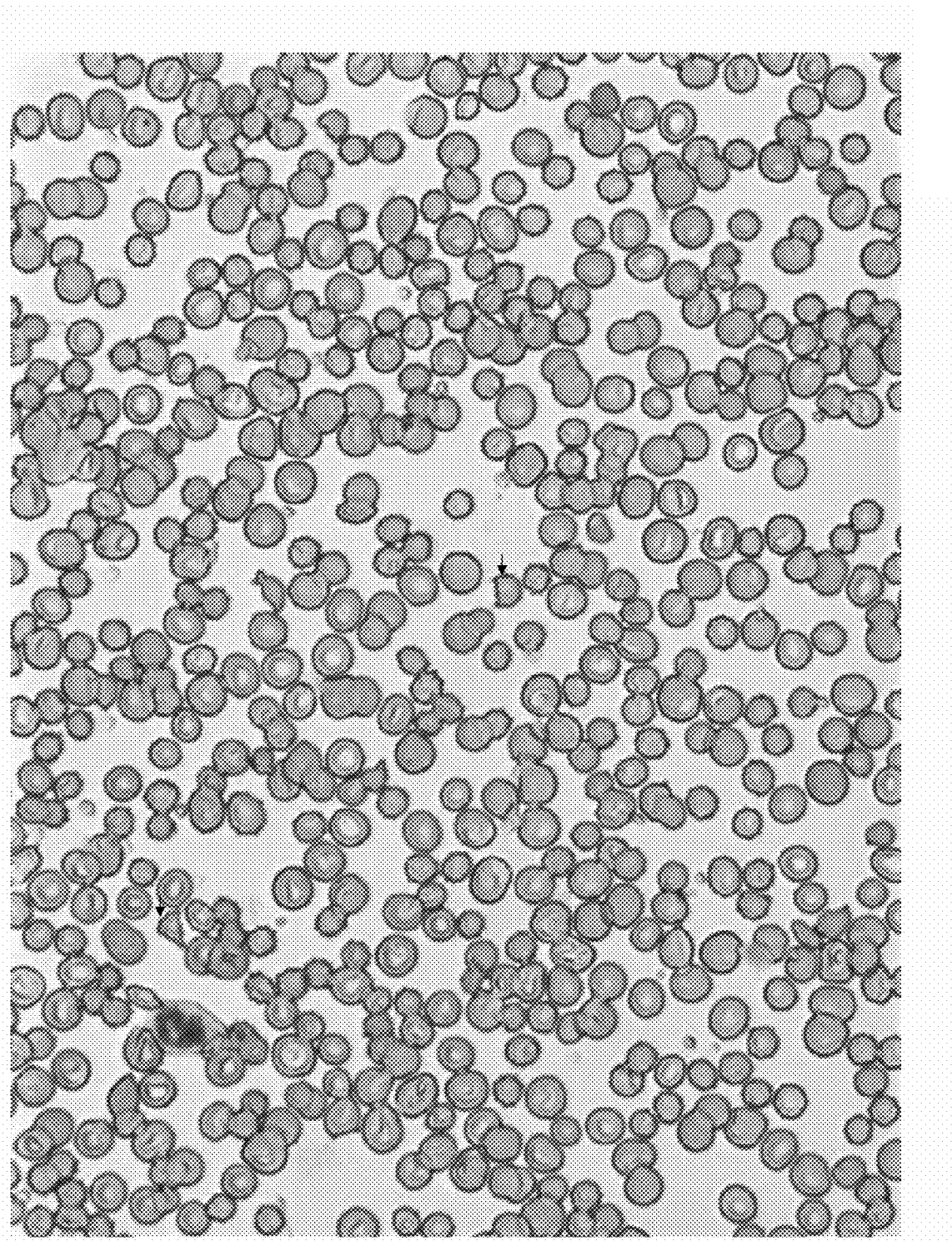
FIG. 26B is a photograph of a peripheral smear of blood samples taken at the time of sacrifice from pregnant rats injected with the combination of sFlt and adenoviruses expressing soluble endoglin and demonstrates active hemolysis as evidenced by schistocyes and increased reticulocyte count. Arrowheads represent schistocyte.
Figure 27A:
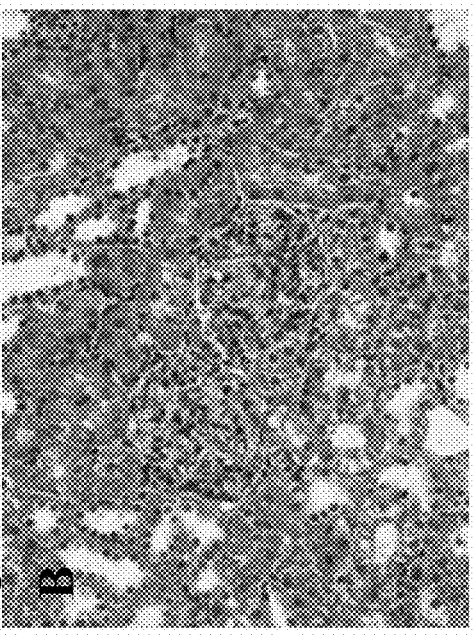
FIGS. 27A-27D are a series of photomicrographs showing the renal histology (H &E stain) of the various animal groups described in Table 8.
Figure 27B:
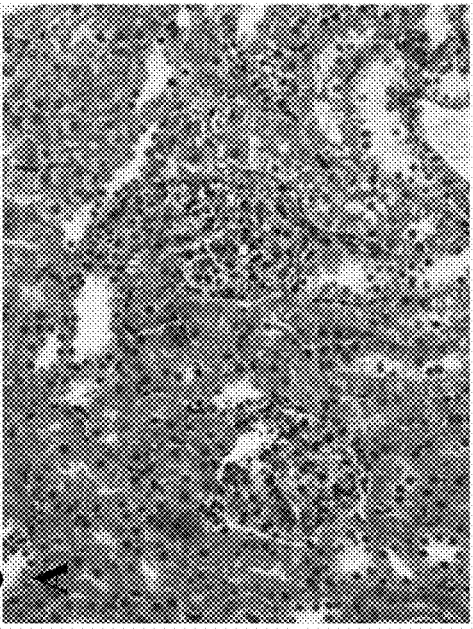
Figure 27C:
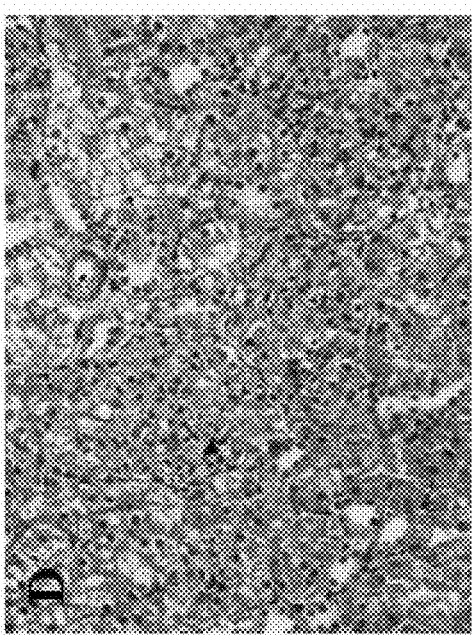
Figure 27D:
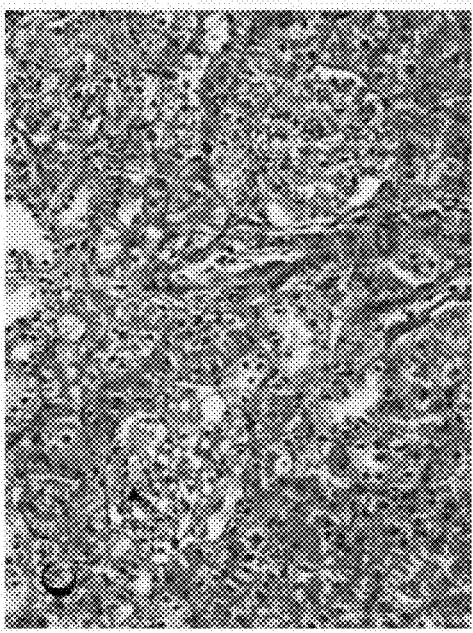

Soluble endoglin alone induced a mild hypertension. sFlt1 induced both hypertension and proteinuria, as previously reported. Importantly, the combination of sFlt1 and soluble endoglin induced severe hypertension, nephrotic range proteinuria, growth restriction of the fetuses and biochemical evidence of the development of the HELLP syndrome (elevated LDH, elevated AST and decreasing platelet counts) (Table 8). Evidence of hemolysis in the soluble endoglin+sFlt1 group was confirmed by peripheral smear which revealed schistocytes and reticulocytosis (FIGS. 26A-B). Finally, renal histology also confirmed a severe glomerular endotheliosis in the soluble endoglin+sFlt1 group (FIGS. 27A-27D).

Summary

These results demonstrate that soluble endoglin is up-regulated in pre-eclamptic placentas and is present at extremely high levels in patients with pre-eclampsia. The highest levels of soluble endoglin were present in patients with HELLP syndrome, one of the most severe forms of pre-eclampsia. These results also demonstrate that soluble endoglin levels correlated with the elevated sFlt1 in pregnant patients and was higher in those patients in whom there is a higher circulating sFlt1 levels. In addition, the results indicate that soluble endoglin is an anti-angiogenic molecule and disrupts endothelial function in multiple endothelial assays such as angiogenesis assays, microvascular permeability assays, and microvascular reactivity experiments. Importantly, soluble endoglin can amplify the toxic consequence of sFlt1 in these in vitro endothelial assays. Further, in in vivo assays, adenoviral expression of soluble endoglin induces mild hypertension without any significant proteinuria. However, in the presence of sFlt1, soluble endoglin induces significant vascular damage as evidenced by the presence of severe hypertension, proteinuria, glomerular endotheliosis, development of the HELLP syndrome and fetal growth restriction. These data suggests that soluble endoglin plays an important role in the causality of the maternal syndrome of pree-clampsia and underscore the need for agents that neutralize soluble endoglin for the treatment of pre-eclampsia.

The mechanism of soluble endoglin release is likely proteolytic cleavage of the extracellular region of the endoglin molecule. Specific proteases that are up-regulated in the pre-eclamptic tissue may serve as candidate molecules. One example would be the membrane type matrix metalloproteinase-1 (MT1-MMP) that has been shown to cleave beta-glycan, a molecule that shares similarity to endoglin (Velasco-Loyden G et al, *J. Biol. Chem.* 279:7721-33 (2004)).

Therefore inhibitors of such proteases may serve as valuable targets for the treatment of pre-eclampsia.

OTHER EMBODIMENTS

The description of the specific embodiments of the invention is presented for the purposes of illustration. It is not intended to be exhaustive or to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference.

Other embodiments are in the claims.

What is claimed is:

1. A method of treating a pregnancy related hypertensive disorder in a pregnant female subject having an increase in the level of soluble endoglin relative to a normal reference, said method comprising administering to said subject prior to the 20$^{th}$ week of pregnancy an antibody or antigen-binding fragment thereof that specifically binds to soluble endoglin, wherein said administering is for a time and in an amount sufficient to treat said pregnancy related hypertensive disorder in said subject.

2. The method of claim 1, wherein said pregnancy related hypertensive disorder is selected from the group consisting of pre-eclampsia, eclampsia, gestational hypertension, chronic hypertension, HELLP syndrome, and pregnancy with a small for gestational age (SGA) infant.

3. The method of claim 2, wherein said pregnancy related hypertensive disorder is pre-eclampsia or eclampsia.

4. The method of claim 1, further comprising administering a compound selected from the group consisting of a purified anti-sFlt-1 antibody, an sFlt-1 antigen-binding fragment, nicotine, theophylline, adenosine, nifedipine, minoxidil, magnesium sulfate, vascular endothelial growth factor (VEGF), and placental growth factor (PIGF).

5. The method of claim 1, wherein said method further comprises monitoring said pregnancy related hypertensive disorder in said subject, wherein said monitoring comprises measuring the level of soluble endoglin polypeptide in a sample from said subject.

6. The method of claim 5, wherein the level of soluble endoglin is the level of free, bound, or total soluble endoglin.

7. The method of claim 5, wherein the level of soluble endoglin is the level of an endoglin polypeptide resulting from degradation or enzymatic cleavage.

8. The method of claim 1, wherein said antibody or antigen-binding fragment thereof is capable of reducing soluble endoglin expression or biological activity.

9. The method of claim 1, wherein said antibody or antigen-binding fragment thereof is a human or humanized antibody.

10. The method of claim 1, wherein said antigen-binding fragment is an Fv, Fab, Fab', F(ab')$_2$, or scFv fragment.

11. The method of claim 5, wherein said sample is serum or plasma and said treating comprises reducing the level of soluble endoglin polypeptide in the serum or plasma to less than 25 ng/ml.

12. The method of claim 5, wherein (i) said measuring is performed on two or more occasions or (ii) said monitoring comprises comparing the level of soluble endoglin polypeptide in the sample from the subject to a positive reference sample.

13. The method of claim 5, wherein said monitoring is used to determine a therapeutic dosage of said antibody or antigen-binding fragment thereof.

14. The method of claim 5, wherein said monitoring further comprises calculating the relationship between levels of soluble endoglin, sFlt-1, VEGF, or PIGF using a metric, wherein said metric is a pre-eclampsia anti-angiogenic index (PAAI): [sFlt-1/VEGF +PIGF], a soluble endoglin anti-angiogenic index: [(sFlt-1 +0.25 soluble endoglin)/PIGF], or [(soluble endoglin +sFlt-1)/PIGF], and wherein an alteration in the level of said metric in the sample from said subject relative to said normal reference is a diagnostic indicator of the pregnancy related hypertensive disorder in said subject.

15. The method of claim 14, wherein:
  (a) a PAAI value less than 20 indicates an improvement in said pregnancy related hypertensive disorder; or
  (b) said metric is used to determine the dosage of the antibody or antigen-binding fragment thereof.

16. The method of claim 1, wherein the administering is performed about 9 to about 11 weeks before onset of symptoms of the pregnancy related hypertensive disorder.

17. The method of claim 1, wherein the administering is performed about 12 to about 14 weeks before onset of symptoms of the pregnancy related hypertensive disorder.

18. The method of claim 1, wherein the administering is performed in the first or second trimester of the pregnancy.

19. The method of claim 1, wherein the administering is performed on or about the 12$^{th}$, 14$^{th}$, 16$^{th}$, or 18$^{th}$ week of the pregnancy.

20. The method of claim 1, wherein the administering is performed on or about the 17$^{th}$ week to before the 20$^{th}$ week of the pregnancy.

21. The method of claim 1, wherein the subject has an increase in the level of soluble endoglin relative to a normal reference about 9 to about 11 weeks before the onset of symptoms of the pregnancy related hypertensive disorder.

22. The method of claim 1, wherein the subject has an increase in the level of soluble endoglin relative to a normal reference about 12 to about 14 weeks before the onset of symptoms of the pregnancy related hypertensive disorder.

23. The method of claim 1, wherein the subject has an increase in the level of soluble endoglin relative to a normal reference in the first or second trimester of the pregnancy.

24. The method of claim 1, wherein the subject has an increase in the level of soluble endoglin relative to a normal reference on or about the $12^{th}$, $14^{th}$, $16^{th}$, or $18^{th}$ week of the pregnancy.

25. The method of claim 1, wherein the subject has an increase in the level of soluble endoglin polypeptide relative to a normal reference on or about the $17^{th}$ week up to before the $20^{th}$ week of the pregnancy.

26. The method of claim 1, wherein the subject has an increase in the level of soluble endoglin in the second trimester of pregnancy relative to the first trimester of pregnancy.

27. The method of claim 3, wherein the pre-eclampsia is premature pre-eclampsia.

\* \* \* \* \*